US011337988B2

(12) United States Patent
Collins et al.

(10) Patent No.: US 11,337,988 B2
(45) Date of Patent: May 24, 2022

(54) USE OF OUABAIN ANTAGONISTS TO INHIBIT VIRAL INFECTION

(71) Applicant: The United States of America, as represented by the Secretary, Department of Health and Human Services, Bethesda, MD (US)

(72) Inventors: Peter Collins, Silver Spring, MD (US); Matthias Lingemann, Bethesda, MD (US); Shirin Munir, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 195 days.

(21) Appl. No.: 16/584,679

(22) Filed: Sep. 26, 2019

(65) Prior Publication Data

US 2020/0101086 A1 Apr. 2, 2020

Related U.S. Application Data

(60) Provisional application No. 62/737,899, filed on Sep. 27, 2018.

(51) Int. Cl.

| | |
|---|---|
| *A61K 31/58* | (2006.01) |
| *A61K 9/00* | (2006.01) |
| *A61P 31/14* | (2006.01) |

(52) U.S. Cl.

CPC ............ *A61K 31/58* (2013.01); *A61K 9/0043* (2013.01); *A61K 9/0078* (2013.01); *A61P 31/14* (2018.01)

(58) Field of Classification Search

CPC .... A61K 31/58; A61K 9/0078; A61K 9/0043; A61P 31/14

See application file for complete search history.

(56) References Cited

U.S. PATENT DOCUMENTS

| | | | |
|---|---|---|---|
| 5,591,734 | A | 1/1997 | Quadri et al. |
| 9,127,037 | B2 | 9/2015 | Cerri et al. |
| 9,408,854 | B2 | 8/2016 | Bianchi et al. |
| 9,868,757 | B2 | 1/2018 | Ferrari et al. |
| 2011/0038852 | A1 | 2/2011 | Meldrum et al. |
| 2011/0105423 | A1 | 5/2011 | Shaw et al. |
| 2012/0028945 | A1 | 2/2012 | Ferrari et al. |
| 2013/0018024 | A1 | 1/2013 | Bianchi et al. |

FOREIGN PATENT DOCUMENTS

| | | |
|---|---|---|
| EP | 0583578 | 4/1997 |

OTHER PUBLICATIONS

American Academy of Pediatrics Subcommittee on Diagnosis and Management of Bronchiolitis, "Diagnosis and Management of Bronchiolitis," *Pediatrics* 118:1774-1793, 2006.
Ashbrook et al., "Antagonism of the Sodium-Potassium ATPase Impairs Chikungunya Virus Infection," *mBio* 7:e00693-16, 2016.
Biscardi et al., "c-Src-mediated Phosphorylation of the Epidermal Growth Factor Receptor on Tyr845 and Tyr1101 Is Associated with Modulation of Receptor Function," *J Biol Chem.*274:8335-8343, 1999.

Burkard et al., "ATP1A1-Mediated Src Signaling Inhibits Coronavirus Entry into Host Cells," *J Virol*. 89:4434-4448, 2015.

Cherniavsky-Lev et al., "Ouabain-induced Internalization and Lysosomal Degradation of the $Na^+/K^+$-ATPase," *J Biol Chem*. 289:1049-1059, 2014.

Dodson et al., "Inhibitors of the Sodium Potassium ATPase that Impair Herpes Simplex Virus Replication Identified via a Chemical Screening Approach," *Virology* 366:340-348, 2007.

Donepudi et al., "c-Src trafficking and co-localization with the EGF Receptor promotes EGF ligand-independent EGF Receptor Activation and Signaling," *Cell Signal*. 20:1359-1367, 2008.

Ferrari et al., "PST2238: A New Antihypertensive Compound That Antagonizes the Long-Term Pressor Effect of Ouabain," *J Pharmacol Exp Ther*. 285:83-94, 1998.

Ferrari et al., "PST 2238: A New Antihypertensive Compound that Modulates Na+,K+-ATPase and Antagonizes the Pressor Effect of OLF," *Cardiovasc Drug Rev*. 17:39-57, 1999.

Ferrari et al., "Rostafuroxin: an ouabain antagonist that corrects renal and vascular $Na^+$-$K^+$-ATPase alterations in ouabain and adducin-dependent hypertension," *Am J Physiol regul Integr Comp Physiol*. 290:R529-R535, 2006.

García-Dorival et al., "Elucidation of the Ebola Virus VP24 Cellular Interactome and Disruption of Virus Biology through Targeted Inhibition of Host-Cell Protein Function," *J Proteome Res*. 13:5120-5135, 2014.

Gopalakrishnan et al., "Effects of Receptor Clustering on Ligand Dissociation Kinetics: Theory and Simulations," *Biophys J*. 89:3686-3700, 2005.

Grosso et al., "Suppression of Adenovirus Replication by Cardiotonic Steroids," *J Virol*. 91:e01623-16, 2017.

Hailstones et al., "Regulation of caveolin and caveolae by cholesterol in MDCK cells," *J Lipid Res*. 39:369-379, 1998.

Hallak et al., "Regulation of caveolin and caveolae by cholesterol in MDCK cells," *J Virol*. 74:10508-10513, 2000.

Heylen et al., "Drug candidates and model systems in respiratory syncytial virus antiviral drug discovery," *Biochem Pharmacol*. 127:1-12, 2017.

Iwasaki et al., "Interactome analysis of the lymphocytic choriomeningitis virus nucleoprotein in infected cells reveals ATPase Na+/K+ transporting subunit Alpha 1 and prohibitin as host-cell factors involved in the life cycle of mammarenaviruses," *PLoS Pathogens*. 14:e1006892, 2018.

Karuppannan et al., "Natural compounds inhibiting the replication of Porcine reproductive and respiratory syndrome virus," *Antiviral Res*. 94:188-194, 2012.

(Continued)

*Primary Examiner* — Barbara P Badio

(74) *Attorney, Agent, or Firm* — Klarquist Sparkman, LLP

(57) ABSTRACT

Embodiments of a method for inhibiting viral infection in a subject are provided herein. In some embodiments, the method comprises administration of a competitive antagonist of ouabain binding to ATP1A1 to inhibit respiratory syncytial virus infection in the subject.

15 Claims, 31 Drawing Sheets
(17 of 31 Drawing Sheet(s) Filed in Color)

Specification includes a Sequence Listing.

(56) References Cited

OTHER PUBLICATIONS

Kolokoltosov et al., "Small Interfering RNA Profiling Reveals Key Role of Clathrin-Mediated Endocytosis and Early Endosome Formation for Infection by Respiratory Syncytial Virus," *J Virol.* 57:7786-8700, 2007.

Krzyzaniak et al., "Host cell entry of respiratory syncytial virus involves macropinocytosis followed by proteolytic activation of the F protein," *PLoS Pathogens* 9:e1003309, 2013.

Liu et al., "Ouabain interaction with cardiac Na+/K+ ATPase initiates signal cascades independent of changes in intracellular Na+ and Ca2+ concentrations," *J Biol Chem.* 275:27838-27844, 2000.

Liu et al., "Role of caveolae in signal-transducing function of cardiac $Na^+/K^+$-ATPase," *Am J Physiol Cell Physiol.* 254:C1550-C1560, 2003.

Liu et al., "Ouabain-induced endocytosis of the plasmalemmal Na/K-ATPase in LLC-PK1 cells requires caveolin-1," *Kidney Int.* 67:1844-1854, 2005.

Lussignol et al., "Proteomics of HCV virions reveals an essential role for the nucleoporin Nup98 in virus morphogenesis," *PNAS* 113:2484-2489, 2016.

Mehedi et al.., "Actin-Related Protein 2 (ARP2) and Virus-Induced Filopodia Facilitate Human Respiratory Syncytial Virus Spread," *PLos Pathogens* 12:e1006062, 2012.

Ostrom et al., "Receptor Number and Caveolar Co-localization Determine Receptor Coupling Efficiency to Adenylyl Cyclase," *J Biol Chem.* 276:42063-42069, 2001.

San-Juan-Vergara et al., "Cholesterol-Rich Microdomains as Docking Platforms for Respiratory Syncytial Virus in Normal Human Bronchial Epithelial Cells," *J Virol.* 56:1832-1843, 2012.

Su et al., "Anti-HSV activity of digitoxin and its possible mechanisms," *Antiviral Res.* 79:62-70, 2008.

Tian et al., "Binding of Src to $Na^+/K^+$-ATPase Forms a Functional Signaling Complex," *Mol Biol. Cell* 17:317-326, 2006.

Wang et al., "Ouabain Assembles Signaling Cascades through the Caveolar $Na^+/K^+$-ATPase," *J Biol Chem.* 279:17250-17259, 2004.

Wong et al., "Digoxin Suppresses HIV-1 Replication by Altering Viral RNA Processing," *PLoS Pathogens* 9:e1003241, 2013.

Xie et al., "$Na^+$-$K^+$-ATPase-Mediated Signal Transduction: From Protein Interaction to Cellular Function," *Mol Interv.* 3:157-168, 2003.

Fearns and Deval, "New antiviral approaches for respiratory syncytial virus and other mononegaviruses: Inhibiting the RNA polymerase," *Antiviral Res.* 134: 63-76, 2016.

Lingemann et al., "The alpha-1 subunit of the $Na^+$, $K^+$-ATPase (ATP1A1) is required for macropinocytic entry of respiratory syncytial virus (RSV) in human respiratory epithelial cells," *PLoS Path.* 15.8: e1007963, Aug. 2019 (37 pages).

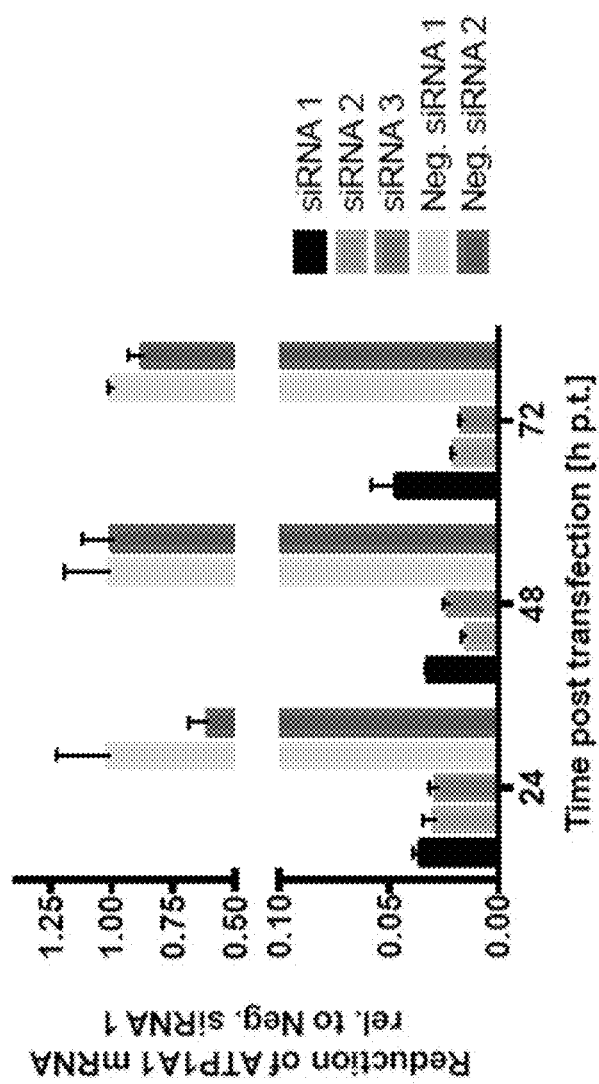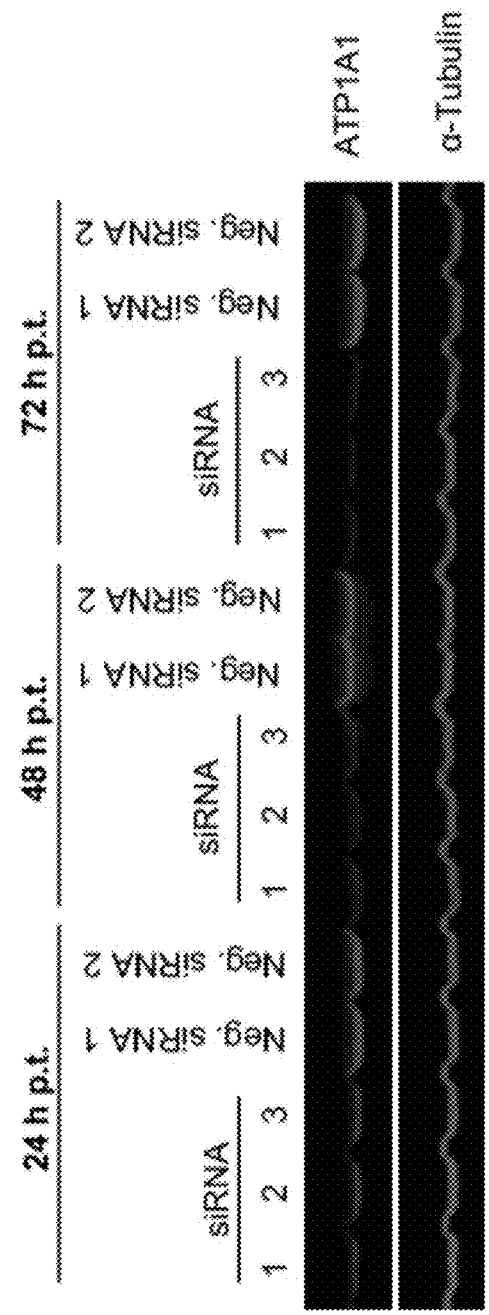
FIG. 1A
FIG. 1B

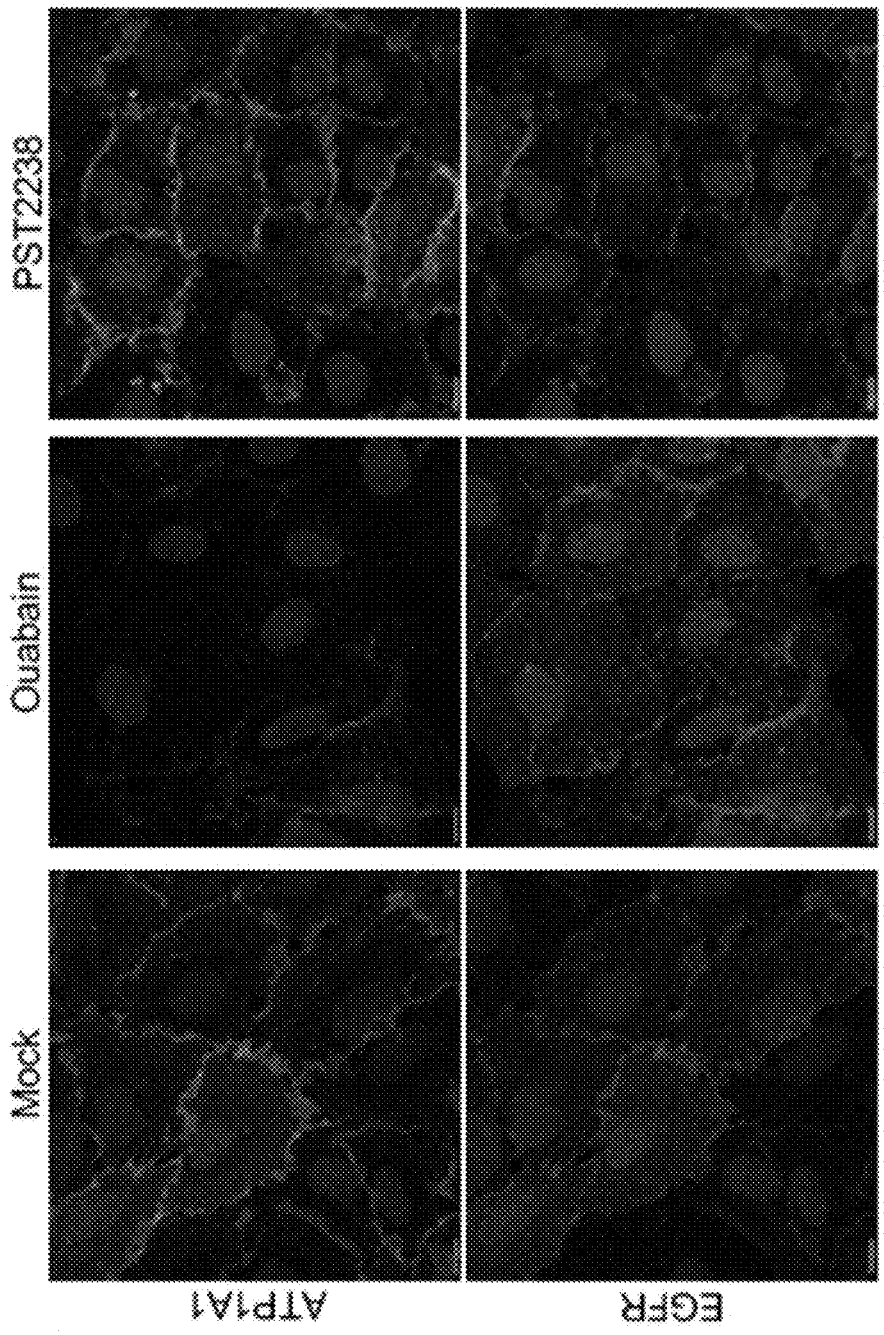

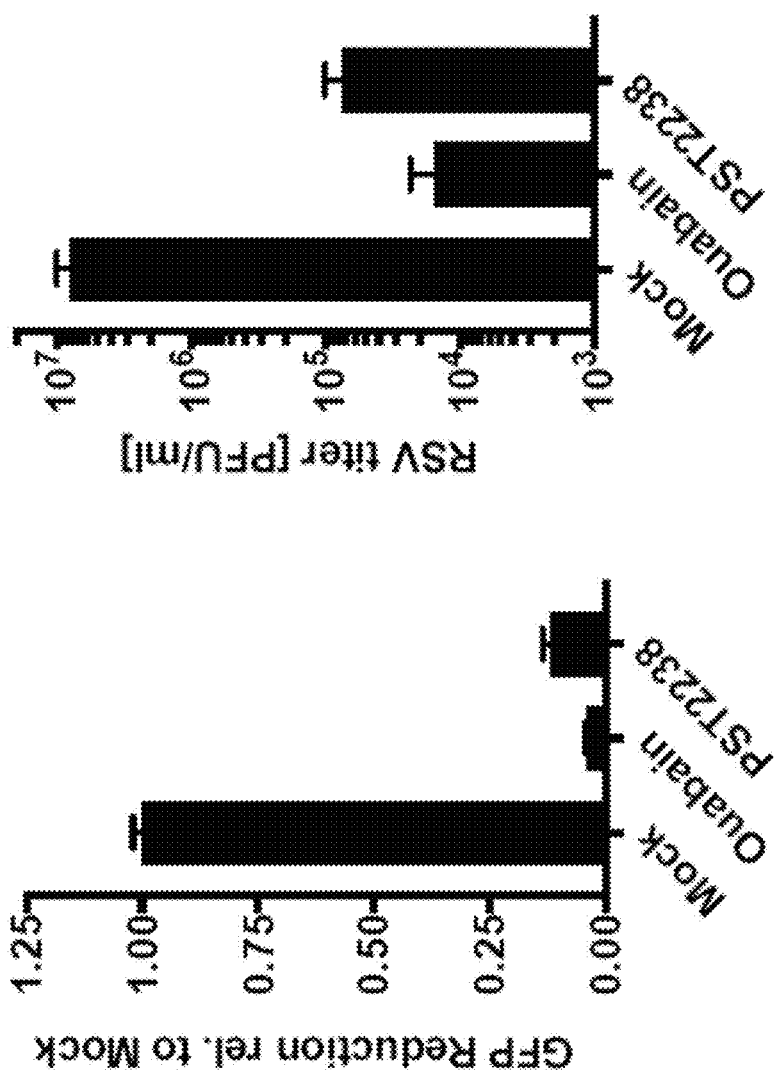

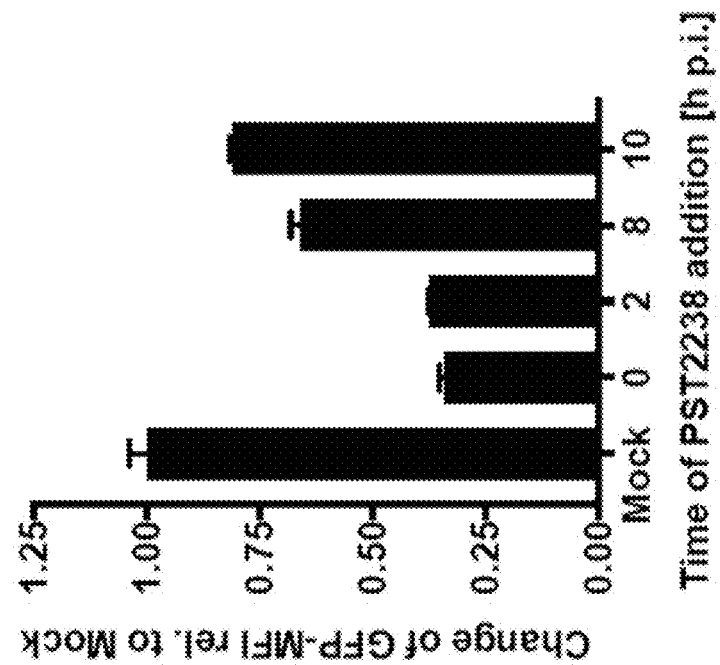
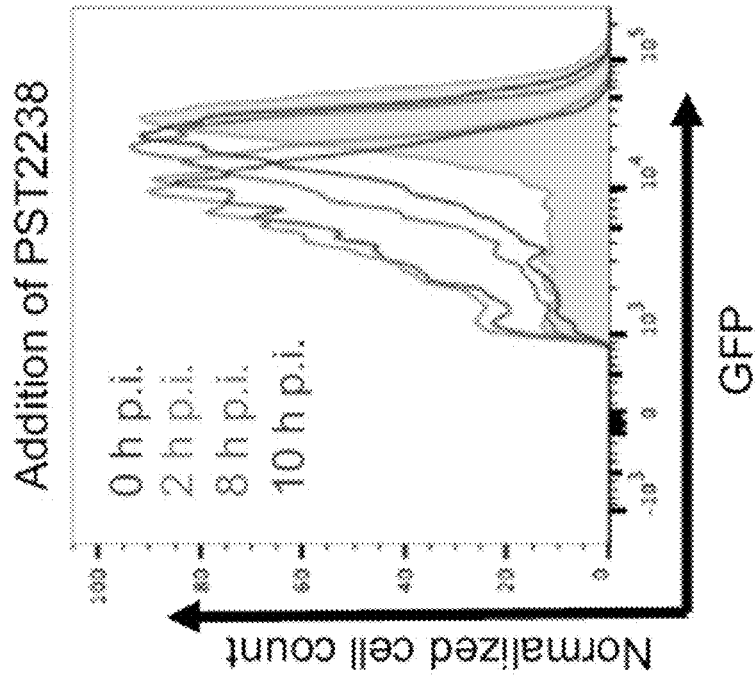
FIG. 5F
FIG. 5G

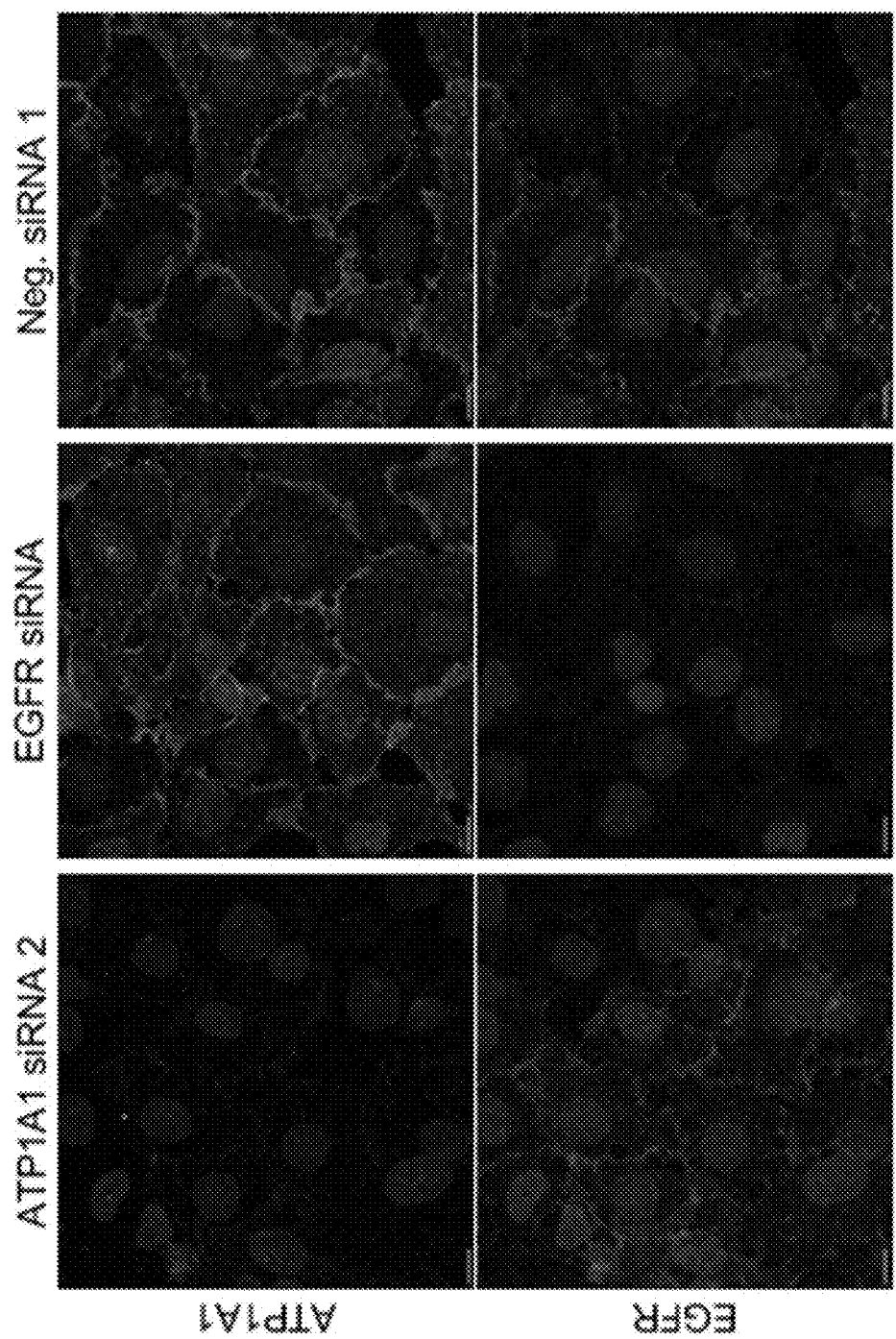

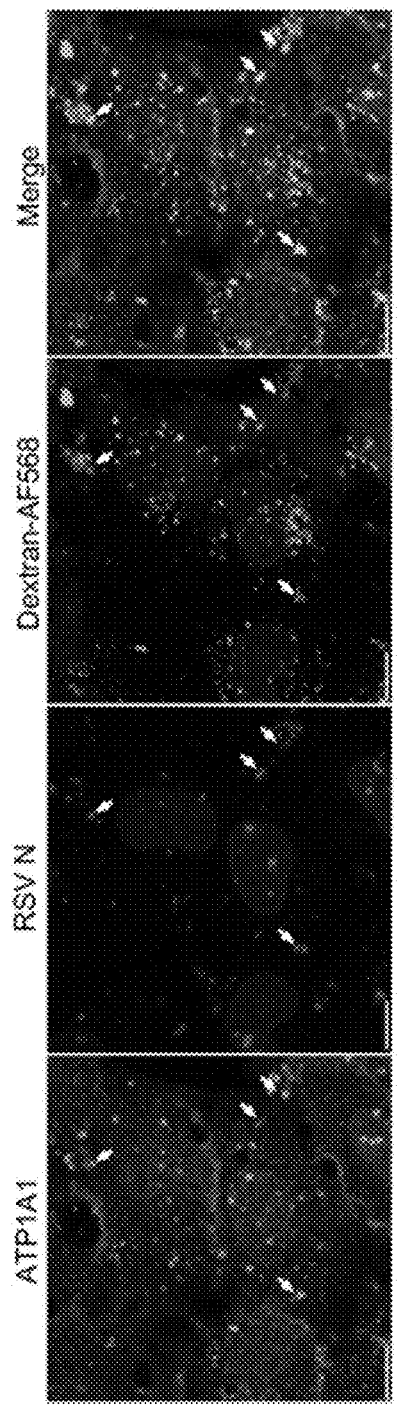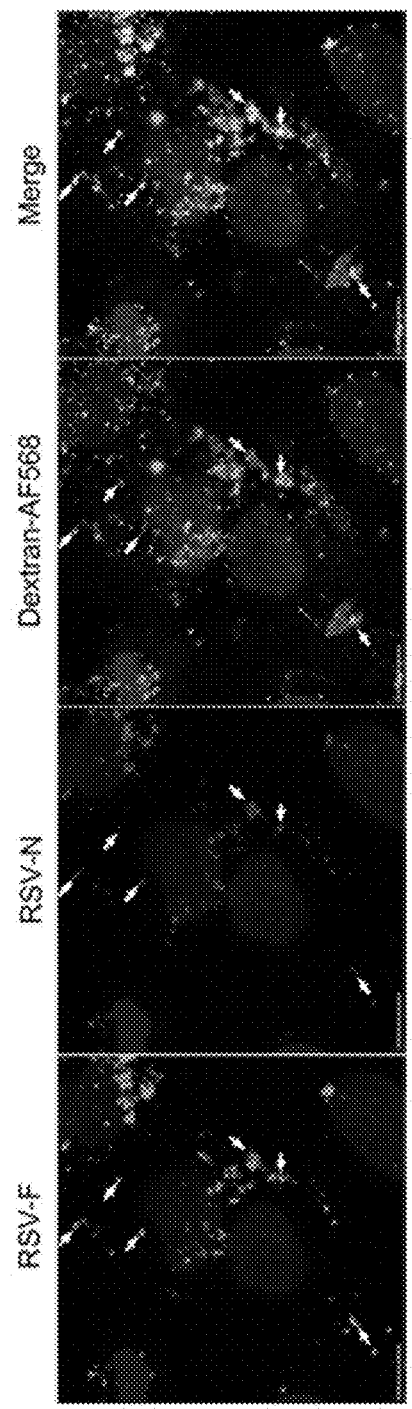

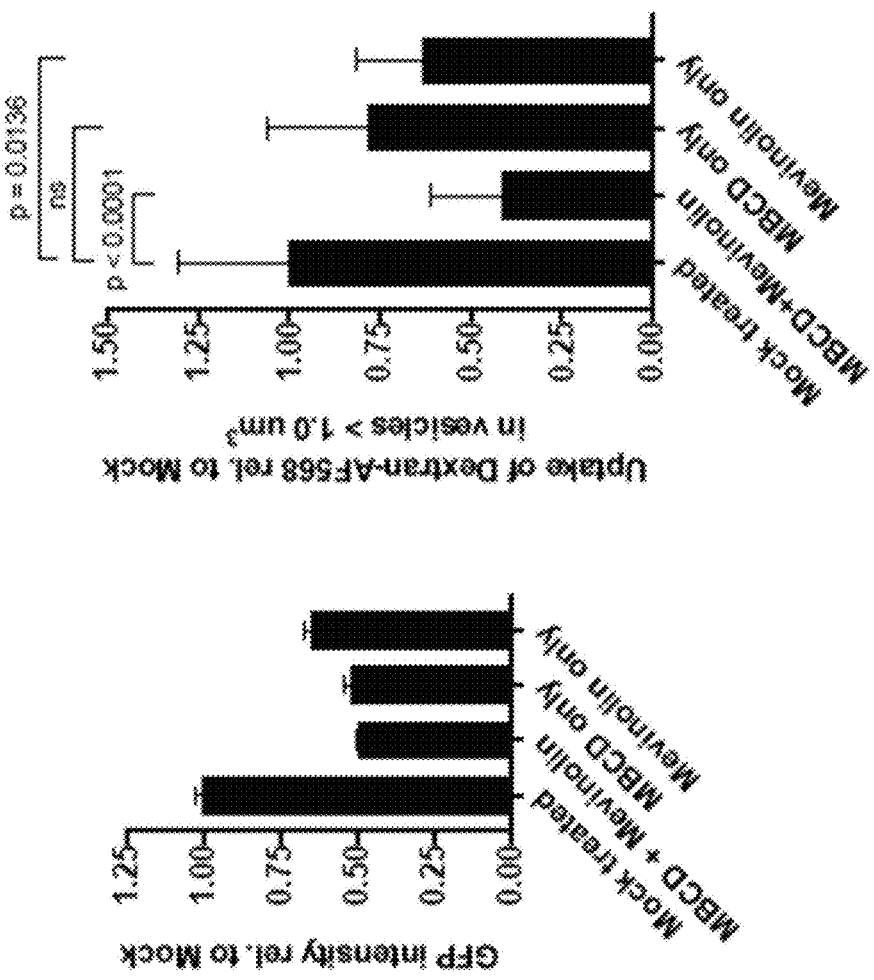
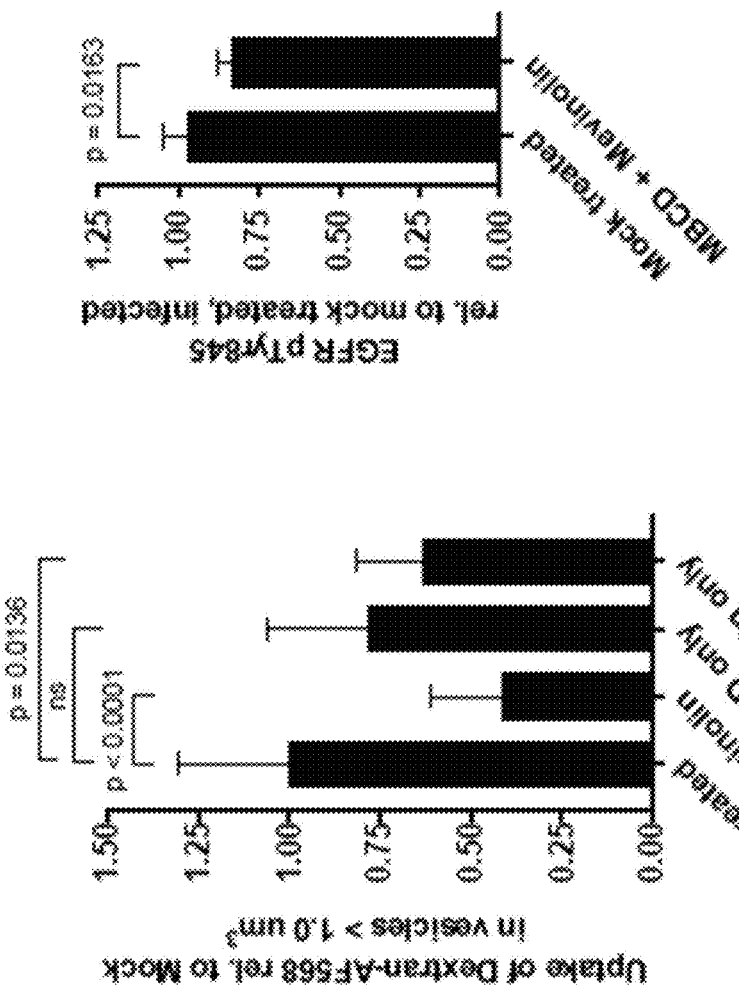
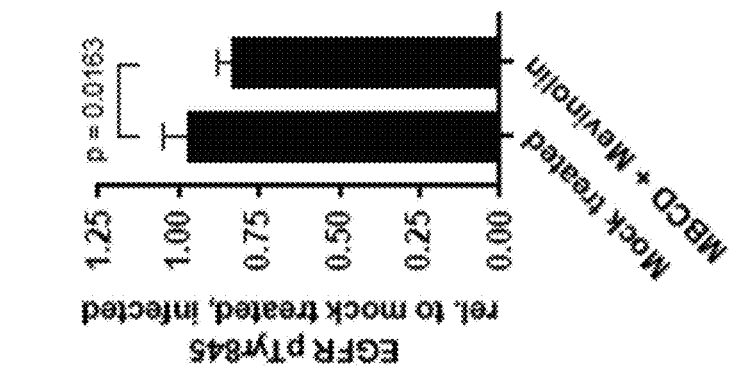
FIG. 10A
FIG. 10B
FIG. 10C

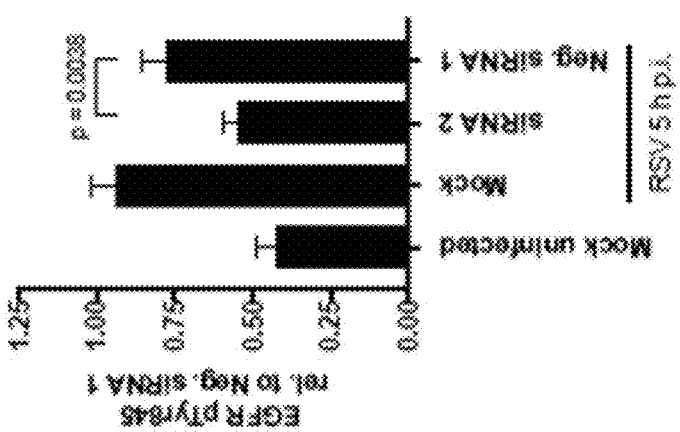
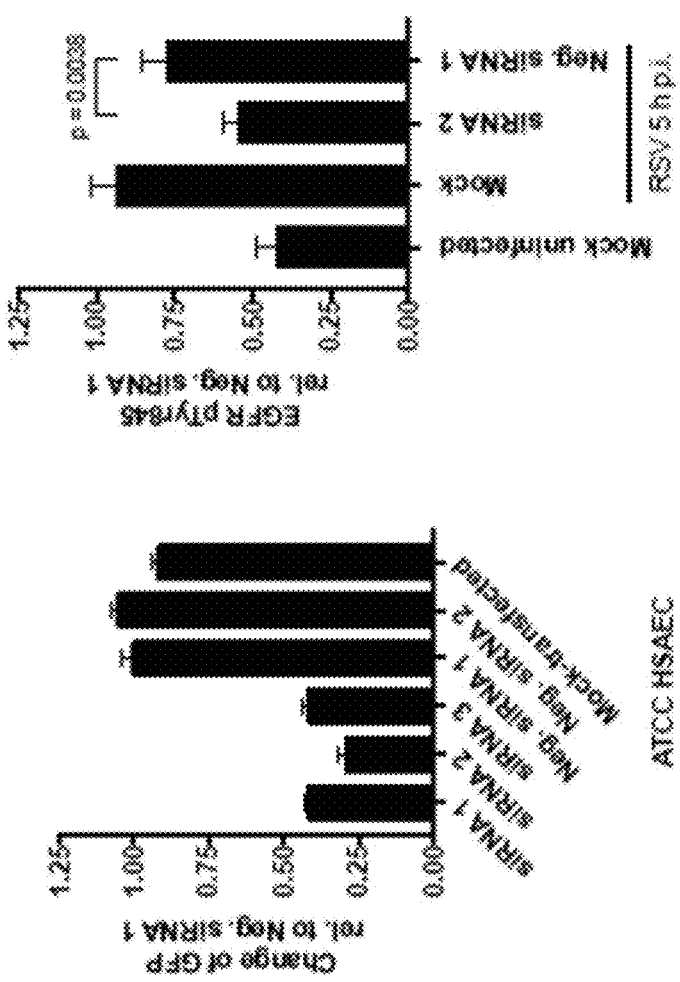
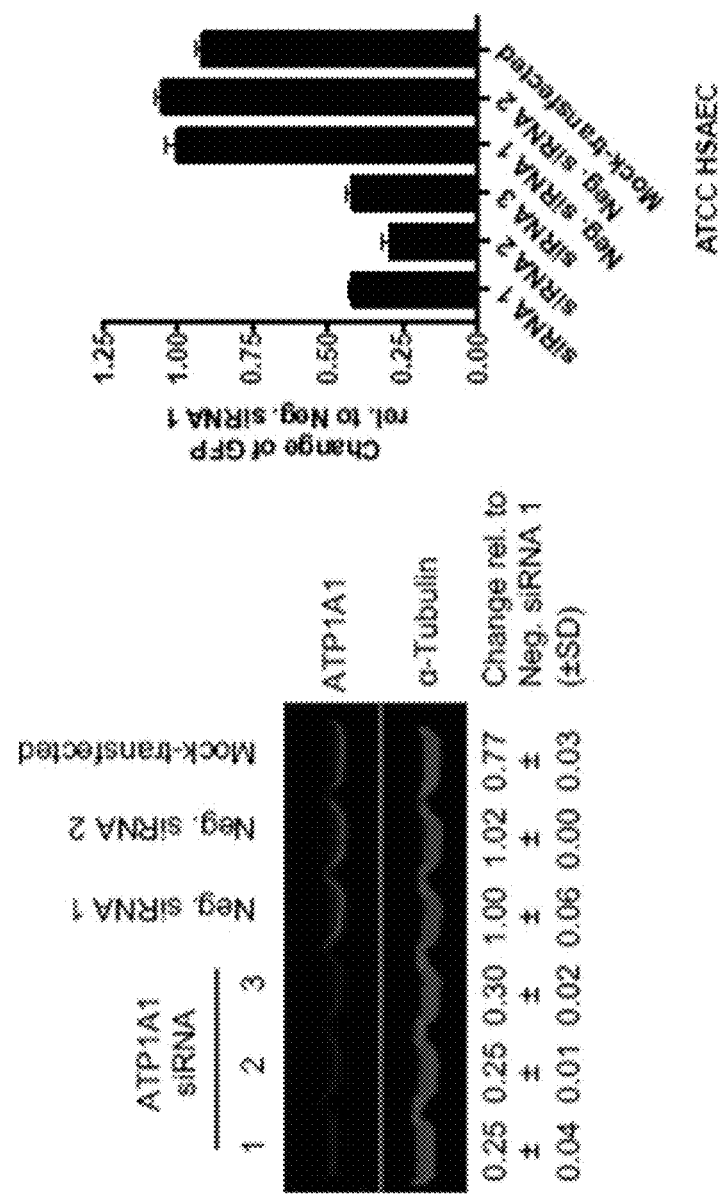

IC$_{50}$ concentration of Ouabain and PST2238 for RSV-GFP infection of HSAEC and A549 cells:

|       | Ouabain [nM] | PST2238 [µM] |
|-------|--------------|--------------|
| A549  | 12.7         | 14.8         |
| HSAEC | 2.6          | 1.8          |

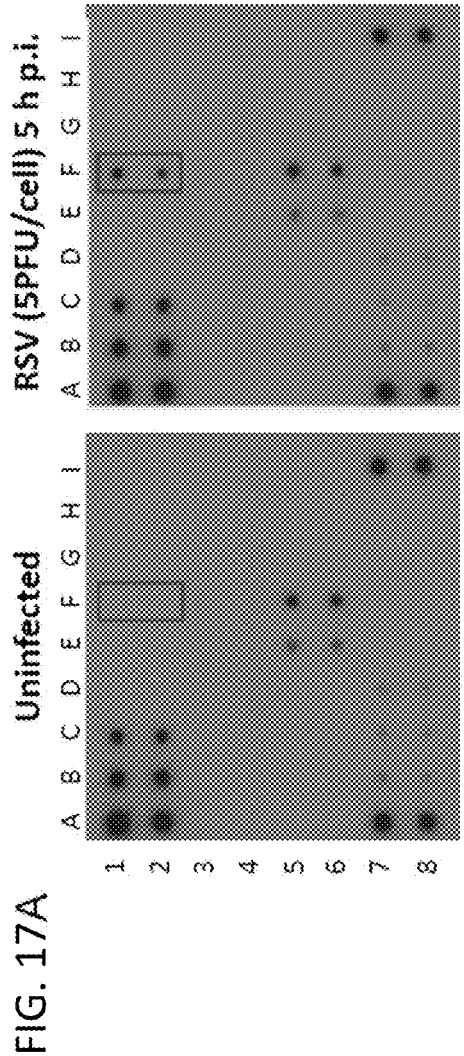

| | A | B | C | D | E | F | G | H | I |
|---|---|---|---|---|---|---|---|---|---|
| 1 | P1 | P2 | P3 | Blank | Neg | EGFR (Tyr845) | EGFR (Tyr992) | EGFR (Tyr1045) | EGFR (Tyr1068) |
| 2 | P1 | P2 | P3 | Blank | Neg | EGFR (Tyr845) | EGFR (Tyr992) | EGFR (Tyr1045) | EGFR (Tyr1068) |
| 3 | Blank | Blank | Blank | Blank | EGFR (Tyr1086) | EGFR (Tyr1148) | EGFR (Tyr1173) | EGFR (Ser1046/1047) | EGFR (Ser1070) |
| 4 | Blank | Blank | Blank | Blank | EGFR (Tyr1086) | EGFR (Tyr1148) | EGFR (Tyr1173) | EGFR (Ser1046/1047) | EGFR (Ser1070) |
| 5 | ErbB2 (Tyr877) | ErbB2 (Tyr1112) | ErbB2 (Tyr1221/1222) | ErbB2 (Tyr1248) | ErbB2 (Thr686) | ErbB2 (Ser1113) | ErbB3 (Tyr1289) | ErbB4 (Tyr1284) | Blank |
| 6 | ErbB2 (Tyr877) | ErbB2 (Tyr1112) | ErbB2 (Tyr1221/1222) | ErbB2 (Tyr1248) | ErbB2 (Thr686) | ErbB2 (Ser1113) | ErbB3 (Tyr1289) | ErbB4 (Tyr1284) | Blank |
| 7 | EGFR | ErbB2 | ErbB3 | ErbB4 | Blank | Blank | Neg | Blank | P4 |
| 8 | EGFR | ErbB2 | ErbB3 | ErbB4 | Blank | Blank | Neg | Blank | P4 |

P1 - P4: Array internal positive control, decreasing intensity
Neg: Array internal negative control

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: inhibitory nucleic acid molecule

<400> SEQUENCE: 1
cccggaaaga ctgaaagaat a                                              21

<210> SEQ ID NO 2
<211> LENGTH: 21
<212> TYPE: DNA
<213> ORGANISM: Artificial Sequence
<220> FEATURE:
<223> OTHER INFORMATION: inhibitory nucleic acid molecule

<400> SEQUENCE: 2
cttgatgaac ttcatcgtaa a                                              21

<210> SEQ ID NO 3

```
<211> LENGTH: 18
<212> TYPE: DNA
<213> ORGANISM: Artificial Sequence
<220> FEATURE:
<223> OTHER INFORMATION: inhibitory nucleic acid molecule

<400> SEQUENCE: 3
catgaagctg atacgaca                                                       18

<210> SEQ ID NO 4
<211> LENGTH: 18
<212> TYPE: DNA
<213> ORGANISM: Artificial Sequence
<220> FEATURE:
<223> OTHER INFORMATION: inhibitory nucleic acid molecule

<400> SEQUENCE: 4
aggaaatatg tactacga                                                       18

<210> SEQ ID NO 5
<211> LENGTH: 21
<212> TYPE: DNA
<213> ORGANISM: Artificial Sequence
<220> FEATURE:
<223> OTHER INFORMATION: inhibitory nucleic acid molecule

<400> SEQUENCE: 5
aattctccga acgtgtcacg t                                                   21
```

USE OF OUABAIN ANTAGONISTS TO INHIBIT VIRAL INFECTION

CROSS REFERENCE TO RELATED APPLICATIONS

This application claims priority to U.S. Provisional Application No. 62/737,899, filed Sep. 27, 2018, which is incorporated by reference in its entirety.

FIELD OF THE DISCLOSURE

The present disclosure relates to use of ouabain antagonists to inhibit a viral infection in a subject, such as a Respiratory Syncytial Virus infection.

BACKGROUND

Viral infection and the resulting infectious disease burden impart a substantial impact in health and productivity. Among viruses, the human respiratory syncytial virus (RSV) is the leading viral cause of acute pediatric lower respiratory tract infections worldwide, with no available vaccine or effective antiviral drug. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite repeated efforts, a need remains for therapeutic for treating RSV infection.

SUMMARY

This disclosure provides novel methods of inhibiting and treating viral infection in a subject, such as RSV infection in a subject.

In some embodiments, the method comprises administering a therapeutically effective amount of an agent to the subject to inhibit the viral infection, wherein the agent is a competitive antagonist of ouabain binding to ATPase Sodium/potassium-transporting subunit alpha-1 (ATP1A1) (such as PST2238). In some embodiments, the method comprises selecting a subject with or at risk of the viral infection for administration of the agent.

In some embodiments, the viral infection is an infection with a negative-sense single-stranded RNA virus, a virus of the Pneumoviridae family, and/or a virus that utilizes ATP1A1 signaling for cellular entry.

In some embodiments, viral infection is an infection with RSV. Infections by other viruses can also be inhibited using the methods provided herein, including infection with any one of Adenovirus, Clade A New World arenavirus Pichindé, African swine fever virus, Hepatitis C virus, Hepatitis B virus, Human cytomegalovirus, Herpes simplex virus, Epstein-Barr virus, Influenza A virus, Human papillomavirus, Human parainfluenza virus Type 1-3, Adeno-associated virus, Enterovirus 71, Rhinovirus, Vaccinia virus, Cowpox virus, Western Reserve, International Health Department-J, Shope fibroma virus, Human immunodeficiency virus, Avian erythroblastosis virus, Mouse Cas NS-1 retrovirus; influenza virus, Herpes simplex virus, Chikungunya virus, Human immunodeficiency virus type 1, Adenovirus, Porcine reproductive, respiratory syndrome virus 1, Ebola virus, Coronavirus, Hepatitis C virus, Lymphocytic choriomeningitis virus, Lassa virus, or Junin virus.

The agent can be administered to the subject using any suitable method, such as oral, intranasal, or inhalation, administration.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1D. ATP1A1 knock down by siRNA transfection. A549 cells were transfected with three different siRNAs (siRNA 1-3) targeting the ATP1A1 mRNA. Cells were harvested 24, 48 and 72 h post transfection (p.t.) and the ATP1A1 transcript and protein levels were quantified. As negative control, cells were transfected with two different negative siRNAs (Neg. siRNA 1, 2) with no known target in human cells. (FIG. 1A) Relative quantification of ATP1A1 mRNA. Total RNA was isolated and was reverse transcribed with oligo(dT)$_{12-18}$ primers to favor reverse transcription of mRNA. The amount of ATP1A1 mRNA was quantified by an ATP1A1 mRNA specific TaqMan Assay, values were normalized to 18S rRNA and reported as fold-change relative to Neg. siRNA 1. Data are shown as mean fold change relative to Neg. siRNA 1 with error bars indicating the standard deviation of three independent experiments with three replicate reactions for each time point. (FIG. 1B) ATP1A1 protein level. Transfected A549 cells were lysed in 1×LDS buffer at different time points (24, 48 and 72 h p.t.) and the ATP1A1 protein level was quantified by Western blotting with a rabbit anti-ATP1A1 antibody and a corresponding infrared dye 680RD conjugated goat anti-rabbit secondary antibody. Alpha-tubulin was used as a loading control and was detected by a mouse anti-tubulin antibody and an infrared dye 800CW conjugated goat anti-mouse secondary antibody. One representative blot of ATP1A1 and its corresponding alpha-tubulin blot is shown. (FIG. 1C) Quantification of ATP1A1 protein level. The protein levels of three independent experiments, as described above, were quantified, normalized to alpha-tubulin, and reported as fold-change relative to Neg. siRNA 1 with error bars indicating the standard deviation. (FIG. 1D) Cell viability. An ATP based cell viability assay [CELLTITER GLO® (PROMEGA®)] was performed 72 h p.t. to evaluate the viability of the transfected cells. Cells were lysed, the ATP concentration was determined by ATP dependent luciferase activity, which was detected with an ELISA reader, and the viability was reported relative to mock-transfected cells.

(FIG. 2C). Single, live, uninfected cells are shown in the histogram as reference. The RSV plaque forming unit (PFU) titer was determined by plaque titration on Vero cells 24 h p.i. (FIG. 2D). All data are derived from at least three independent experiments and shown as mean values with error bars indicating the standard deviation. The statistical significance of difference was determined by one-way analysis of variance with Dunnett's multiple comparison post-test and p-values are shown for each comparison.

(FIG. 3A) A549 cells were inoculated with wt RSV (MOI=5 PFU/cell) and incubated for 2 or 5 h at 37° C. Cells were fixed with 4% PFA, permeabilized with 0.1% TRITON™ X100 and stained for ATP1A1 (green) with a rabbit anti-ATP1A1 antibody (ab76020) and Alexa Fluor 488 conjugated donkey anti-rabbit secondary antibody. RSV F (red) was detected by a mouse monoclonal anti-RSV F antibody (1129) and an Alexa Fluor 594 conjugated anti-mouse secondary antibody. The cell nuclei were stained with DAPI and are shown in all channels. Images (z-stacks) were acquired on a Leica SP5 confocal microscope, with a 63× objective (NA 1.4) and a zoom of 3.0. Arrows are indicating co-localization of ATP1A1 and RSV F. Scale bar 10 µm. (FIG. 3B) Cross section of the marked area of the RSV 5 h p.i. image of FIG. 3A. Scale bare 10 µm.

FIGS. 5A-5G. Effect of ouabain and rostafuroxin (PST2238) on RSV infection. (FIG. 5A) Uninfected A549 cells were treated for 24 h with either 25 nM ouabain or 20 µM rostafuroxin (PST2238) and subjected to an immunofluorescence staining. ATP1A1 (green) and EGFR (red) were stained by the primary antibodies rabbit anti-ATP1A1 (ab76020) and rat anti-EGFR (ab231) and the corresponding secondary antibodies anti-rabbit Alexa 488 and anti-rat Alexa 647, respectively. Scale bar 10 µm. (FIGS. 5B and 5C) A549 cells pre-treated overnight with either 25 nM ouabain or 20 µM PST2238 in complete media were inoculated with RSV-GFP (MOI=1 PFU/cell). Cells were incubated at 37° C. for 17 h and infectivity is shown in FIG. 5B. GFP signal of the total well (area scan by ELISA reader) and reported as fold change relative to mock-treated infected cells. FIG. 5C. Virus titer was determined by plaque titration on Vero cells 24 h p.i. (FIGS. 5D-5G) 25 nM ouabain or 20 µM PST2238 was added to A549 cells infected with RSV-GFP (MOI=3 PFU/cell) at different time points post infection. GFP intensity, as an indicator of infection, was quantified by flow cytometry. The histogram shows the GFP intensity of live, single, infected cells analyzed at 24 h p.i. with different time points of addition of ouabain (FIG. 5D) or PST2238 (FIG. 5F). The MFI of GFP positive cells was quantified and expressed as value relative to mock-treated, RSV-infected cells depending on the time of addition of ouabain (FIG. 5E) or PST2238 (FIG. 5G).

(FIG. 6A) GFP intensity was measured on ELISA reader 17 h p.i. and expressed as fold change relative to mock-treated cells that were infected. (FIG. 6B) RSV titers were determined by plaque titration on Vero cells 24 h p.i. The statistical significance of the difference was determined by one-way analysis of variance with Tukey's multiple-comparison post-test and p-values are shown for each comparison.

FIGS. 7A-7D. Effect of EGFR knock down on RSV infection. (FIG. 7A) A549 cells had been transfected with ATP1A1, EGFR or negative siRNA and subjected to an immunofluorescence staining for ATP1A1 (green) and EGFR (red) 48 h post siRNA transfection as described for FIG. 5A. Images (z-stacks) were acquired on a Leica SP5 confocal microscope with 63× objective NA 1.4 and 2.0× zoom. Scale bar 10 µm. (FIGS. 7B and 7C) A549 cells that had been transfected with an EGFR siRNA or Neg. siRNA 1 or 2 were infected with RSV-GFP (MOI=1 PFU/cell) at 48 h p.t. Infection was quantified by GFP signal (FIG. 7B) of the total well (area scan by ELISA reader) at 17 h p.i. and by plaque titration (FIG. 7C) on Vero cells 24 h p.i. Data are derived from three independent experiments. The statistical significance of the difference was determined by one-way analysis of variance with Tukey's multiple-comparison post-test and p-values of the significance for each comparison is indicated. (FIG. 7D) An ATP based cell viability assay [CELLTITER-GLO® (PROMEGA®)] was performed 72 h p.t. to evaluate the viability of the transfected cells. Cells were lysed, the ATP concentration was determined by luciferase activation and the viability was reported relative to mock-transfected cells based on the reduction of ATP.

(FIG. 8A) Representative array spots of pTyr845 EGFR and its corresponding pan EGFR for each treatment are shown. (FIGS. 8B and 8C) pTyr845 EGFR signals of three independent experiments with two technical replicates each were normalized to the signal of the internal positive controls and pan EGFR. Signals are reported as fold-change relative to the average signal of mock-treated, RSV infected samples. FIG. 8B shows the siRNA knock down samples and pTyr845 EGFR levels were reported relative to Neg. siRNA 1. FIG. 8C shows the chemical compound treated samples and pTyr845 EGFR levels were reported relative to mock-treated, infected samples. (FIG. 8D) As control, PST2238 or Ouabain pretreated A549 cells were stimulated with EGF (100 ng/ml) for 45 min and the pTyr845 EGFR signal was quantified. The statistical significance of the differences were determined by one-way analysis of variance with Dunnett multiple-comparison test and the significance p-values are indicated for each comparison.

FIGS. 9A-9F. RSV enters the cell by ATP1A1 dependent macropinocytic uptake that can be blocked by ouabain or PST2238. (FIG. 9A) A549 cells were serum starved overnight and either mock-infected or infected with wt RSV (MOI=5 PFU/cell) in media containing Alexa Fluor 568 conjugated Dextran (10.000 MW, Dextran-AF568). Cells were fixed with 4% PFA 5 h p.i., nuclei were counterstained with DAPI, and imaged on a Leica SP5 confocal microscope with a 40× Objective NA 1.3 and 2.0× zoom. (FIG. 9B)

Co-localization of ATP1A1 (green channel) RSV-N (red channel) and Dextran-Alexa Fluor 568 (cyan channel) in RSV infected (MOI=5 PFU/cell) A549 cells at 5 h p.i. Cells were infected as described above and fixed with 4% PFA 5 h p.i. Fixed cells were permeabilized with 0.1% TRITON™ X100 and subjected to an immunofluorescence staining with rabbit anti-ATP1A1 (ab76020) and mouse anti-RSV-N (ab94806) primary antibodies, followed by Alexa Fluor 488 conjugated goat anti-rabbit and Alexa Fluor 647 conjugated goat anti-mouse secondary antibodies. Z-stacks were acquired on Leica SP8 confocal microscope with 63× objective, NA 1.4 and 3× zoom. Arrows indicate co-localization of ATP1A and RSV N in Dextran-AF568 positive vesicles. (FIG. 9C) Co-localization of RSV F (green) and RSV N (red) with Dextran-Alexa Fluor 568 (cyan) in RSV infected (MOI=5 PFU/cell) A549 cells at 5 h p.i. Cells were stained as described above for FIG. 9B. RSV F was detected with an Alexa Fluor 488 conjugated mouse monoclonal anti-RSV F antibody (1129). RSV N was detected with an allophycocyanin (APC) conjugated mouse monoclonal anti-RSV N antibody (Novus Biologicals, LLC). Image acquisition and analysis were performed as described above for FIG. 9B. Arrows indicate co-localization of RSV F and RSV N in dextran-AF568 positive vesicles. All scale bars are 10 µm. (FIGS. 9D-9F) Quantification of Dextran-AF568 uptake during RSV infection. FIG. 9D, A549 cells were transfected with ATP1A1 siRNA2 (showed strongest effect in all other assays) or Neg. siRNA 1 and 48 h p.t. cells were inoculated with wt RSV in Dextran-AF568 containing media. FIG. 9E, A549 cells were pre-treated with ouabain or PST2238 overnight and inoculated with wt RSV in Dextran-AF568 containing media. FIG. 9F, Untreated A549 cells were infected with wt RSV or rgRSV dSHdG in Dextran-AF568 containing media. For all treatments (FIGS. 9D-9F) cells were fixed 5 h p.i., counterstained with DAPI and z-stacks were acquired on a Leica SP8 confocal microscope with 63× objective NA 1.4, 1.0× zoom. For each treatment, the uptake of Dextran-AF568 in vesicles greater than 1.0 µm$^3$ was quantified as described in detail in the Method section. Mean values are reported relative to RSV infected cells transfected with Neg. siRNA 1 (FIG. 9D), Mock treated, infected cells (FIG. 9E) or wt RSV infected cells (FIG. 9F). Error bars indicating the standard deviation of at least three independent experiments. The statistical significance of difference was determined for (FIG. 9D) and (FIG. 9E) by one-way analysis of variance with Tukey's multiple comparison post-test and for (FIG. 9F) by two-tailed unpaired t-test. P-values are shown for each comparison.

FIGS. 10A-10C. Effect of cholesterol depletion on RSV infection. A549 cells were cholesterol depleted by treatment with methyl-beta-cyclodextrin (MBCD) and Mevinolin or each chemical separately. MBCD removes cholesterol from the plasma membrane and Mevinolin inhibits cholesterol biosynthesis. (FIG. 10A) RSV infection assay of cholesterol depleted A549 cells. A549 cells were pre-treated for 5 h with the indicated cholesterol depleting compounds and infected with RSV-GFP (MOI=1 PFU/cell) while the cholesterol depleting compounds were present. Viral GFP expression was quantified 17 h p.i. and reported as fold change relative to mock-treated infected cells. (FIG. 10B) Quantification of macropinocytosis in cholesterol depleted RSV infected A549 cells. A549 cells were pre-treated overnight with the indicated cholesterol depleting compounds and infected with RSV (MOI=5 PFU/cell) in the presence of Alexa Fluor 568 conjugated Dextran (Dextran-AF568) and incubated at 37° C. and 5% $CO_2$. 5 h p.i the cells were fixed with 5% PFA and nuclei were counterstained with DAPI. The total intensity of Dextran-AF568 uptake in vesicles larger than 1.0 µm$^3$ was quantified, as described in detail in the methods section, and reported as fold change relative to mock-treated infected cells. The statistical significance of the differences was determined by one-way analysis of variance with Tukey's multiple-comparison post-test and the significance p-values are indicated for each comparison. (FIG. 10C) EGFR Tyr845 phosphorylation in cholesterol depleted cells. A549 cells were treated with MBCD and Mevinolin overnight to deplete cholesterol from the plasma membrane. Cells were infected with wt RSV (MOI=5 PFU/cell) and the phosphorylation of EGFR Tyr845 was quantified by an EGFR phosphorylation antibody array (RayBiotech), as described in the methods section. The level of pTyr845 was reported relative to mock-treated and infected cells. The statistical significance of difference was determined by a two-tailed unpaired t-test.

FIGS. 11A-11E. Confirmation of the role of ATP1A1 in RSV entry using primary human small airway epithelial cells (HSAEC). The results obtained in A549 cells were validated in human small airway epithelial cells (HSAEC). The experiments were performed in a similar manner as described for A549 cells in the methods section and the corresponding Figure legends. (FIG. 11A) siRNA knock down validation in HSAEC. (FIG. 11B) Efficiency of RSV infection (GFP quantification by ELISA reader) in ATP1A1 siRNA knock down HSAEC cells. (FIG. 11C) EGFR Tyr845 phosphorylation in ATP1A1 siRNA 2 knock down HSAEC cells. (FIG. 11D) Inhibition of RSV infection in ouabain and PST2238 treated HSAEC cells infected with RSV-GFP. The determined $IC_{50}$ values of ouabain and PST2238 for inhibiting RSV infection were 5- and 8-fold lower than for A549 cells, respectively. (FIG. 11E) ATP1A1 clustering and colocalization with RSV-N in HSAEC cells. Scale bar 10 µm.

FIGS. 17A and 17B. (FIG. 17A) A representative image of the EGFR phosphorylation-specific antibody array probed with uninfected or RSV infected A549 cell lysates as indicated. Array was performed as described in the methods section. (FIG. 17B) Layout of the EGFR phospho-specific antibodies and the control spots on the array (RayBiotech). Each antibody is present in duplicate on each membrane.

SEQUENCE LISTING

Figure 1D:
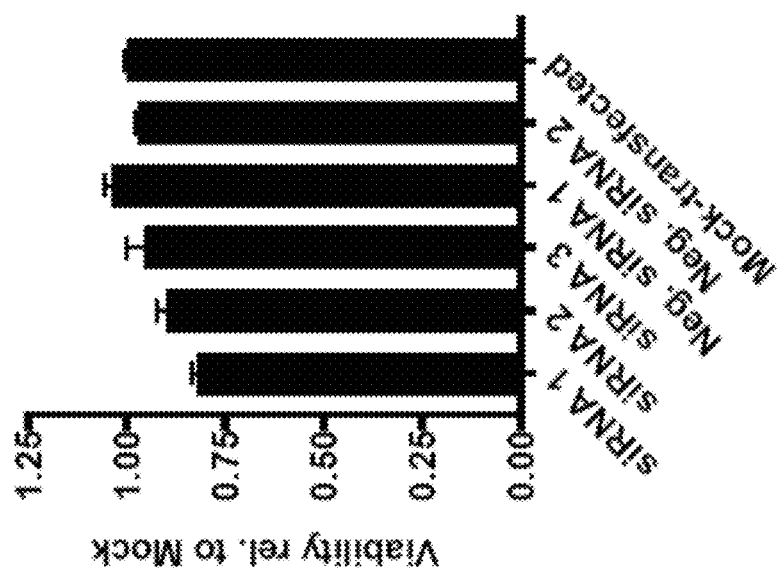

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~4 kb), which was created on Sep. 24, 2019, which is incorporated by reference herein.

DETAILED DESCRIPTION

As disclosed herein, ATP1A1 is a host protein involved with cellular entry of RSV. RSV entry requires activation of a signaling cascade mediated by ATP1A1 which resembles the signaling pathway (also mediated by ATP1A1) triggered by cardiotonic steroids. As described in the examples, RSV infection triggers ATP1A1 activation which signals via activated Src, the non-receptor tyrosine kinase, to transactivate the epidermal growth factor receptor. Epidermal growth factor receptor tyrosine phosphorylation and downstream signaling result in the induction of macropinocytosis (the formation of large fluid filled endocytic vesicles at the plasma membrane). The macropinocytic vesicles engulf RSV at the cell membrane and transport RSV into the cell.

Prior studies have shown that cardiotonic steroids such as ouabain, which specifically bind and activate ATP1A1 signaling, inhibit infection and cell entry of RSV and many other types of viruses.

However, described herein is the novel finding that administration to a subject of a competitive antagonist of ouabain binding to ATP1A1 substantially inhibits RSV infection in the subject. This result is particularly unexpected given the findings discussed above, showing that ATP1A1 agonists such as ouabain also inhibit viral infection.

I. Summary of Terms

Unless otherwise noted, technical terms are used according to conventional usage. Definitions of many common terms in molecular biology may be found in Krebs et al. (eds.), Lewin's genes XII, published by Jones & Bartlett Learning, 2017.

The singular terms "a", "an", and "the" include plural referents unless context clearly indicates otherwise. The term "comprises" means "includes." Although methods and materials similar or equivalent to those described herein can be used in the practice or testing of the present disclosure, suitable methods and materials are described below. It is further to be understood that any and all base sizes or amino acid sizes, and all molecular weight or molecular mass values, given for nucleic acids or polypeptides are approximate, and are provided for descriptive purposes, unless otherwise indicated. In case of conflict, the present specification, including terms, will control. In addition, the materials, methods, and examples are illustrative only and not intended to be limiting. In order to facilitate review of the various embodiments of the disclosure, the following explanation of terms is provided:

About: With reference to a numerical parameter, the term "about" refers to a plus or minus 5% range around the numerical parameter. For example, "about 5%" refers to "4.75% to 5.25%."

Administration: To provide or give to a subject an agent, for example, PST2238, by any effective route. Administration can be local or systemic. Exemplary routes of administration include, but are not limited to, oral (for example, oral administration of a composition comprising PST2238 that delays release of the PST2238 until the composition is in the intestine, such as the colon), injection (such as subcutaneous, intramuscular, intradermal, intraperitoneal, intravenous, direct injection into intestine (for example, injection into the colon)), sublingual, rectal, transdermal (for example, topical), intranasal, vaginal, and inhalation (particularly in the case of a treatment for RSV infection) routes.

Agent: Any substance or any combination of substances that is useful for achieving an end or result; for example, a substance or combination of substances useful for inhibiting RSV infection in a subject. Agents include proteins, antibodies, nucleic acid molecules, compounds, small molecules, organic compounds, inorganic compounds, or other molecules of interest. An agent can include a therapeutic agent, a diagnostic agent or a pharmaceutical agent. Agents include effector molecules and detectable markers. The skilled artisan will understand that particular agents may be useful to achieve more than one result.

Agonist: An agent that binds to a receptor and initiates an action by the receptor. For example, an agonist that binds to a cellular receptor initiates a physiological or pharmacological response characteristic of that receptor.

Antagonist: An agent that inhibits an action by a receptor. For example, an antagonist that binds to a cellular receptor inhibits a physiological or pharmacological response characteristic of that receptor.

ATP1A1: Also known as ATPase Na+/K+ transporting subunit alpha 1, ATP1A1 is the α-subunit of the $Na^+K^+$ ATPase complex, which contains in addition a β-subunit, and usually also a γ-subunit (also known as the FXYD subunit) (Reinhard et al., *Cell Mol Life Sciences*: CMLS. 2013; 70(2):205-22; Morth et al., *Nat Rev Mol Cell Biol.* 2011; 12(1):60-70). ATP1A1 is the major subunit and contains ten transmembrane helices that embed the protein complex in the plasma membrane and form the ion channel. The β and FXYD subunits are important for the transport properties of the $Na^+K^+$ ATPase and also stabilize the complex (Geering. *Curr Opin Nephrol Hypertens.* 2008; 17(5):526-32). Humans express three additional alpha-isoforms besides ATP1A1 (ATP1A2, ATP1A3, and ATP1A4). The expression profile of the four isoforms is cell type dependent, with the ATP1A1 being expressed ubiquitously and being the predominant isoform expressed in A549 cells (Liu et al., *PloS One.* 2016; 11(7):e0159789).

$Na^+K^+$ ATPase complexes present in the plasma membrane play a major role in ion transport, maintaining electrolyte and fluid balance. In addition, a subpopulation of $Na^+K^+$ ATPase is localized in caveolae (Ostrom et al., *J Biol Chem.* 2001; 276(45):42063-9; Conner et al., *Nature.* 2003; 422(6927):37-44), and this subpopulation uniquely can engage in signal transduction, via the ATP1A1 subunit (Reinhard et al., *Cell Mol Life Sciences*: CMLS. 2013; 70(2):205-22; Xie et al., *Mol Interv.* 2003; 3(3):157-68; Wang et al., *J Biol Chem.* 2004; 279(17):17250-9; Liu et al., *Am J Physiol Cell Physiol.* 2003; 284(6):C1550-60. $Na^+K^+$ ATPase, bearing the ATP1A1 subunit, has been well-characterized as the sole receptor for cardiotonic steroids such as ouabain, which are agonists that initiate ATP1A1-based signaling.

As disclosed herein, ATP1A1 is a host protein involved with cellular entry of RSV.

In humans, ATP1A1 protein is expressed from the ATP1A1 gene (NCBI Gene ID No, 476). The human protein sequence is set forth as NCBI Ref. No. NP_000692.2.

Methods of identifying an agent that modulates ATP1A1 activity are known, for example, as described in the Examples.

Competitive antagonist: An agent that binds to a receptor and blocks an action by the receptor in response to an agonist. Sufficient concentrations of the competitive antagonist displace the agonist from the receptor binding site, resulting in a lower frequency of receptor activation. The level of activity of the receptor depends on the relative affinity of each molecule (competitive antagonist and agonist) for the binding site on the receptor and their relative concentrations.

Competitive antagonist of ouabain binding to ATP1A1: An agent that binds to ATP1A1 and competitively blocks ouabain binding to ATP1A1 without activating ATP1A1. PST2238 is an example of a competitive antagonist of ouabain binding to ATP1A1. Methods of identifying an agent that is a competitive antagonist of ouabain binding to ATP1A1 are known, for example, as described in the examples and Ferrari et al. (*J Pharmacol Exp Ther.* 1998; 285(1):83-94).

Control: A sample or standard used for comparison with an experimental sample. In some embodiments, the control is a negative control sample obtained from a healthy patient. In other embodiments, the control is a positive control sample obtained from a patient diagnosed with a viral infection, such as an RSV infection. In still other embodiments, the control is a historical control or standard reference value or range of values (such as a previously tested control sample, such as a group of infected patients with known prognosis or outcome, or group of samples that represent baseline or normal values).

Detecting: To identify the existence, presence, or fact of something. General methods of detecting are known to the skilled artisan and may be supplemented with the protocols and reagents disclosed herein. In some examples, detecting an RSV nucleic acid in a biological sample detects RSV infection in the subject from whom the biological sample was obtained. Detection can include a physical readout, such as fluorescence or a reaction output.

Inhibiting or treating a disease or condition: Inhibiting the full development of a disease or condition, for example, in a subject who is at risk of or has a viral infection, such as an RSV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in viral titer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Ouabain: A designation for (1β,3β,5β,11α)-3-[(6-Deoxy-α-L-mannopyranosyl)oxy]-1,5,11,14,19-pentahydroxycard-20(22)-enolide (PubChem CID: 439501), which has the following structural formula:

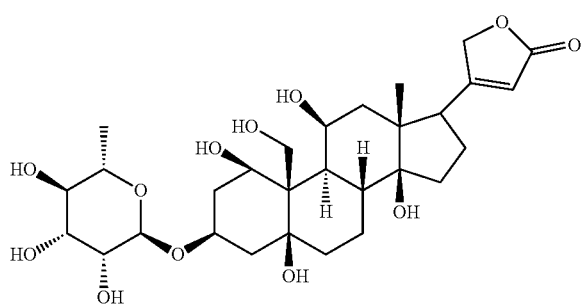

Ouabain is a cardiotonic steroid that specifically binds to and activates ATP1A1 to regulate its signaling and ion exchange function, leading to an increase in blood pressure. Cardiotonic steroids are a large family of clinically relevant specific inhibitors of the $Na^+/K^+$-ATPase, used classically to treat heart failure. Ouabain is available commercially from multiple sources, for example, from Sigma-Aldrich, St. Louis, Mo.

Pharmaceutically acceptable carriers: The pharmaceutically acceptable carriers of use are conventional. *Remington: The Science and Practice of Pharmacy*, $22^{nd}$ ed., London, UK: Pharmaceutical Press, 2013, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

PST2238: A designation for (3β,5β,14β)-21,23-Epoxy-24-norchola-20,22-diene-3,14,17-triol (PubChem CID: 153976), which has the following structural formula:

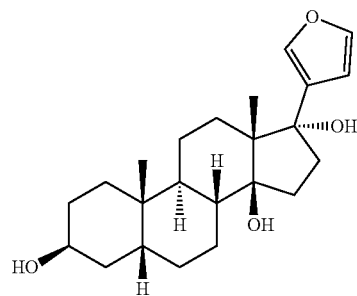

PST2238 is also known as Rostafuroxin. PST2238 is a digitoxigenin derivative that specifically binds to ATP1A1 and competitively displaces ouabain binding from ATP1A1. Clinical studies have shown that PST2238 lowers the blood pressure in adducin- and ouabain-induced forms of hypertension without lowering the normal systolic blood pressure of healthy individuals. PST2238 has been shown to be non-toxic in human and animal models (see, e.g., Ferrari et al., Cardiovascular Drug Reviews, 17(1): 39-57, 1999, and Ferrari et al., Am J Physiol Regul Integr Comp Physiol, 290(3): R529-535, 2006), including at dosages of 5 mg twice a day for a week and at 0.5 mg per day for three months (see Ferrari et al., Am J Physiol Regul Integr Comp Physiol, 290(3): R529-535, 2006). PST2238 is available commercially from multiple sources, for example, from Sigma-Aldrich, St. Louis, Mo.

Respiratory Syncytial Virus (RSV): An enveloped non-segmented negative-sense single-stranded RNA virus of the family Pneumoviridae within the order Mononegavirales. The genome is approximately 15.2 kb long and contains 10 genes that encode 11 proteins, namely (in 3' to 5' genomic order) the nonstructural proteins NS1 and NS2; nucleocapsid (N); phosphoprotein (P); matrix protein (M); the small hydrophobic (SH), attachment (G), and fusion (F) glycoproteins; the M2-1 and M2-2 proteins that are encoded by the two overlapping open reading frames in the M2 gene; and the large polymerase L. The RSV envelope glycoproteins G and F mediate viral attachment and fusion, respectively, for entry into the host cell, while SH forms ion channels whose role in infection remains unclear. SH and G are not essential for virus replication in immortalized cell lines, but G is important for efficient replication in vivo. The G protein contains a highly basic heparin binding domain and a CX3C motif which mediate cell attachment by binding to the cell surface glycosaminoglycans (GAGs) and the CX3CR1 chemokine receptor, respectively. The RSV F protein mediates viral entry, which involves fusion of the viral envelope with the plasma membrane or with the membranes of intracellular vesicles, as described below.

Two antigenic subgroups of human RSV strains have been described, the A and B subgroups, based primarily on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J, Physiol. Lung Cell Mol. Physiol.*, 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

Symptoms of RSV infection include bronchiolitis, cough, wheezing, rales (crackling in the lungs), low grade fever (38.3° C.), decreased oral intake and in more advanced cases of infection cyanosis can occur with up to 20% of patients developing an elevated temperature. In a given year, it is estimated that in the United States alone, 4-5 million children under the age of 4 years will develop an acute RSV infection and more than 125,000 infants are hospitalized with an RSV related illness. Between 25-40% of infants with RSV infections will show signs of pneumonia and bronchiolitis. The risk and severity of RSV infections is increased in infants with, for example, chronic co-existing medical conditions such as chronic lung disease, congenital heart disease, those who have been born prematurely and those with immunodeficiency.

Small molecule: A compound, typically with a molecular weight less than 1000, or in some embodiments, less than about 500 Daltons.

Subject: Any mammal, such as humans, non-human primates, pigs, sheep, cows, rodents, and the like. In two non-limiting examples, a subject is a human subject or a bovine subject. Thus, the term "subject" includes both human and veterinary subjects. In an additional example, a subject is selected that is in need of inhibiting of a viral infection, such as an RSV infection. For example, the subject is either uninfected and at risk of the viral infection or is infected in need of treatment.

Therapeutically effective amount: The amount of an agent (such as an anti-viral agent) or therapy, that alone, or together with one or more additional agents, induces the desired response, such as, for example treatment of a viral infection in a subject. Ideally, a therapeutically effective amount provides a therapeutic effect without causing a substantial cytotoxic effect in the subject.

A therapeutically effective amount of an agent or therapy that is administered to a human or veterinary subject will vary depending upon a number of factors associated with that subject, for example the overall health of the subject. A therapeutically effective amount can be determined by varying the dosage and measuring the resulting therapeutic response, such as the reduction of symptoms associated with viral infection. The agents can be administered in a single dose, or in several doses, as needed to obtain the desired response. However, the therapeutically effective amount can be dependent on the source applied, the subject being treated, the severity and type of the condition being treated, and the manner of administration.

In some embodiments, a therapeutically effective amount of a competitive inhibitor of ouabain binding to ATP1A1 (such as PST2238) is sufficient to reduce or eliminate a symptom of a viral infection. For instance, this can be the amount necessary to inhibit or prevent viral replication or to measurably alter outward symptoms of the viral infection. In general, this amount will be sufficient to measurably inhibit viral replication or infectivity.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. A unit dosage form of the agent can be packaged in a therapeutic amount, or in multiples of the therapeutic amount, for example, in a vial (e.g., with a pierceable lid) or syringe having sterile components.

Under conditions sufficient for: A phrase that is used to describe any environment that permits a desired activity.

Viral infection: Infection of a subject by a virus, including acute, chronic, and latent infection. Methods of identifying and selecting a subject with a viral infection are known.

II. Treating and Inhibiting Viral Infection

It is shown herein that administration of a competitive antagonist of ouabain binding to ATP1A1 to a subject substantially inhibits viral infection in the subject. Accordingly, methods are provided herein for the inhibition and treatment of a viral infection. The methods include administering to a subject a therapeutically effective amount of a competitive antagonist of ouabain binding to ATP1A1 (such as PST2238) to a subject with or at risk of the viral infection (such as an RSV infection). The methods can be used pre-exposure (for example, to prevent or inhibit influenza A infection) or in post-exposure prophylaxis.

In some embodiments, the viral infection is an infection with a negative-sense single-stranded RNA virus. In some embodiments, the viral infection is an infection with a virus of the Pneumoviridae family.

In some embodiments, the viral infection is an infection with a virus that utilizes epidermal growth factor receptor signaling for cellular entry. For example the infection is an infection with any one of: Respiratory Syncytial Virus, Adenovirus, Clade A New World arenavirus Pichindé, African swine fever virus, Hepatitis C virus, Hepatitis B virus, Human cytomegalovirus, Herpes simplex virus, Epstein-Barr virus, Influenza A virus, Human papillomavirus, Human parainfluenza virus Type 1-3, Adeno-associated virus, Enterovirus 71, Rhinovirus, Vaccinia virus, Cowpox virus, Western Reserve, International Health Department-J, Shope fibroma virus, Human immunodeficiency virus, Avian erythroblastosis virus, or Mouse Cas NS-1 retrovirus.

In some embodiments, the viral infection is an infection with a virus that utilizes ATP1A1 signaling for cellular entry. For example, the infection is an infection with any one of: influenza virus, Herpes simplex virus, Chikungunya virus, Human immunodeficiency virus type 1, Adenovirus, Porcine reproductive and respiratory syndrome virus 1, Ebola virus, Coronavirus, Hepatitis C virus, Lymphocytic choriomeningitis virus, Lassa virus, or Junin virus.

The viral infection does not need to be completely eliminated for the method to be effective. For example, the method can reduce the viral infection by a desired amount, for example by at least 10%, at least 20%, at least 50%, at least 60%, at least 70%, at least 80%, at least 90%, at least 95%, at least 98%, or even at least 100% (elimination of detectable infection) as compared to the infection in the absence of the treatment. In some embodiments, the subject can also be treated with a therapeutically effective amount of an additional agent, such as anti-viral agent.

In one embodiment, administration of the competitive antagonist of ouabain binding to ATP1A1 to the subject (such as PST2238) results in a reduction in the establishment of the viral infection and/or reduces subsequent viral disease progression in the subject. A reduction in the establishment of the viral infection and/or a reduction in subsequent disease progression encompass any statistically significant reduction in viral activity in the subject.

A subject can be selected for treatment that has, or is at risk for developing a viral infection, for example because of exposure or the possibility of exposure to the virus. Following treatment, the subject can be monitored for infection or symptoms associated therewith, or both.

Typical subjects intended for treatment with the methods of the present disclosure include humans, as well as non-human primates and other animals, such as cattle.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize viral infection (such as RSV infection). These and other routine methods allow the clinician to select patients in need of therapy using the methods of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

In a preferred embodiment, a desired response according to the methods of the disclosure is to inhibit or reduce or prevent RSV infection in a subject. The RSV infection does not need to be completely eliminated or reduced or prevented for the method to be effective. For example, administration of a therapeutically effective amount of the competitive antagonist of ouabain binding to ATP1A1 to the subject (such as PST2238) can reduce or inhibit the RSV infection (for example, as measured by infection of cells, or by number or percentage of subjects infected by RSV, by an increase in the survival time of infected subjects, or by a decrease in the severity of symptoms of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable RSV infection, as compared to a suitable control).

A subject can be selected for treatment that has, or is at risk for developing RSV infection, for example because of exposure or the possibility of exposure to RSV. Following treatment, the subject can be monitored for RSV infection or symptoms associated therewith, or both.

Typical subjects intended for treatment for RSV infection with the methods of the present disclosure include humans, as well as non-human primates and other animals, such as cattle. Because nearly all humans are infected with RSV by the age of 5, the entire birth cohort is included as a relevant population for treatment. Subjects at greatest risk of RSV infection with severe symptoms (e.g. requiring hospitalization) include children with prematurity, bronchopulmonary dysplasia, and congenital heart disease are most susceptible to severe disease. Atopy or a family history of atopy has also been associated with severe disease in infancy. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. (See, e.g., Shay et al., JAMA, 282: 1440-6, 1999; Hall et al., N Engl J Med. 2009; 360:588-598; Glezen et al., *Am J Dis Child.,* 1986; 140:543-546; and Graham, Immunol. Rev., 239:149-166, 2011, each of which is incorporated by reference herein). In some embodiments, these subjects can be selected for administration of the competitive antagonist of ouabain binding to ATP1A1 to the subject (such as PST2238) to inhibit or treat RSV infection in the subject.

The administration of a disclosed agent can be for prophylactic or therapeutic purpose. When provided prophylactically, the agent can be provided in advance of any symptom, for example in advance of infection. The prophylactic administration serves to prevent or ameliorate any subsequent infection. In some embodiments, the methods can involve selecting a subject at risk for contracting viral (such as RSV) infection, and administering a therapeutically effective amount of a competitive antagonist of ouabain binding to ATP1A1 (such as PST2238) to the subject. The competitive antagonist of ouabain binding to ATP1A1 to the subject (such as PST2238) can be provided prior to the anticipated exposure to RSV so as to attenuate the anticipated severity, duration or extent of an infection and/or associated disease symptoms, after exposure or suspected exposure to the virus, or after the actual initiation of an infection.

When used therapeutically, the competitive antagonist of ouabain binding to ATP1A1 (such as PST2238) is provided at or after the onset of a symptom of RSV infection, or after diagnosis of RSV infection. Treatment of RSV by inhibiting RSV replication or infection can include delaying and/or reducing signs or symptoms of RSV infection in a subject. In some examples, treatment using the methods disclosed herein prolongs the time of survival of the subject. In some embodiments, administration of the competitive antagonist of ouabain binding to ATP1A1 to the subject (such as PST2238) prevents or inhibits serious lower respiratory tract disease, such as pneumonia and bronchiolitis, or croup.

The actual dosage of the competitive antagonist of ouabain binding to ATP1A1 (such as PST2238) administered to the subject will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A therapeutically effective amount is also one in which any toxic or detrimental side effect of the competitive antagonist of ouabain binding to ATP1A1 (such as PST2238) is outweighed in clinical terms by therapeutically beneficial effects. A non-limiting range for a therapeutically effective amount of the competitive antagonist of ouabain binding to ATP1A1 (such as PST2238) within the methods of the disclosure is about 0.001 mg/kg body weight to about 20 mg/kg body weight, such as about 0.005 mg/kg to about 5 mg/kg body weight, about 0.01 mg/kg to about 5 mg/kg body weight, about 0.05 mg/kg to about 5 mg/kg body weight, about 0.1 mg/kg to about 5 mg/kg body weight, about 0.005 mg/kg to about 10 mg/kg body weight, or about 0.01 mg/kg to about 10 mg/kg body weight. In some embodiments, the dosage of the competitive antagonist of ouabain binding to ATP1A1 (such as PST2238) administered to the subject is about 5 mg twice a day for a preselected period of time, such as 7 days or 14 days, or more or fewer days. In some embodiments, the dosage of the competitive antagonist of ouabain binding to ATP1A1 (such as PST2238) administered to the subject is about 0.5 mg per day for a preselected period of time, such as 7 days or 14 days, or a month, or two months, or three months, or more or less time. The amount of agent utilized is selected based on the subject population (e.g., infant or elderly). An optimal amount for a particular composition can be ascertained by standard studies involving observation of infection status and other responses in subjects. It is understood that a therapeutically effective amount of the competitive antagonist of ouabain binding to ATP1A1 (such as PST2238) can include an amount that is ineffective for treating the viral infection in the subject by administration of a single dose, but that is effective upon administration of multiple dosages, for example over the course of 1-2 weeks.

For each particular subject, specific dosage regimens can be evaluated and adjusted over time according to the individual need and professional judgment of the person administering or supervising the administration of the competitive antagonist of ouabain binding to ATP1A1.

Determination of effective dosages is typically based on animal model studies followed up by human clinical trials and is guided by administration protocols that significantly reduce the occurrence or severity of targeted disease symptoms or conditions in the subject, or that induce a desired response in the subject. Suitable models in this regard include, for example, murine, rat, porcine, feline, ferret, non-human primate, and other accepted animal model subjects known in the art. Alternatively, effective dosages can be determined using in vitro models (for example, airway cells such as A549 cells or primary small airway epithelial cells). Using such models, only ordinary calculations and adjustments are required to determine an appropriate concentration and dose to administer a therapeutically effective amount of the composition (for example, amounts that are effective to alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

III. Compositions and Administration Thereof

The competitive antagonist of ouabain binding to ATP1A1 (such as PST2238) can be administered to humans or other animals on whose cells they are effective in various manners such as topically, orally, intravenously, intramuscularly, intraperitoneally, intratumorally, intranasally, intradermally, intrathecally, and subcutaneously, by inhalation, by endotracheal tube, or by injection into the intestine. By way of example, one method of administration to the lungs of an individual is by inhalation through the use of a nebulizer or inhaler. For example, the competitive antagonist of ouabain binding to ATP1A1 (such as PST2238) is formulated in an aerosol or particulate and drawn into the lungs using a nebulizer.

The particular mode of administration and the dosage regimen will be selected by the attending clinician, taking into account the particulars of the case (e.g. the subject, the disease, the disease state involved, and whether the treatment is prophylactic). In cases in which more than one agent or composition is being administered, one or more routes of administration may be used. Treatment can involve daily or multi-daily doses of compound(s) over a period of a few days to months, or even years.

The competitive antagonist of ouabain binding to ATP1A1 (such as PST2238) administered to the subject is typically included in a pharmaceutical composition including a pharmaceutically acceptable carrier or excipient. The pharmaceutically acceptable carriers and excipients useful in the disclosed methods are conventional. For instance, parenteral formulations usually comprise fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations can be liquid (e.g. syrups, solutions or suspensions), or solid (e.g. powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some embodiments, site-specific administration of the disclosed compounds can be used. Slow-release formulations are known to those of ordinary skill in the art. By way of example, polymers such as bis(p-carboxyphenoxy)propane-sebacic-acid or lecithin suspensions may be used to provide sustained localized release.

The formulations can be prepared by combining the competitive antagonist of ouabain binding to ATP1A1 (such as PST2238) uniformly and intimately with liquid carriers or finely divided solid carriers or both. The formulations can also be prepared by combining microparticles including or consisting of the nanoparticles uniformly and intimately with liquid carriers or finely divided solid carriers or both.

The pharmaceutical compositions that comprise the competitive antagonist of ouabain binding to ATP1A1 (such as PST2238) can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. Administration may begin whenever appropriate as determined by the treating physician.

The compositions or pharmaceutical compositions can include a nanoparticle including the competitive antagonist of ouabain binding to ATP1A1 (such as PST2238), which can be administered locally, such as by pulmonary inhalation or intra-tracheal delivery. When nanoparticles are provided, or microparticles including or consisting of these nanoparticles are provided, e.g. for inhalation or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

For administration by inhalation, nanoparticles or microparticles including the ouabain antagonist (such as PST2238) can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

Methods of administration include injection for which the competitive antagonist of ouabain binding to ATP1A1 (such as PST2238) or a composition including the competitive antagonist of ouabain binding to ATP1A1 (such as PST2238) is provided in a nontoxic pharmaceutically acceptable carrier such as water, saline, Ringer's solution, dextrose solution, 5% human serum albumin, fixed oils, ethyl oleate, or liposomes.

The pharmaceutical compositions that comprise the competitive antagonist of ouabain binding to ATP1A1 (such as PST2238) can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

EXAMPLES

The following examples are provided to illustrate particular features of certain embodiments, but the scope of the claims should not be limited to those features exemplified.

Example 1

ATP1A1 Mediates the Macropinocytic Entry of RSV in Human Respiratory Epithelial Cells Human RSV is the leading viral cause of acute pediatric lower respiratory tract infections worldwide, with no available vaccine or effective antiviral drug. To gain insight into virus-host interactions, a genome-wide siRNA screen was performed. The expression of over 20,000 cellular genes was individually knocked down in human airway epithelial A549 cells, followed by infection with RSV expressing enhanced green fluorescent protein (GFP). Knock-down of expression of the cellular ATP1A1 protein, which is the major subunit of the $Na^+,K^+$-ATPase sodium pump, had the strongest inhibitory effect on GFP expression and viral titer with minimal effects on cell viability. Inhibition was not observed for vesicular stomatitis virus, indicating that it was RSV-specific rather than a general effect. RSV triggered clustering of ATP1A1 in the plasma membrane very early post-infection, which was independent of replication but dependent on the attachment glycoprotein G. RSV also triggered activation of cell surface ATP1A1, resulting in signaling by autophosphorylation of c-Src kinase and trans-activation of epidermal growth factor receptor (EGFR) by Tyr845 phosphorylation. Activation of both c-Src and EGFR was required for RSV entry. The signaling function of ATP1A1 was found to be essential for RSV entry: entry was inhibited by the cardiotonic steroids ouabain and PST2238 (rostafuroxin) that bind specifically to the ATP1A1 extracellular domain and block its signaling. Signaling events downstream of EGFR culminated in the macropinocytic entry of RSV into the host cell. RSV virions at the beginning of infection were found in macropinosomes, suggesting that this is a major route of RSV uptake, with fusion presumably occurring in the macropinosomes rather than at the plasma membrane. The results described below identify ATP1A1 as a host protein essential for macropinocytic entry of RSV into respiratory epithelial cells, and also show that PST2238 is effective as an anti-RSV agent.

Introduction

A number of host proteins and pathways have been suggested to play roles in RSV attachment and entry, but a detailed understanding remained elusive. For instance, it was shown that RSV utilizes lipid rafts in cholesterol-rich microdomains on the cell surface known as caveolae as a docking platform (San-Juan-Vergara et al., *J Virol.* 2012; 86(3):1832-43) essential for RSV entry. Cell surface GAGs also appear to be important in RSV attachment to immortalized cell lines (Hallak et al., *J Virol.* 2000; 74(22):10508-13), but GAGs do not appear to be present on the apical surfaces of primary epithelial cells and so may not play an important role in vivo. Epidermal growth factor receptor (EGFR) signaling has been postulated to play a role in triggering macropinocytic uptake of RSV (Krzyzaniak et al., *PLoS Pathogens.* 2013; 9(4):e1003309), but how this occurs was unknown. It remained unknown if EGFR alone is sufficient or requires other factors to initiate signaling, or if EGFR and its associated signaling are somehow physically linked with caveolae. While RSV entry generally has been thought to involve fusion between the viral envelope and the plasma membrane, new evidence suggested either of two additional, different uptake pathways, namely EGFR-triggered macropinocytosis (Krzyzaniak et al., *PLoS Pathogens.* 2013; 9(4):e1003309) and clathrin-mediated endocytosis (Kolokoltsov et al., *J Virol.* 2007; 81(14):7786-800). It was unclear if one or both are involved.

A genome-wide siRNA screen was previously described in which the expression of over 20,000 genes of human airway epithelial A549 cells was individually knocked down with three individual siRNAs per gene followed by infection with recombinant RSV expressing enhanced green fluorescent protein (RSV-GFP) (Mehedi et al., *PLOS Pathogens.* 2016; 12(12):e1006062). The goal was to identify host proteins affecting the efficiency of RSV infection and replication. The target genes identified by the high throughput screen were confirmed with at least three additional, different siRNAs per gene. The greatest reduction of GFP expression, with minimal effect on cell viability, was observed by knocking down the expression of the gene encoding the cellular protein ATP1A1, which is the major subunit of the $Na^+K^+$ ATPase ion pump. The present example shows the role of this cellular protein in RSV infection.

$Na^+K^+$ ATPase, bearing the ATP1A1 subunit, has been well-characterized as the sole receptor for cardiotonic steroids such as ouabain, which are its sole agonists initiating signaling. Ouabain has been reported in humans as an endogenous hormone-like agent that contributes to the regulation of blood pressure, among other things, via ATP1A1 signaling.

ATP1A1 does not possess a known cytoplasmic signaling domain, but is bound through its cytoplasmic tail to the cellular kinase c-src. Ouabain binding to Na⁺K⁺ ATPase confers a conformation change to c-src that exposes its kinase domain (Tian et al., *Mol Biology Cell.* 2006; 17(1): 317-26), leading to autophosphorylation of c-src at tyrosine 418. This can trigger several different signaling pathways, depending on the cell type, including: (i) the PLC-gamma pathway, (ii) the MAPK cascade, and (iii) the PI3K pathway (reviewed in (Reinhard et al., *Cell Mol Life Sciences*: CMLS. 2013; 70(2):205-22; Xie et al., *Mol Interv.* 2003; 3(3):157-68). The MAPK and PI3K pathways also involve c-src-mediated transactivation of EGFR. EGFR is a tyrosine kinase that, upon EGF binding at its ectodomain, is autophosphorylated at its cytoplasmic domain, resulting in the induction of downstream signaling. However, c-src-mediated activation of EGFR occurs in an EGF-independent manner that can involve phosphorylation at alternative tyrosine residues (Donepudi et al., *Cellular Signalling.* 2008; 20(7):1359-67; Biscardi et al., *J Biol Chem.* 1999; 274(12): 8335-43). Notably, ATP1A1 signaling can lead to the induction of various endocytic pathways. For example, c-src mediated phosphorylation of EGFR can induce macropinocytosis (Donepudi et al., *Cellular Signalling.* 2008; 20(7): 1359-67), similar to the well characterized EGF-induced macropinocytosis (Swanson et al., *Trends Cell Biol.* 1995; 5(11):424-8; Hewlett et al., *J Cell Biol.* 1994; 124(5):689-703). The PI3K pathway can induce clathrin-mediated endocytosis, which removes Na⁺K⁺ ATPase from the plasma membrane for degradation in the lysosome (Cherniaysky-Lev et al., *J Biol Chem.* 2014; 289(2):1049-59; Liu et al., *Kidney Int.* 2005; 67(5):1844-54). Incidentally, this results in decreased ion channel activity and increased blood pressure, and this can be reversed by a synthetic digitoxigenin derivative called rostafuroxin or PST2238, which competitively inhibits ouabain binding and signaling (Ferrari et al., *J Pharmacol Exp Ther.* 1998; 285(1):83-94) and is used therapeutically to lower this kind of hypertension.

The mechanism of how ATP1A1 might participate in virus infection was largely unknown. Here, a novel role for ATP1A1 signaling in enabling RSV entry into human airway epithelial cells is reported. It is demonstrated that RSV induces the signaling function of ATP1A1, reminiscent of ouabain-induced ATP1A1 signaling, to enable cell entry by a mechanism that is dependent on activation of c-Src and EGFR. Evidence is also provided that RSV enters the host cell engulfed in large fluid filled macropinosomes, a location where it presumably fuses and releases the nucleocapsids into the cytoplasm. It is also shown that RSV-induced ATP1A1 signaling occurs at the caveolae, can be inhibited by the cardiotonic steroid such as ouabain, or a digitoxigenin derivative PST2238, as well as by cholesterol-depletion.

Results

Figure 1C:
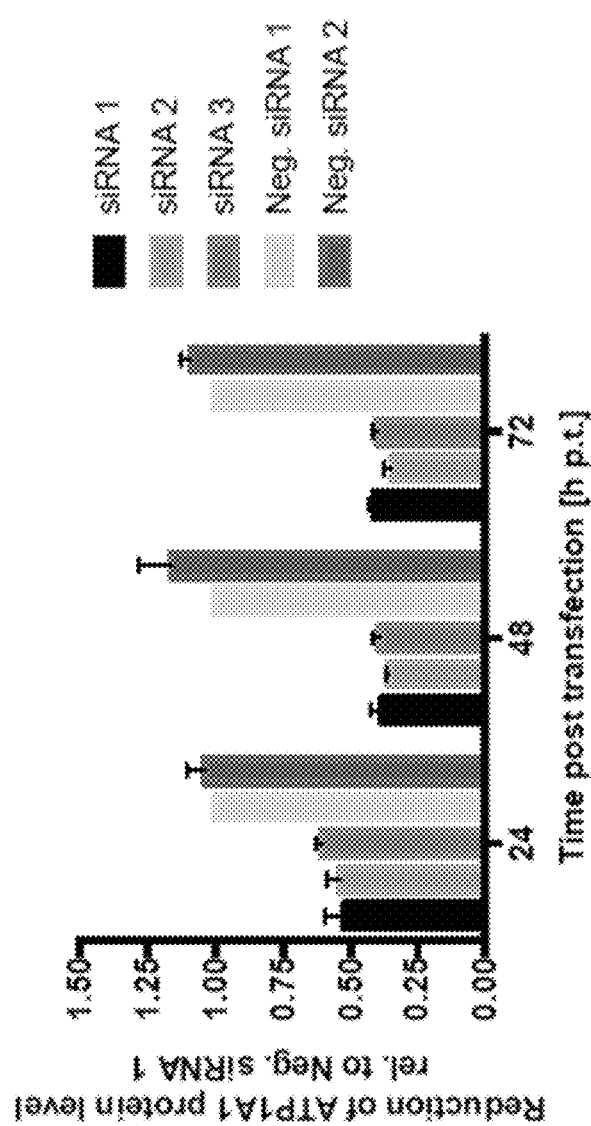

Knock-down of ATP1A1 expression by siRNA transfection. A high-throughput siRNA screen in human airway epithelial A549 cells infected with RSV-GFP, with GFP expression as a surrogate for viral gene expression, showed that knock-down of the expression of the cellular ATP1A1 gene had the greatest inhibitory effect on GFP expression, with minimal effects on cell viability. Three siRNAs with the greatest effect on ATP1A1 expression and RSV infection were used for further experiments, with two different scrambled siRNAs (Neg. siRNA 1 and 2) as negative controls. To confirm the efficiency of knock-down of ATP1A1 mRNA, A549 cells were transfected with this set of five siRNAs, total cell-associated RNA was isolated at 24, 48, and 72 h post-infection (p.i.), and ATP1A1 mRNA was quantified by a TaqMan assay and reported as fold-change relative to Neg. siRNA1 (FIG. 1A). At 24 h post transfection (p.t.), the level of ATP1A1 mRNA was reduced to below 5% compared to Neg. siRNA 1, and showed only modest further reductions at 48 and 72 h p.t. To measure the expression of ATP1A1 protein, A549 cell lysates were prepared at 24, 48 and 72 h p.t. and subjected to Western blot analysis (FIG. 1B). The band intensities were quantified and presented as fold-change relative to Neg. siRNA1 (FIG. 1C). At 24 h p.t. ATP1A1 protein was reduced about 50% for all three ATP1A1 specific siRNAs (siRNA 1-3). ATP1A1 protein expression further reduced at 48 h p.t. to 39% (siRNA1 and 3) and 35% (siRNA2) and did not show any further reduction at 72 h p.t.

The transfected cells showed no visible cytotoxicity or morphological changes over the period of 72 h. For more sensitive evaluation, ATP-dependent luciferase activity, which correlates with ATP amount and reflects cell viability, was measured in cell lysates at 72 h p.t. (FIG. 1D). The data are reported as fold-change relative to mock-transfected cells. The ATP1A1 siRNA knock-down showed only minimal reductions in cell viability (FIG. 1D). The greatest reduction was observed for siRNA 1 at 18%, while siRNA 2 and siRNA 3 had reductions of 11% and 5%, respectively (FIG. 1D).

Figure 2A:
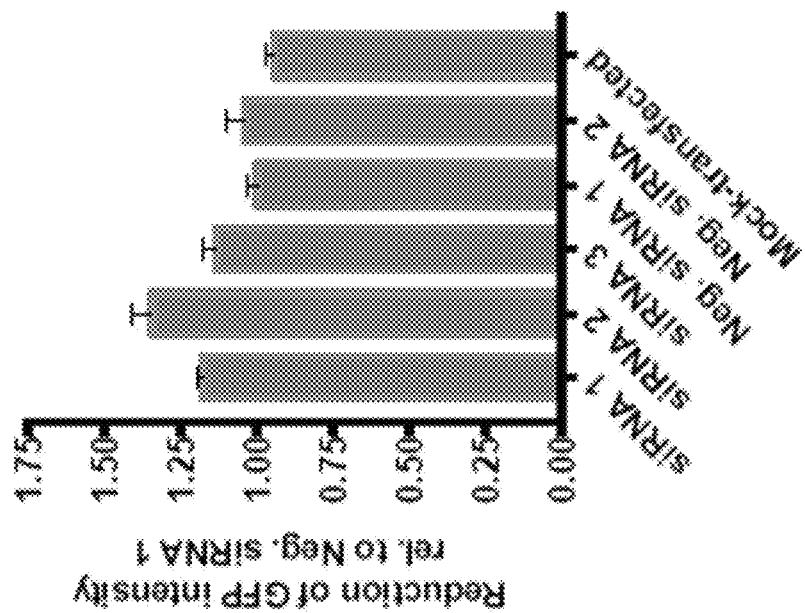
FIGS. 2A-2D. Effect of ATP1A1 knock down on RSV infection. A549 cells were transfected with the indicated siRNAs. Cells were infected with either RSV-GFP (FIG. 2A, MOI=1 PFU/cell) or VSV-GFP (FIG. 2B, MOI=0.5 PFU/cell) at 48 h post siRNA transfection. Infection of RSV (FIG. 2A) and VSV (FIG. 2B) were quantified by GFP intensity of the total well (area scan by ELISA reader) at 17 h p.i. In addition, RSV GFP expression of single, live, GFP cells was also examined and quantified by flow cytometry assay 24 h p.i.
Figure 2B:
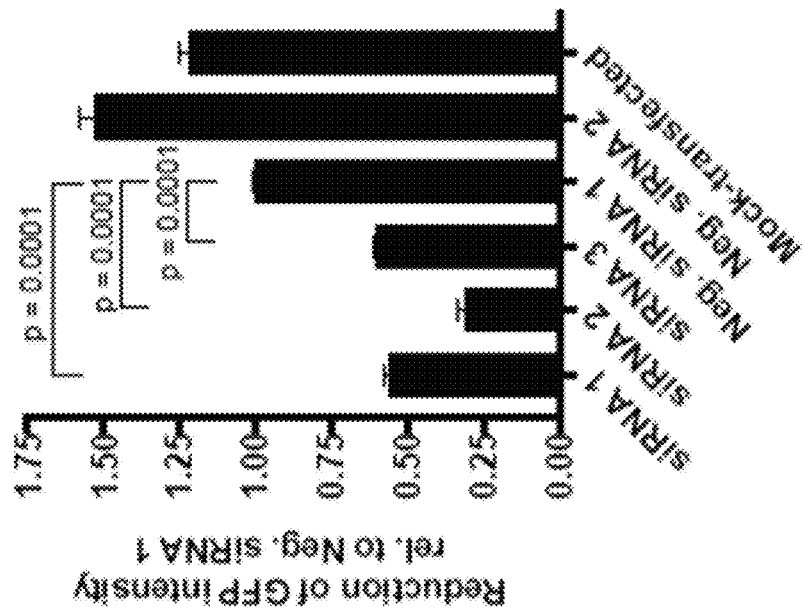
Figure 2C:
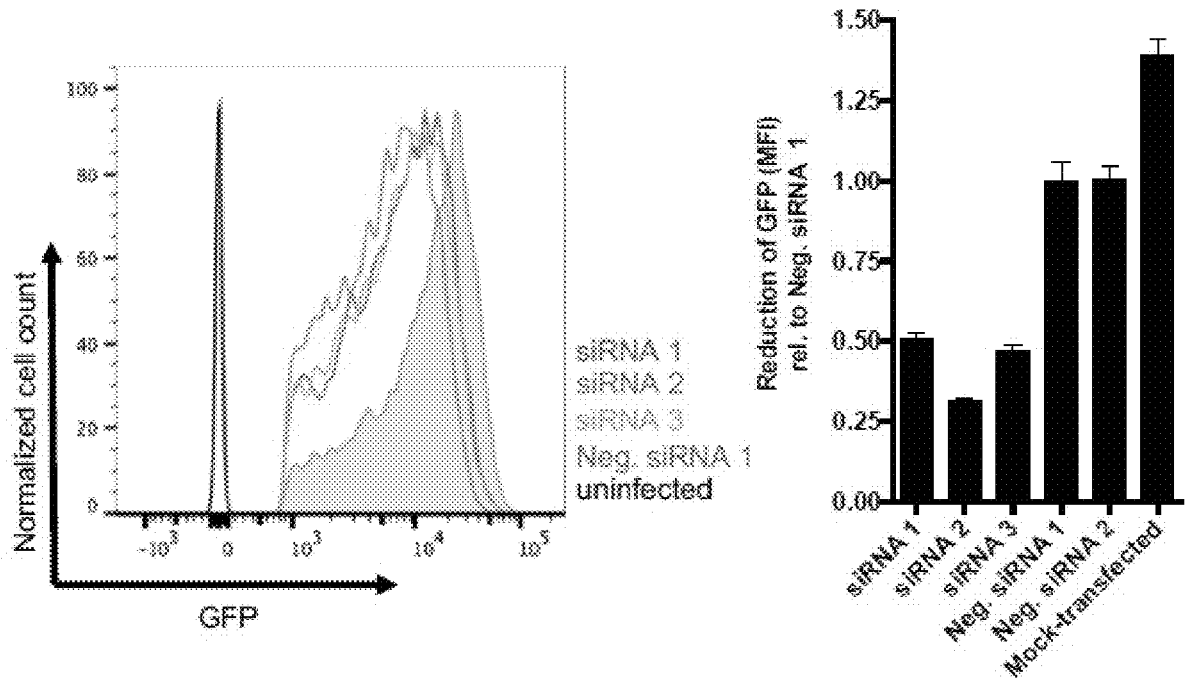

ATP1A1 knock-down reduces RSV infection. A549 cells were transfected with the panel of siRNAs targeting ATP1A1 48 h prior to infection with RSV-GFP at an MOI of 1 plaque forming unit (PFU)/cell. The efficiency of virus infection and replication were evaluated by GFP expression quantified by ELISA reader and flow cytometry, shown in FIGS. 2A and 2C, respectively. By ELISA reader, all three ATP1A1-specific siRNAs reduced the amount of GFP expression by about 50 to 75% compared to Neg. siRNA 1 (FIG. 2A). This level of reduction was substantial given that the residual level of ATP1A1 expression remained 35% or greater, as was shown in FIG. 1C. The effects on infection with vesicular stomatitis virus expressing GFP (VSV-GFP) were assessed. ATP1A1 knock-down had no effect on GFP expression by VSV-GFP (FIG. 2B). This indicated that the reduction in GFP expression observed with RSV-GFP was specific to RSV, did not affect VSV, and was not due to some general effect on cellular functions. Analysis of cells infected with RSV-GFP (MOI=1.0 PFU/cell) by flow cytometry 24 h p.i. showed that knock-down of ATP1A1 resulted in a broad reduction in RSV-GFP expression in the infected-cell population rather than a reduction in the number of GFP-expressing cells (FIG. 2C).

Figure 2D:
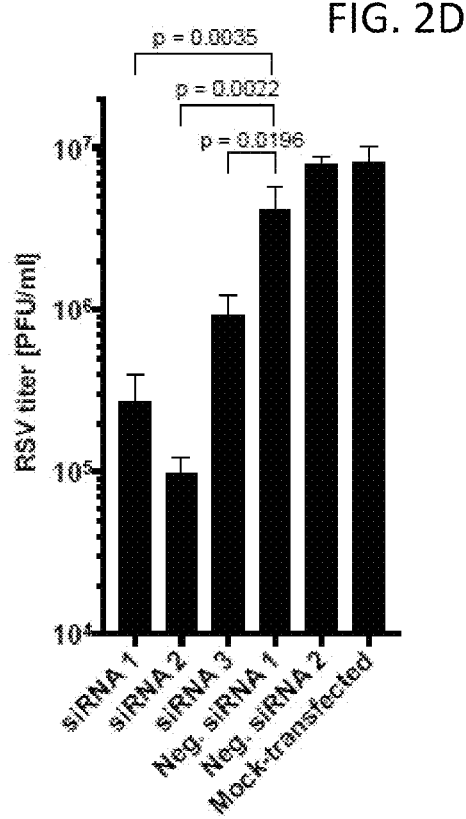

The effects on the production of progeny RSV were assessed 24 h p.i. The infected cells were collected by scraping, vortexed to release cell-associated virus, and pelleted by centrifugation. Virus titers in the clarified supernatants were quantified by plaque titration on Vero cells (FIG. 2D). This showed that, with ATP1A1 knock-down, RSV titers were reduced between 5- (siRNA3) and 42-fold (siRNA2) compared to Neg. siRNA 1 at 24 h p.i., an effect that was even more dramatic than the reduction in GFP expression described above (FIG. 2D versus 2A and C); ATP1A1 siRNA 2 showed the strongest effect in both cases.

Figure 3A:
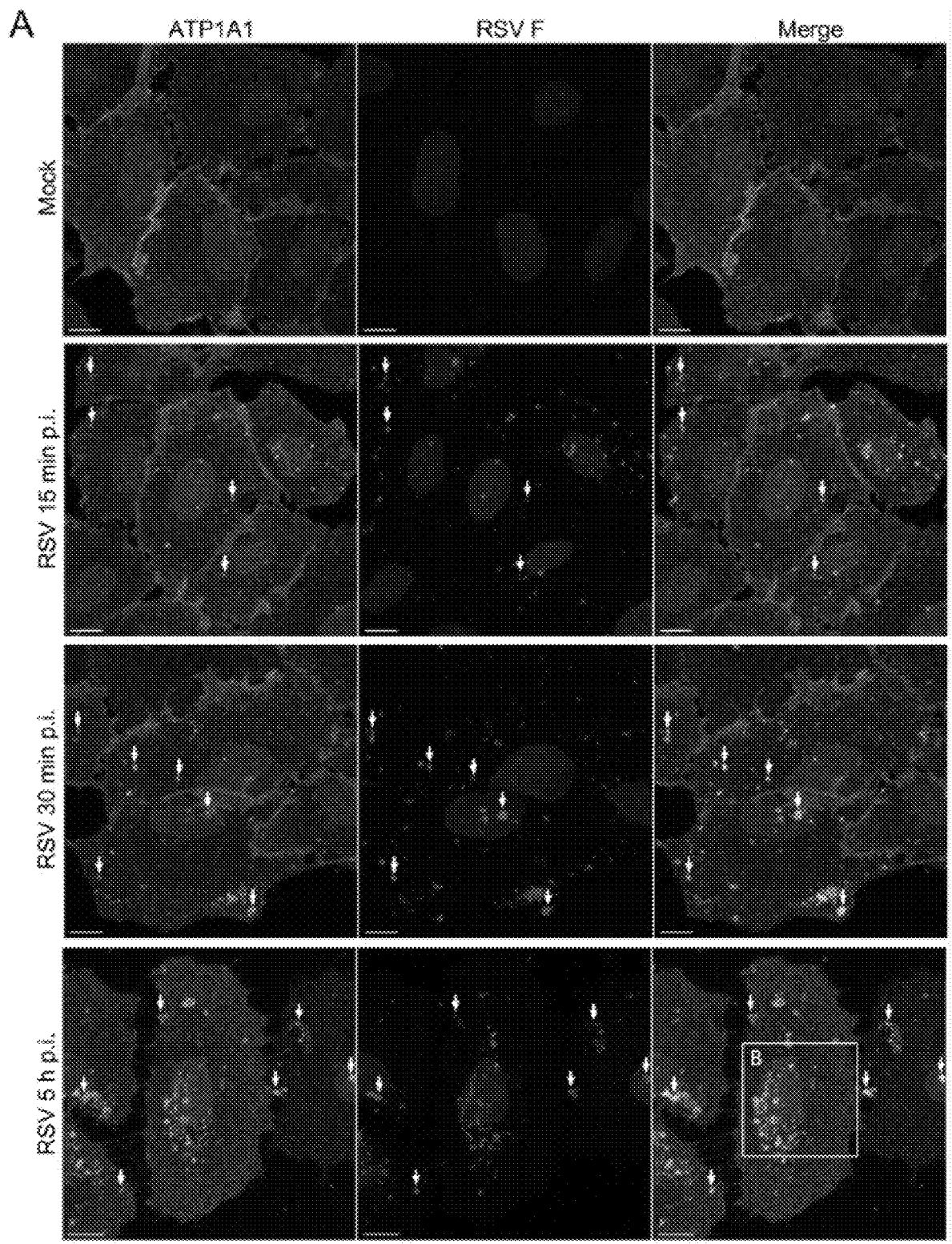
FIGS. 3A and 3B. RSV infection triggers ATP1A1 clustering.
Figure 4:
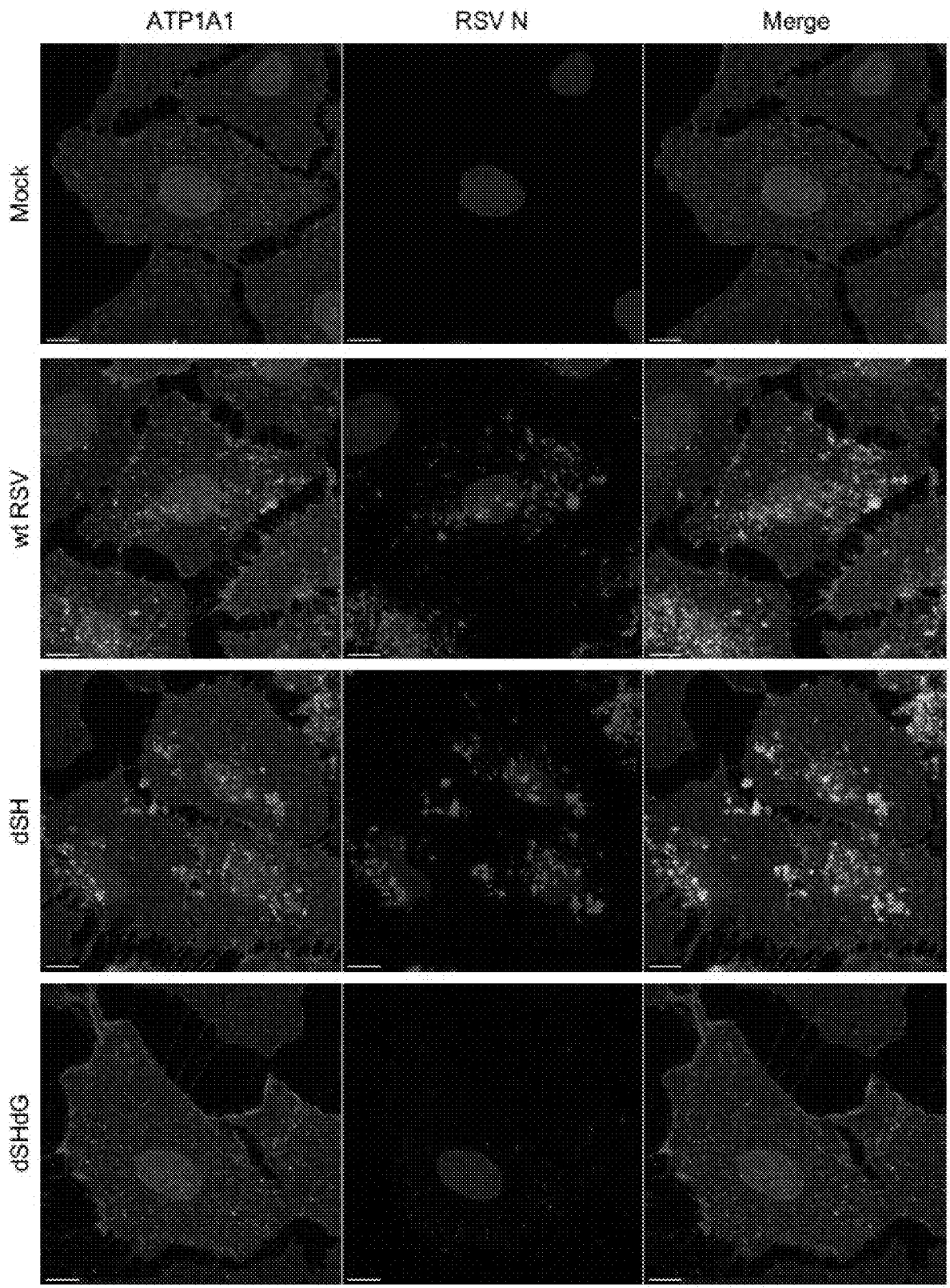
FIG. 4. RSV-G is required for ATP1A1 clustering. A549 cells were inoculated with wt RSV, rgRSV-dSH or rgRSV-dSH dG (MOI=10 PFU/cell) and incubated for 5 h at 37° C. Cells were fixed with 4% PFA and subjected to immunofluorescence staining, as described for FIG. 3. ATP1A1 (shown in green) was detected by a rabbit anti-ATP1A1 antibody (ab76020) and Alexa Fluor 568 conjugated donkey anti-rabbit secondary antibody. RSV N (shown in red) was detected by a mouse monoclonal anti-RSV N antibody (ab94806) and an Alexa Fluor 647 conjugated donkey anti-mouse secondary antibody. The cell nuclei were stained with DAPI and are shown in all channels. Images (z-stacks) were acquired on a Leica SP8 confocal microscope, with a 63× objective (NA 1.4) and a zoom of 3.0. Scale bar 10 µm.
Figure 13:
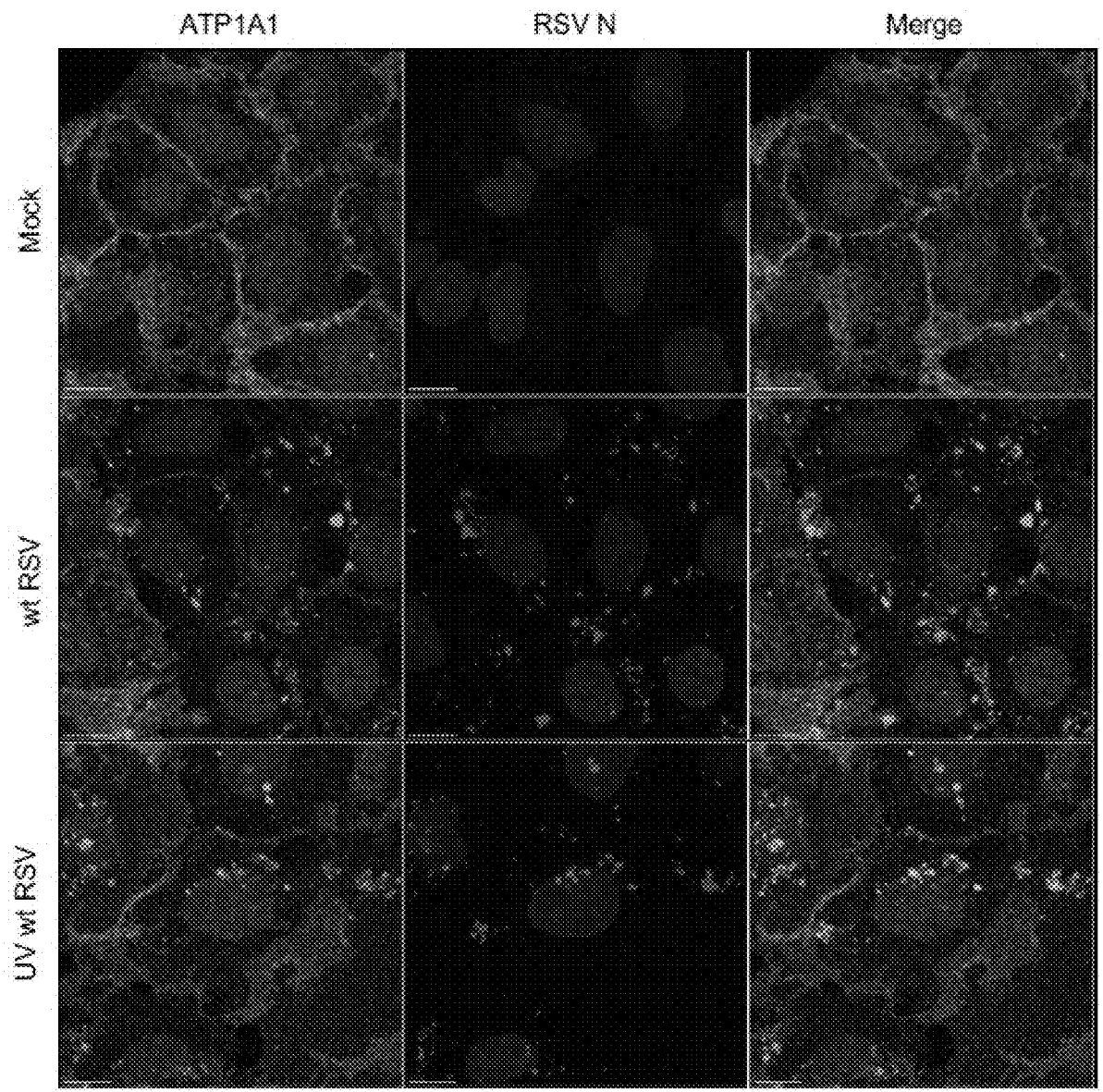
FIG. 13. ATP1A1 clustering induced by UV-inactivated RSV. A549 cells were inoculated (MOI=5 PFU/cell) as described for FIG. 3 and incubated for 5 h at 37° C. The UV wt RSV inoculum was UV-inactivated by 0.5 J/cm$^2$ UV radiation using a Stratalinker UV Crosslinker 1800 (Agilent). Total inactivation of the inoculum was confirmed by plaque assay titration on Vero cells as described. Cells were subjected to immunofluorescence staining for ATP1A1 (Alexa Fluor 488, green) and RSV-N (Alexa Fluor 568, red) and counterstained with DAPI with the described staining protocol. Scale bars 10 µm.

ATP1A1 forms clusters early during RSV infection independent of viral gene transcription or replication. A549 cells were infected with wt RSV (MOI=5 PFU/cell), fixed at different times p.i., and subjected to immunofluorescence staining for ATP1A1 and RSV F protein. In mock-treated (uninfected) cells, ATP1A1 was homogenously distributed on the plasma membrane (FIG. 3A, top row). Following infection with wt RSV, clusters of ATP1A1 were observed as early as 15 min p.i. (FIG. 3A, second row from top), whereas these clusters were not evident in uninfected cells (FIG. 3A, top row). With time, the ATP1A1 clusters became more prominent and numerous, as shown for 30 min and 5 h p.i. (FIG. 3A, third and fourth rows from top). Some ATP1A1 clusters, but not all, partially co-localized with RSV F protein (FIG. 3A, indicated by arrows). The localization of clustered ATP1A1 in close proximity to RSV F became more noticeable at later time points such as 5 h p.i. (FIG. 3A, bottom panel). Localization of ATP1A1 clusters close to RSV N protein also could be observed (FIG. 4 and FIG. 13), suggesting that the RSV-specific staining most likely reflects enveloped virions (which had not yet fused). Similar clustering of ATP1A1 and RSV N protein also was observed for UV-inactivated RSV (FIG. 13), indicating that the staining largely involved pre-formed proteins from the incoming virus, and that clustering does not require transcription of the complete viral genome, viral RNA replication, and virus replication.

Figure 3B:
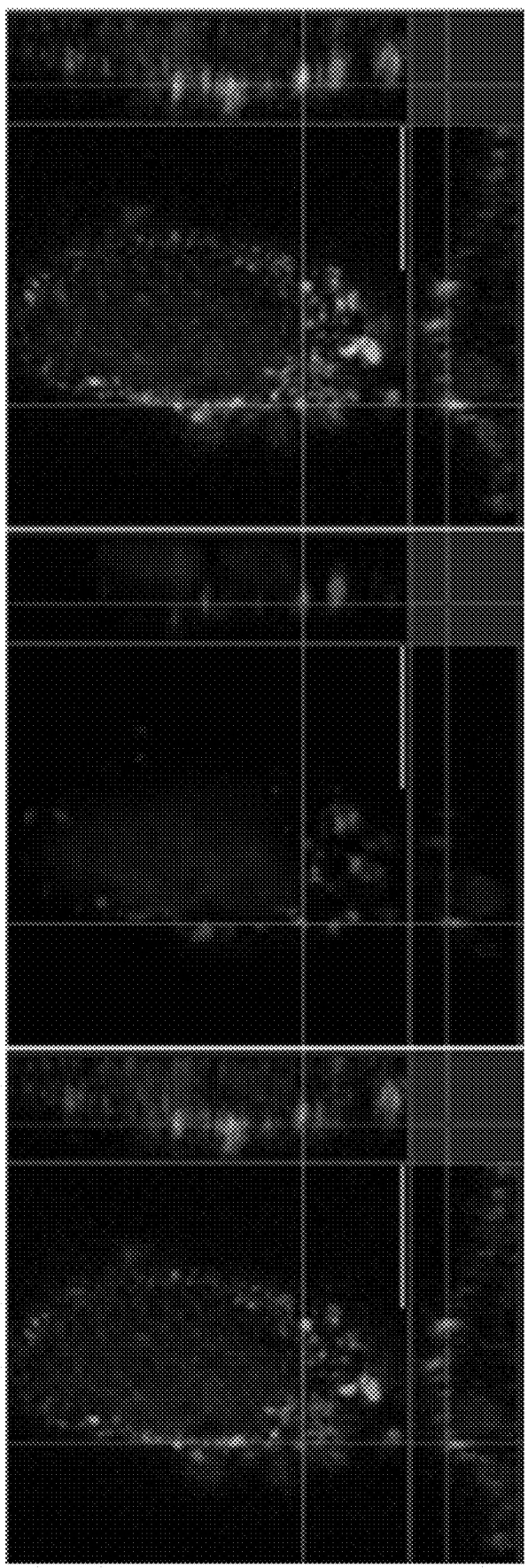

Cross-sections (FIG. 3B) of images of RSV-infected A549 cells 5 h p.i. indicate that the ATP1A1 clustering occurred at the cell surface and was localized close to the RSV virions. Given the very early appearance of ATP1A1 clusters, independent of viral transcription or replication, it was hypothesized that ATP1A1 might be involved in an early step of infection such as viral entry.

Figure 14:
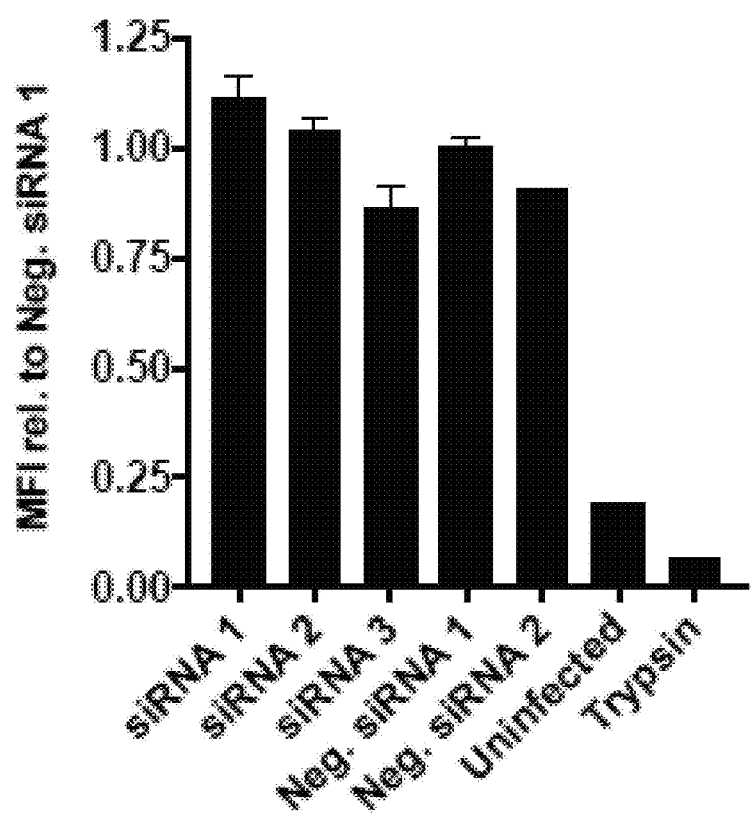
FIG. 14. Effect of ATP1A1 knock down on RSV binding on the cell surface. A549 cells were transfected with the indicated siRNAs targeting the ATP1A1 mRNA or unspecific negative siRNA. 48 h p.t. cells were detached with 1 mM EDTA in 1×PBS and the suspended cells were incubated with wt RSV (MOI=10 PFU/cell) on ice for 30 min. Cells were washed to remove any unbound virus and stained for RSV F with a pool of mouse monoclonal RSV F specific antibodies followed by an Alexa Fluor 647 conjugated anti-mouse secondary antibody. Cells treated with trypsin prior to incubation with virus served as a negative control for virus binding. Cells were analyzed by flow cytometry.

Lack of interaction of ATP1A1 with RSV proteins. If ATP1A1 is involved in early steps of infection, it was hypothesized that one or more of the RSV proteins, and especially the three viral surface glycoproteins F, G, and SH, might interact with ATP1A1. Various immunoprecipitation assays were performed to investigate binding. For example, we used the human lung epithelial cell line H1299 ATP1A1-YFP that chromosomally expressed, from one allele, ATP1A1 genetically fused to yellow fluorescent protein (YFP) tag (Sigal et al., *Nature methods.* 2006; 3(7):525-31; Frenkel-Morgenstern et al., *Nucleic acids research.* 2010; 38 (Database issue):D508-12). These cells were infected with RSV, lysed, and co-immunoprecipitation was performed with YFP-specific antibodies followed by Western blotting with antibodies to RSV proteins. Comparable co-precipitation experiments in which, prior to lysis, the cells were treated with the permeable, reversible cross-linker dithiobis (succinimidyl propionate) were also performed. RSV virions were also incubated with ATP1A1 immobilized on beads. However, there was no evidence of binding between ATP1A1 and RSV proteins in these various experiments. A cell-based binding assay was also performed, as described by Martinez et al. (*J General Virol.* 2000; 81(Pt 11):2715-22), with A549 cells that were siRNA-transfected to knock down ATP1A1 (FIG. 14). At 48 h post siRNA transfection, cells were detached and incubated with the RSV inoculum (MOI=10 PFU/cell) on ice for 30 min. Cells were extensively washed and bound virus was detected with a pool of RSV F specific antibodies. The samples were analyzed on Canto II flow cytometer and the MFI reported as fold-change relative to Neg. siRNA1 transfected cells. ATP1A1 knock-down did not show an appreciable reduction in RSV binding (FIG. 14), indicating that ATP1A1 likely did not contribute to attachment by RSV. Treatment of the cells with heparinase I prior to exposure to RSV to remove cell surface GAGs, which was done to eliminate GAG-mediated RSV attachment, also did not reveal any contribution of ATP1A1 to RSV attachment. Therefore, there was no evidence of stable binding of any RSV protein to ATP1A1.

RSV G protein is required for ATP1A1 clustering. As another means of exploring early events in RSV infection, whether RSV mutants bearing the deletion of the SH protein (dSH) or the deletion of SH and the attachment G glycoprotein (dSH/dG) were able to trigger the clustering of ATP1A1 (deletion of RSV F could not be investigated because it abrogates infectivity) was investigated. A549 cells were infected with wt RSV, RSV dSH, or RSV dSH/dG (MOI=10 PFU/cell) and incubated for 5 h at 37° C. Cells were fixed, permeabilized and immunostained with antibodies specific to ATP1A1 (green) and RSV N (red). Wt RSV was included as a reference and showed increased cluster formation due to the increased MOI of 10 PFU/cell (FIG. 4) compared to an MOI of 5 PFU/cell (FIG. 3). The RSV dSH virus induced clustering that was very similar to that with wt RSV, indicating that deletion of the SH protein seemed to have no effect on ATP1A1 clustering. On the other hand, the dSH/dG virus did not induce any ATP1A1 clustering, and the presumed viral particles, stained for RSV N in red, were reduced in amount and much more dispersed and did not accumulate in larger vesicles as seen for wt RSV and the dSH virus. The lack of ATP1A1 cluster formation with the dSH/dG virus suggested that RSV G protein is involved in triggering ATP1A1 clustering as part of RSV entry.

Ouabain and PST2238 (Rostafuroxin) inhibit RSV infection. The clustering of ATP1A1 upon RSV exposure seemed to be analogous to that observed for cell surface receptors known to facilitate intracellular signaling in response to ligand binding (Gopalakrishnan et al., *Biophys J.* 2005; 89(6):3686-700). This suggested that the signaling function of ATP1A1 might play a role in RSV infection. As noted above, the only known agonists for ATP1A1 signaling are cardiotonic steroids such as ouabain, which activates non-receptor tyrosine kinase Src-mediated signaling pathways and induces endocytosis including clathrin-mediated, caveolin-mediated, and macropinocytosis. The synthetic digitoxigenin derivative PST2238 is a competitive inhibitor of ouabain that competes for its binding site on ATP1A1 and thus inhibits ouabain binding and signaling (Ferrari et al., *J Pharmacol Exp Ther.* 1998; 285(1):83-94).

Figures 5D, 5E:
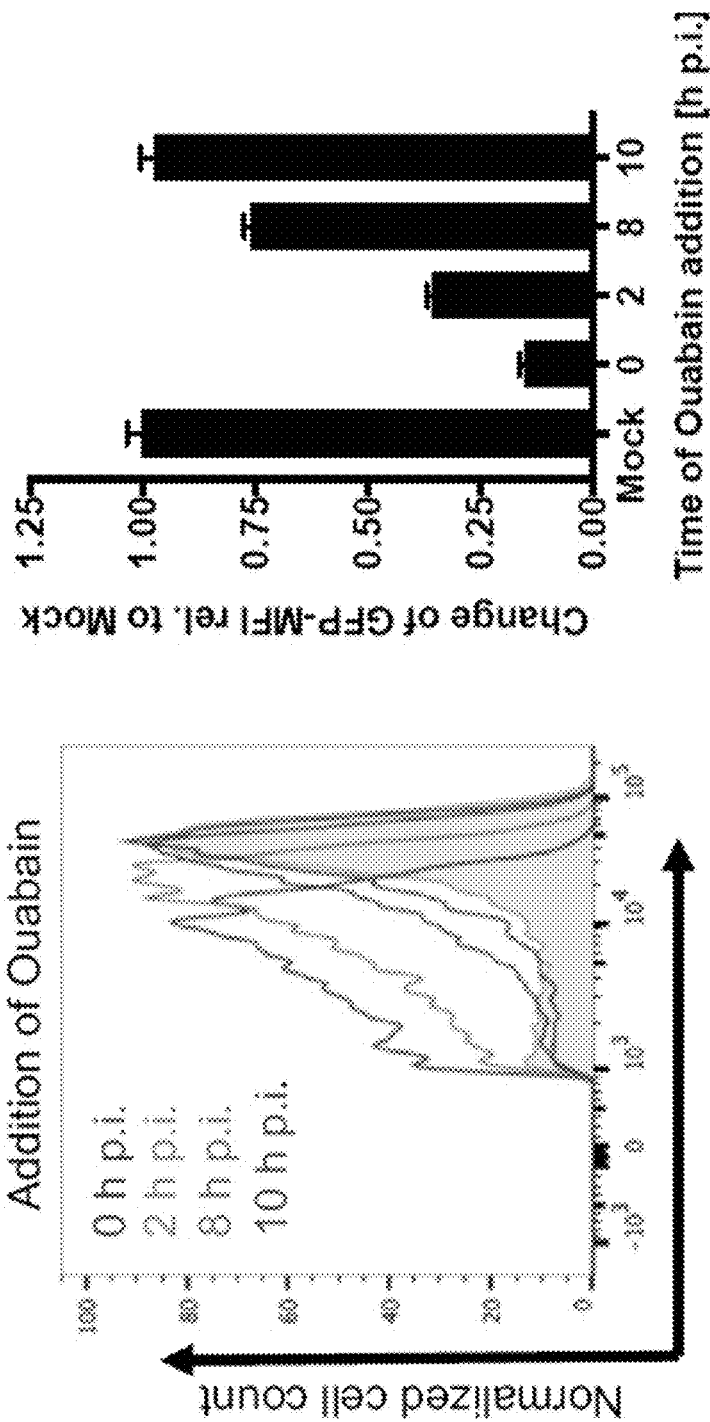
Figures 15A, 15B:
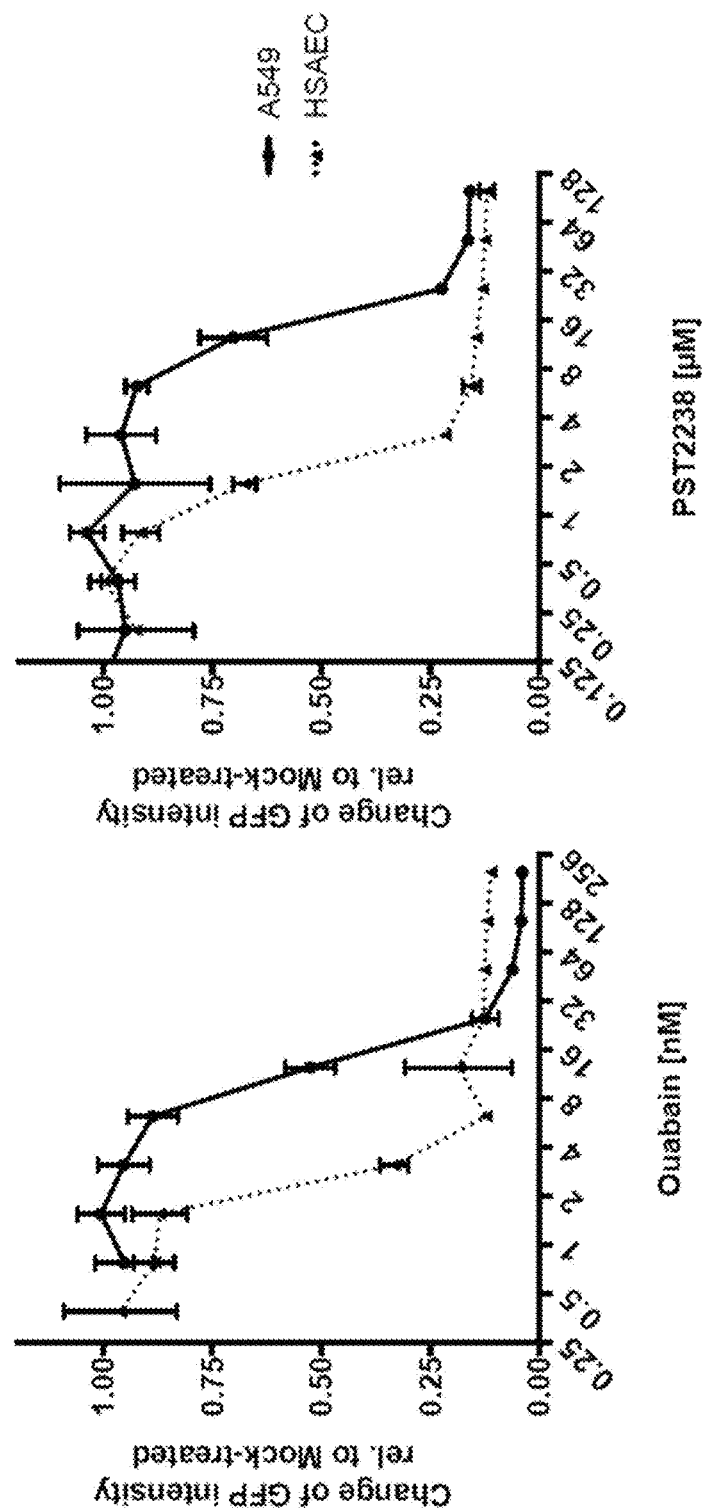
FIGS. 15A-15D. Efficacy ($IC_{50}$) and cytotoxicity titration of ouabain and Rostafuroxin (PST2238) on A549 cells and primary human small airway epithelial cells (HSAEC). RSV-GFP infection inhibitor titration of ouabain (FIG. 15A) and PST2238 (FIG. 15B) on A549 cells and HSAEC 24 h p.i. Infection of RSV was quantified by GFP intensity of the total well (area scan by ELISA reader) in triplicates for each concentration and reported relative to mock-treated infected cells with error bars indicating the standard deviation. Cytotoxicity titration of ouabain (FIG. 15C) and PST2238 (FIG. 15D) on A549 cells and HSAEC after 24 h treatment. Cell viability was determined in triplicates for each concentration by the ATP based viability assay CELLTITER-GLO® (PROMEGA®) and changes in viability are reported as fold change relative to mock-treated cells with error bars indicating the standard deviation.
Figures 15C, 15D:
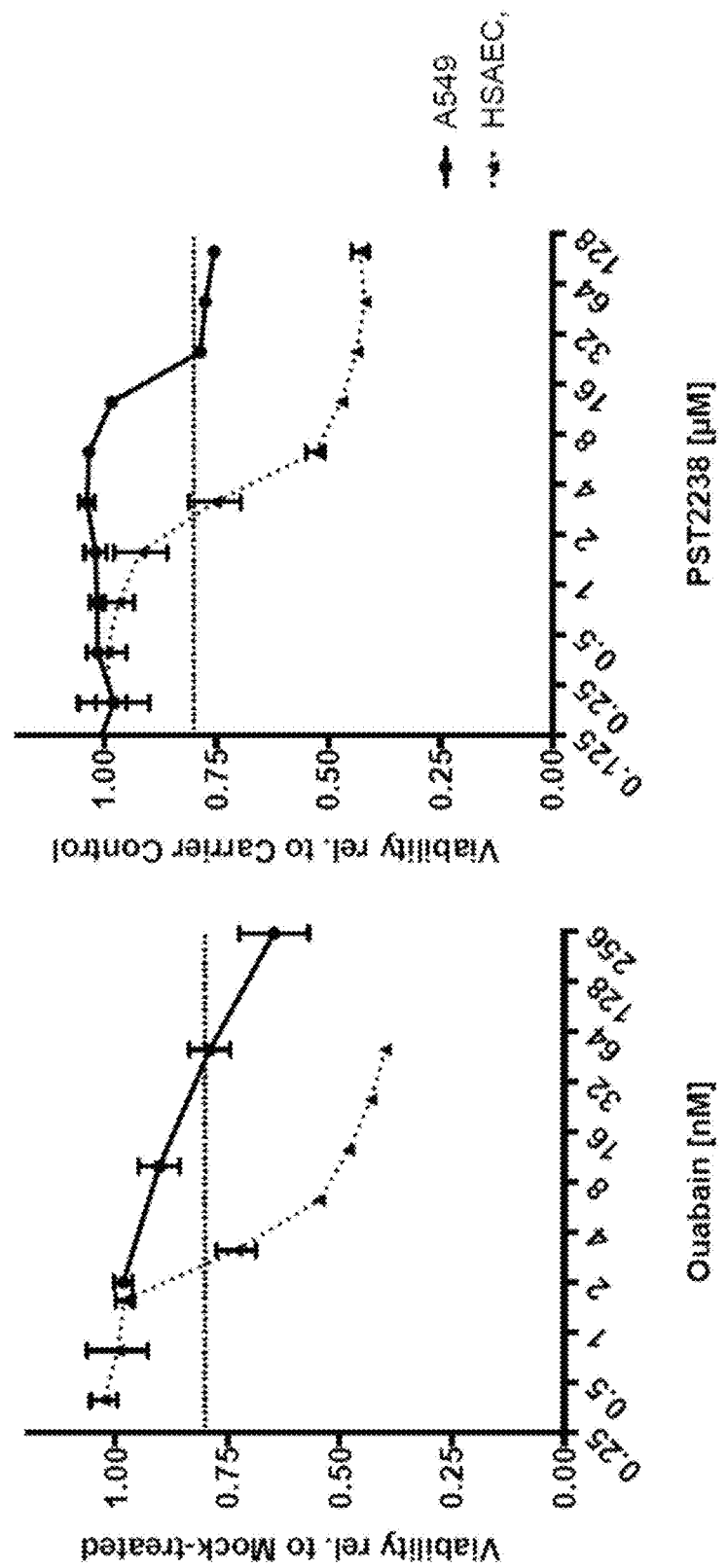

Serial dilutions of ouabain and PST2238 were evaluated for cytotoxicity on A549 cells and the $IC_{50}$ was determined for each (FIG. 15). Concentrations for ouabain (25 nM) and PST2238 (20 μM) were selected that had less than 20% reduction in cell viability 24 h post treatment (FIG. 15C-D), which was the longest treatment period for these studies. The effects of ouabain and PST2238 on ATP1A1 and EGFR expression were analyzed by immunofluorescence microscopy (FIG. 5A) using antibodies specific for ATP1A1 and EGFR. In mock-treated cells, ATP1A1 and EGFR had homogeneous membrane distributions as well as diffuse localization in the cytoplasm (FIG. 5A, left column) After 24 h treatment with ouabain, the ATP1A1 level was greatly reduced (FIG. 5A, middle column, top panel)—due to the removal of cell-surface $Na^+,K^+$ ATPase by clathrin-mediated endocytosis induced by ATP1A1 signaling (Introduction)—while EGFR expression and localization appeared unchanged (FIG. 5A, middle column, bottom panel). On the other hand, PST2238 (FIG. 5A, right panel) had no discernible effect on the expression and localization of ATP1A1 or EGFR: this compound does not cause removal of ATP1A1 because it does not induce ATP1A1 signaling and endocytosis.

Next, ouabain and PST2238 were tested for their effects on RSV infection in an experiment similar to that for the siRNA knock-downs. A549 cells were pre-treated overnight with ouabain or PST2238, inoculated with RSV-GFP (MOI=1 PFU/cell) and incubated with the compounds present throughout. RSV infection was evaluated by (i) GFP expression 17 h p.i. (FIG. 5B), and (ii) the yield of progeny RSV harvested 24 h p.i., quantified by plaque assay on Vero cells (FIG. 5C). Both methods correlated well, and demonstrated a reduction in RSV replication for both compounds that was greater than that achieved with the ATP1A1-specific siRNAs (siRNA2, FIG. 2). Ouabain had the strongest effect: it reduced viral GFP expression by 96% and virus yield by almost 3.0 $\log_{10}$ compared to mock-treated cells. PST2238 reduced viral GFP expression by 89% and virus yield by 2.0 $\log_{10}$ compared to infected cells that did not receive either drug. These findings suggest that RSV infection requires an interaction—either by a viral component or some intermediate—with the extracellular domain of ATP1A1 that can be blocked by ouabain or PST2238. Since PST2238 does not remove ATP1A1 from the cell surface, it likely blocks the signaling function of ATP1A1 through inhibiting RSV triggered ATP1A1 activation.

To determine the stage of RSV infection that is inhibited by the compounds, a "time of addition" experiment was performed. A549 cells were infected with RSV-GFP (MOI=3 PFU/cell), and at different time points ouabain (FIGS. 5 D and E) or PST2238 (FIGS. 5 F and G) were added. Cells were incubated for a total of 24 h p.i. and the viral GFP expression intensity of single, live cells was analyzed by flow cytometry. For both compounds, the strongest inhibitory effect was observed as early as 0 h when the inhibitor was added simultaneously with RSV-GFP showing 85% and 66% reduction of GFP expression by ouabain and PST2238, respectively (FIG. 5 D-G). The inhibition of infection continued to diminish and was almost completely lost at 10 h p.i. These results corroborate with the above described clustering of ATP1A1 (FIG. 3) early during infection to strongly suggest a role for ATP1A1 in an early event of infection i.e., possibly signaling and entry.

Whether PST2238 treatment had any effect on the clustering of ATP1A1 and RSV proteins was also investigated. A549 cells were treated with PST2238 overnight (PST2238 was used because it does not affect the accumulation of ATP1A1), infected with RSV (MOI=5 PFU/cell), incubated for 5 hours, fixed, permeabilized and immunostained as described above with antibodies specific to ATP1A1 and RSV F protein, and visualized by confocal microscopy. PST2238 treatment had no apparent effect on the clustering of ATP1A1. This indicates that clustering of ATP1A1 was not affected by the presence of PST2238 bound to the extracellular domain of ATP1A1. Clustering also did not depend on signaling from ATP1A1, consistent with it being induced early in infection.

Figure 6B:
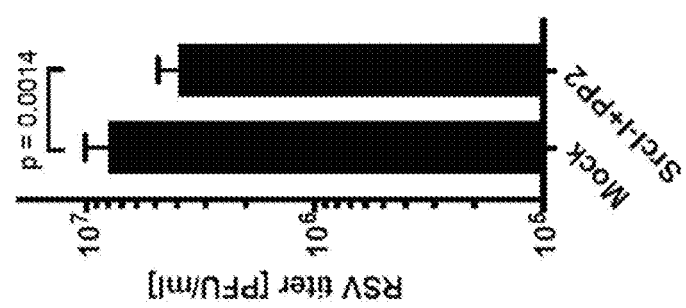
FIGS. 6A and 6B. Src-kinase activity is required for infection. A549 cells were pre-treated with non-toxic concentrations of the indicated Src-kinase inhibitors (PP2 [12.5 µM], SrcI-I [6.25 µM] or both) or mock-treated (DMSO carrier control) for 5 h pre-infection. Cells were inoculated with RSV-GFP (MOI=1 PFU/cell) in media containing the indicated inhibitors.
Figure 6A:
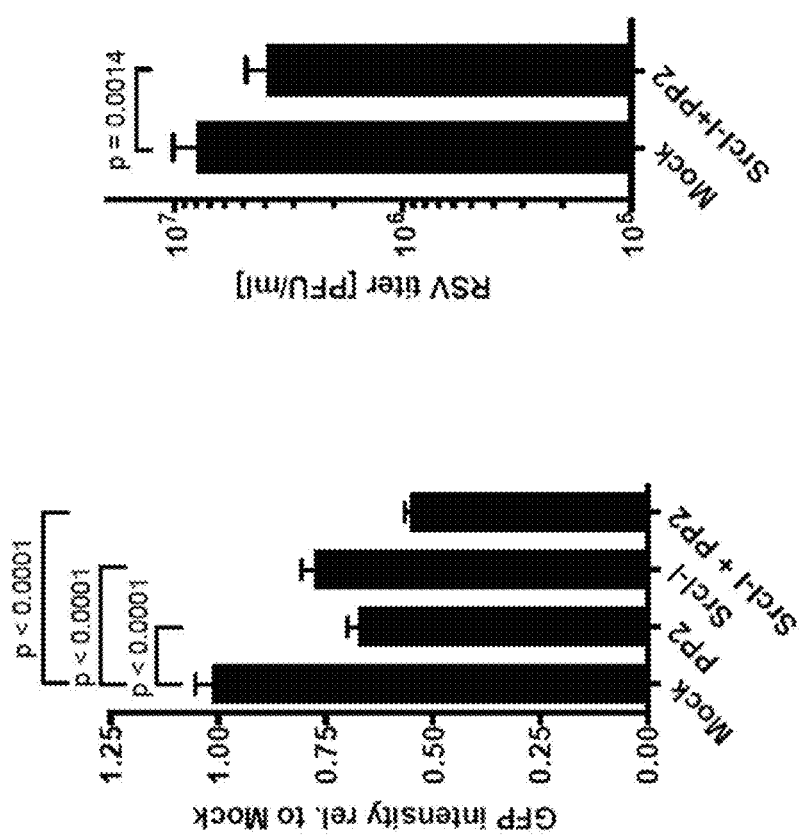

Src-kinase activity is required for RSV entry. The downstream signaling pathways of ATP1A1 that might be involved in ATP1A1 dependent RSV entry was next investigated. As noted above, binding of ouabain to ATP1A1 activates the c-Src-kinase that transactivates EGFR signaling. To test the hypothesis that RSV might use a similar signaling pathway for entry, it was investigated whether c-Src activity is needed for RSV infection by using two Src-kinase inhibitors PP2 and Src-Inhibitor I (SrcI-I). A549 cells were pre-treated with non-toxic concentrations (FIG. 16) of these inhibitors separately or together for 5 h followed by infection with RSV-GFP (MOI=1 PFU/cell) in the continued presence of inhibitors. The efficiency of RSV infection was evaluated by (i) GFP expression at 17 h p.i. for all treatments (FIG. 6A), and (ii) RSV titration at 24 h p.i. for cells that had been treated with both inhibitors (SrcI-I+PP2) (FIG. 6B). Each Src inhibitor showed a modest, but significant (p<0.0001) reduction in GFP intensity of 23% (SrcI-I) and 33% (PP2) relative to mock-treated, infected cells. If added together, the inhibitory effect was additive reaching 45% reduction compared to mock-treated, infected cells. The RSV titer (PFU) for the combined Src-inhibitor treatment showed a 2-fold, significant (two-tailed, unpaired t-test, p=0.0014) reduction compared to mock-treated, infected cells. These data confirmed that Src-kinase activity contributes to RSV infection.

EGFR knock-down reduces RSV infection. Next, it was investigated whether EGFR, a downstream signaling partner of Src kinase, made a contribution to RSV infection. EGFR-specific siRNAs that reduced EGFR expression in A549 cells to 15% at the protein level compared to Neg. siRNA1 48 h p.t., with minimal effect on cell viability were identified. A549 cells were transfected with EGFR-specific, ATP1A1-specific, or control siRNA for 48 h and evaluated by immunofluorescence staining for EGFR and ATP1A1. This showed that the ATP1A1 and EGFR siRNAs greatly reduced the expression of their corresponding target proteins on the plasma membrane (FIG. 7 A, ATP1A1 top panel; EGFR: bottom panel) without affecting EGFR and ATP1A1, respectively, whose expression remained similar to that of Neg siRNA.

Figures 7B, 7C, 7D:
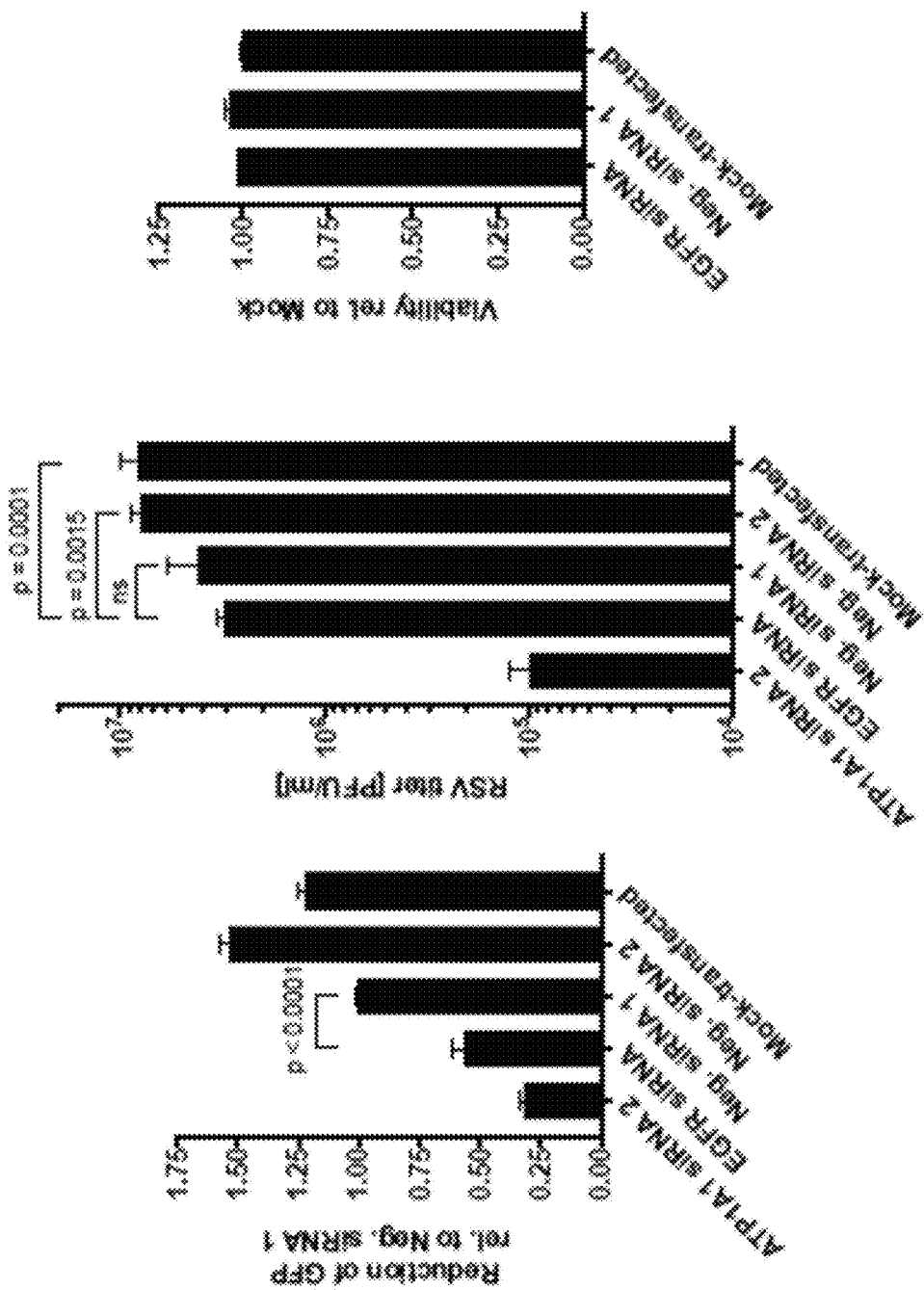

EGFR knock-down cells were infected with RSV-GFP and infection was evaluated by viral GFP intensity quantified by ELISA reader 17 h p.i. (FIG. 7 B) and by plaque titration 24 h p.i. on Vero cells (FIG. 7 C). EGFR knock-down resulted in a nearly 50% reduction in viral GFP expression (FIG. 7B) as compared to Neg. siRNA 1 (p=0.0001). There also was a 38% reduction in RSV titer compared to Neg. siRNA 2 (p=0.0015) or mock-transfected cells (p=0.0001) (FIG. 7 C). There was a modest but consistent reduction in PFU titer for Neg. siRNA1 for unknown reason and hence the reduction in titer for EGFR siRNA treated cells was not significantly lower compared to this particular control siRNA (ns, p=0.9891), but as noted above the reduction in GFP expression was highly significant. None of the siRNAs had an effect on cell viability (FIG. 7 D). Taken together, these data indicate that EGFR plays a role in RSV infection.

EGFR Tyrosine 845 is phosphorylated in response to RSV infection and is ATP1A1 dependent. EGFR phosphorylation during RSV infection was investigated next. As described in FIG. 8, A549 cells were pretreated by transfection with ATP1A1 or Neg. siRNAs, or were pretreated with ouabain or PST2238 or the Src inhibitors SrcI-1+PP2. The cells were then infected with RSV (MOI=5 PFU/cell) and lysates were prepared following 5 h of incubation. The lysates were analyzed using an EGFR phosphorylation array to identify the EGFR sites that were phosphorylated during infection.

The array contained phosphospecific antibodies against 17 different specific sites of the human EGFR family, plus a positive control antibody that binds EGFR irrespective of phosphorylation, which were spotted on nitrocellulose membrane. Replicate membranes were incubated with the different cell lysates, and captured EGFR was quantified by a second, biotinylated, antibody against EGFR (pan EGFR), followed by horseradish peroxidase conjugated streptavidin, and luminescence detection by an X-ray film. The spot intensity values were normalized to internal array controls and to the total amount of EGFR present in the lysates. Values are reported relative to Neg. siRNA 1 (for siRNA treated) or to mock-treated infected (for inhibitor treated) cells.

Figure 8A:
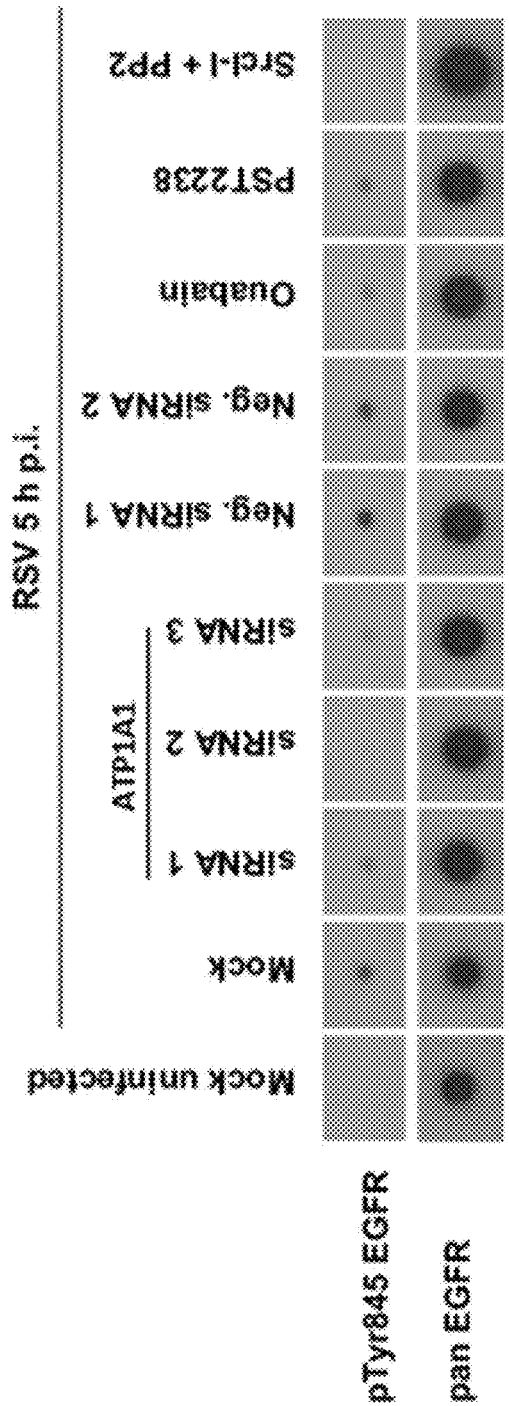
FIGS. 8A-8D. ATP1A1 dependent EGFR phosphorylation at Tyr845 during RSV infection. A549 cells were treated as indicated (either siRNA knock down for 48 h or pre-treatment with the chemical compounds ouabain [25 nl\4], PST2238 [40 µM] or Src Inhibitor-I (SrcI-I) [6.25 µM] and PP2 [12.5 µM] for 5 h pre-inoculation). Cells were serum starved overnight, before they were inoculated with wt RSV (MOI=5 PFU/cell) and incubated at 37° C. Cells were lysed 5 h p.i. and subjected to a phospho-specific EGFR array (RayBiotech, Inc.).
Figure 8D:
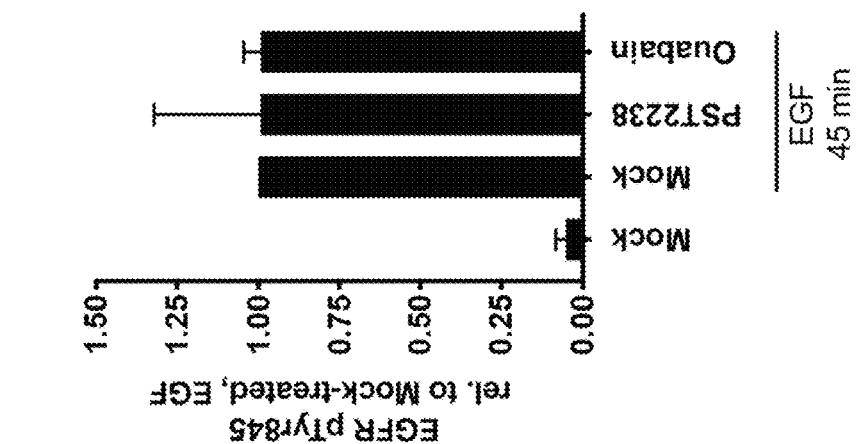
Figure 8C:
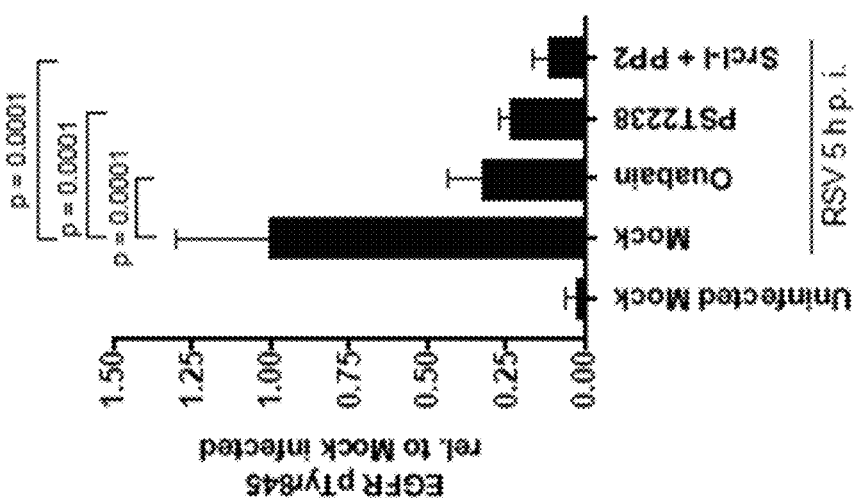
Figure 8B:
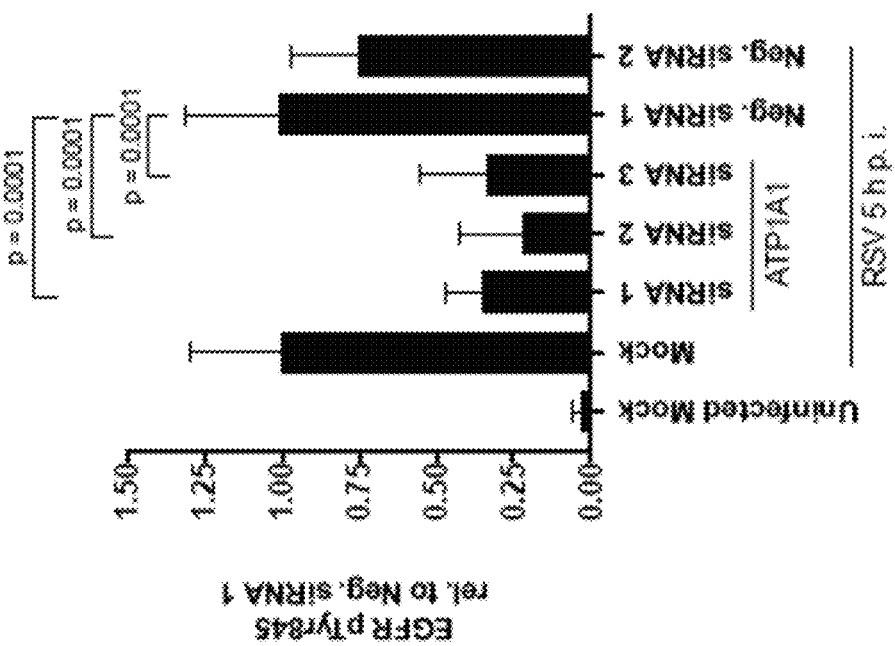

EGFR in lysates of uninfected A549 cells had detectable phosphorylation at Thr686 and Ser1113 (FIG. 17). EGFR in RSV-infected cells contained a similar amount of phosphorylation at these two sites, and in addition was phosphorylated at Tyr845 (FIG. 8 and FIG. 17A). The level of pTyr845 was significantly (p<0.0001) reduced in the ATP1A1 siRNA knock-down cells, to an average of 35% (siRNA1), 22% (siRNA2), and 33% (siRNA3) relative to Neg. siRNA1 (FIG. 8B). The phosphorylation of Tyr845 in RSV-infected cells was similar to Neg. siRNA1. While it was slightly reduced for Neg. siRNA2, the difference was not significant (p=0.3651) compared to Neg. siRNA1. Consistent with the ATP1A1 knock-down, a significant reduction in Tyr845 phosphorylation also was observed when the cells were pre-treated with ouabain, PST2238, or Src-kinase inhibitors (SrcI-I+PP2) prior to infection with RSV (FIG. 8 C). For ouabain- and PST2238-treated cells, the level of pTyr845 was reduced to 27% and 26%, respectively, compared to mock-treated RSV infected cells; the reduction was similar to that observed for ATP1A1 knock-down. To confirm a lack of a direct inhibitory effect of Ouabain or PST2238 on EGFR, A549 cells were pre-treated with PST2238 or Ouabain and stimulated with EGF for 45 min. The EGF-induced phosphorylation of pTyr845 indeed was not affected by the compounds as compared to mock-treated cells (FIG. 8D). Inhibiting the Src-kinases (SrcI-I+PP2) reduced phosphorylation at Tyr845 to 12% compared to mock-treated, infected cells (FIG. 8C). Thus, phosphorylation at EGFR Tyr845 could be reduced either by decreasing ATP1A1 expression or by ATP1A1- or Src-specific inhibitors. This suggested that EGFR pTyr845 is ATP1A1-dependent and that Src kinase serves as a signaling effector to transactivate EGFR by Tyr845 phosphorylation.

Figure 9A:
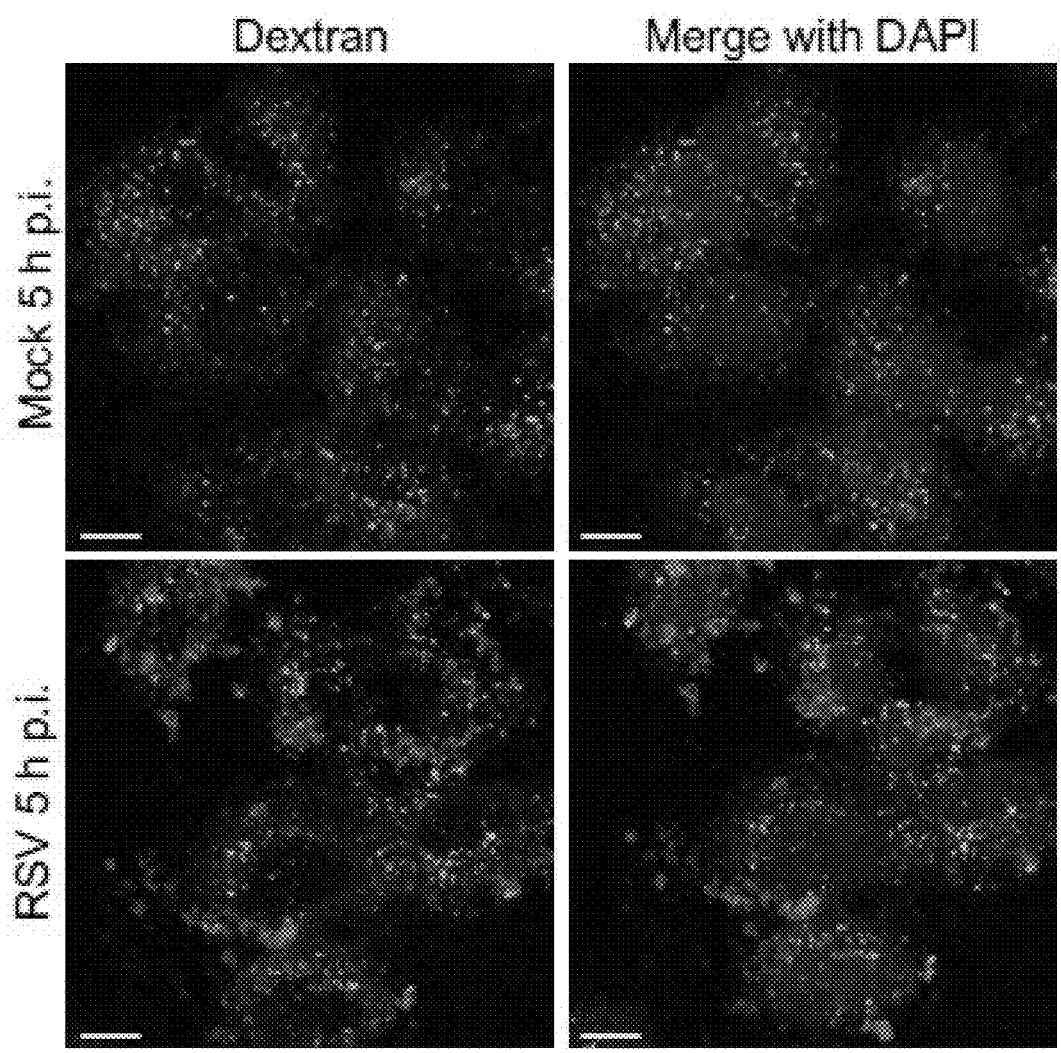

Macropinocytosis is induced by RSV and is mediated by ATP1A1. EGFR signaling is known to cause actin rearrangement, membrane ruffling, and activation of endocytosis and macropinocytosis (Donepudi et al., *Cellular Signalling.* 2008; 20(7):1359-67; Swanson et al., *Trends Cell Biol.* 1995; 5(11):424-8; Hewlett et al., *J Cell Biol.* 1994; 124(5): 689-703). Macropinocytosis is an unspecific, fluidic uptake at the cell surface that initiates through actin rearrangement and membrane ruffling. Limited prior evidence suggested macropinocytosis as a mode of RSV entry (Krzyzaniak et al., *PLoS Pathogens.* 2013; 9(4):e1003309; Mehedi et al., *PLOS Pathogens.* 2016; 12(12):e1006062). In the present study, a fluorescent dye-conjugated dextran was used as a fluidic uptake marker, visualized with fluorescence confocal microscopy, to assess macropinosome formation and the role of ATP1A1 in this process. A549 cells were infected with wt RSV (MOI=5 PFU/cell) in the presence of Alexa Fluor 568-conjugated Dextran (10,000 MW). At 5h p.i., cells were washed and fixed, nuclei were counterstained with DAPI, and the uptake of dextran was analyzed by fluorescence confocal microscopy. Cells that had been mock-infected were found to contain dextran-positive vesicles that were small, round, and homogeneous in size of an average volume of ~0.5 $\mu m^3$ (FIG. 9A, top panel) and reflect the basal level of dextran uptake. This phenotype changed dramatically by 5 h after infection with wt RSV (FIG. 9A, bottom panel). The dextran positive vesicles were much bigger (average volume of ~5.7 $\mu m^3$), irregular in shape, and reflected the typical morphology of macropinosomes. This showed that RSV infection induces macropinocytosis.

Next, A549 cells were infected with RSV in the presence of dextran-AF568 and at 5 h p.i. were co-stained for ATP1A1 (Alexa Fluor 488; green) and RSV-N (marker of RSV virions) (Alexa Fluor 647; red) and visualized them along with dextran (Alexa Fluor 568; cyan) by fluorescence confocal microscopy. As previously noted, 5 h p.i. is very early in RSV infection, and the N protein that is detected would be mainly from the input virus particles, as was shown with UV-inactivated virus. Clusters of ATP1A1 were observed co-localized with RSV N protein in the dextran-positive macropinosomes (FIG. 9B, indicated by arrows), indicating that RSV was indeed taken up by macropinocytosis. Co-staining for RSV F and N was also performed and showed that both proteins were co-localized in the dextran-positive macropinosomes (FIG. 9 C). The presence of RSV F suggests that the RSV detected in the macropinosomes was enveloped, indicating that fusion and release of nucleocapsid presumably occurred subsequently in internal vesicles rather than at the plasma membrane.

Figure 9D:
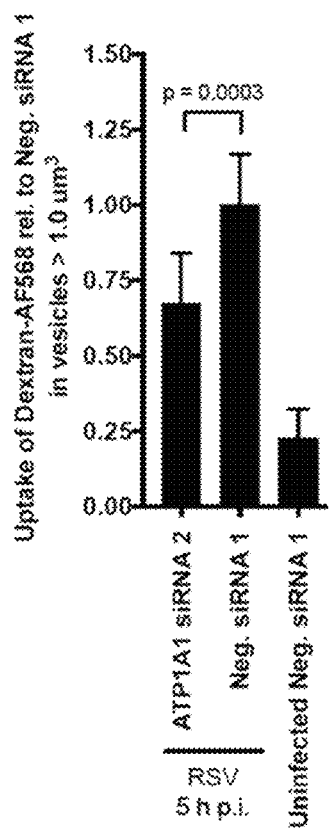
Figure 9E:
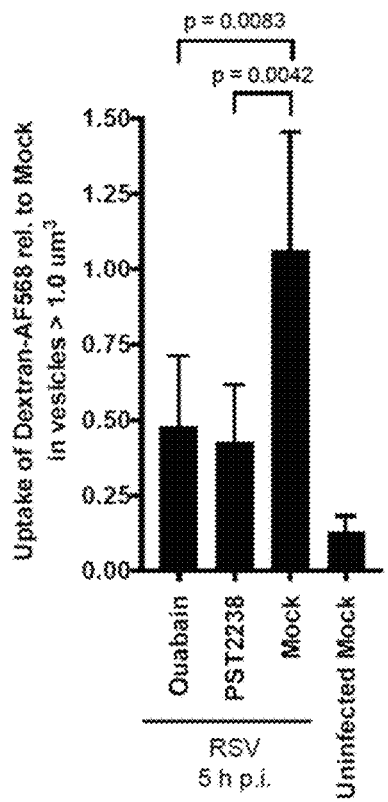
Figure 9F:
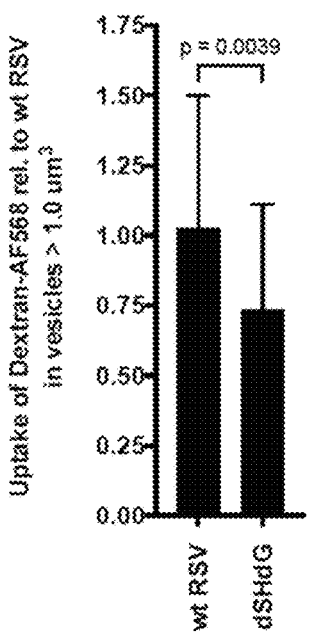

To examine the role of ATP1A1 in this putative uptake mechanism, ATP1A1 expression was knocked down with siRNA, or the cells were treated with ouabain or PST2238, followed by infection with RSV (MOI=5 PFU/cell) in the presence of dextran-AF568, followed by fluorescence confocal microscopy to quantify macropinosomes. Multiple random Z-stack images were acquired by confocal microscopy and the total amount of dextran uptake was quantified. Dextran-positive vesicles were detected by Imaris imaging software, and the total fluorescence intensity per vesicle was determined. Vesicles smaller than 1.0 $\mu m^3$ were excluded to omit the basal level of dextran uptake and to focus on the large vesicles that are typical for macropinosomes. The total intensity of dextran vesicles larger than 1.0 $\mu m^3$ was determined per field, normalized to the number of nuclei and expressed relative to Neg. siRNA1 or mock-treated cells (FIG. 9D). Dextran uptake was increased 4-fold in RSV-infected as compared to uninfected cells, which had both been transfected with Neg. siRNA1 (FIG. 9D), confirming the visual observation of increased dextran-AF568 uptake (FIG. 9A). On the other hand, knock-down of ATP1A1 caused a significant (P=0.0003) reduction of 33% compared to Neg. siRNA1 (FIG. 9D). Ouabain and PST2238 caused an even greater reduction in RSV-induced macropinosomes, to less than 50% compared to mock-treated, RSV-infected cells (FIG. 9E). Since RSV G was suggested to be important for triggering ATP1A1 activation, based on the loss of clustering observed with the dSH/dG mutant as described previously in FIG. 4, the macropinosomes in cells infected with wt RSV or dSH/dG RSV mutant were also quantified. This showed that macropinosome formation indeed was significantly (P=0.0039) reduced for the dSH/dG virus as compared to wt RSV, consistent with a role for the G protein in activating the pathway leading to macropinosome formation.

Signaling from ATP1A1 also can induce clathrin-mediated endocytosis (Introduction), and this endocytic pathway has been controversially suggested to be involved in RSV entry (Kolokoltsov et al., *J Virol.* 2007; 81(14):7786-800). However, preliminary studies using an inhibitor of clathrin-mediated endocytosis (e.g., chlorpromazine) did not detect effects on RSV infection at non-toxic concentrations, and this was not pursued further.

Figure 16:
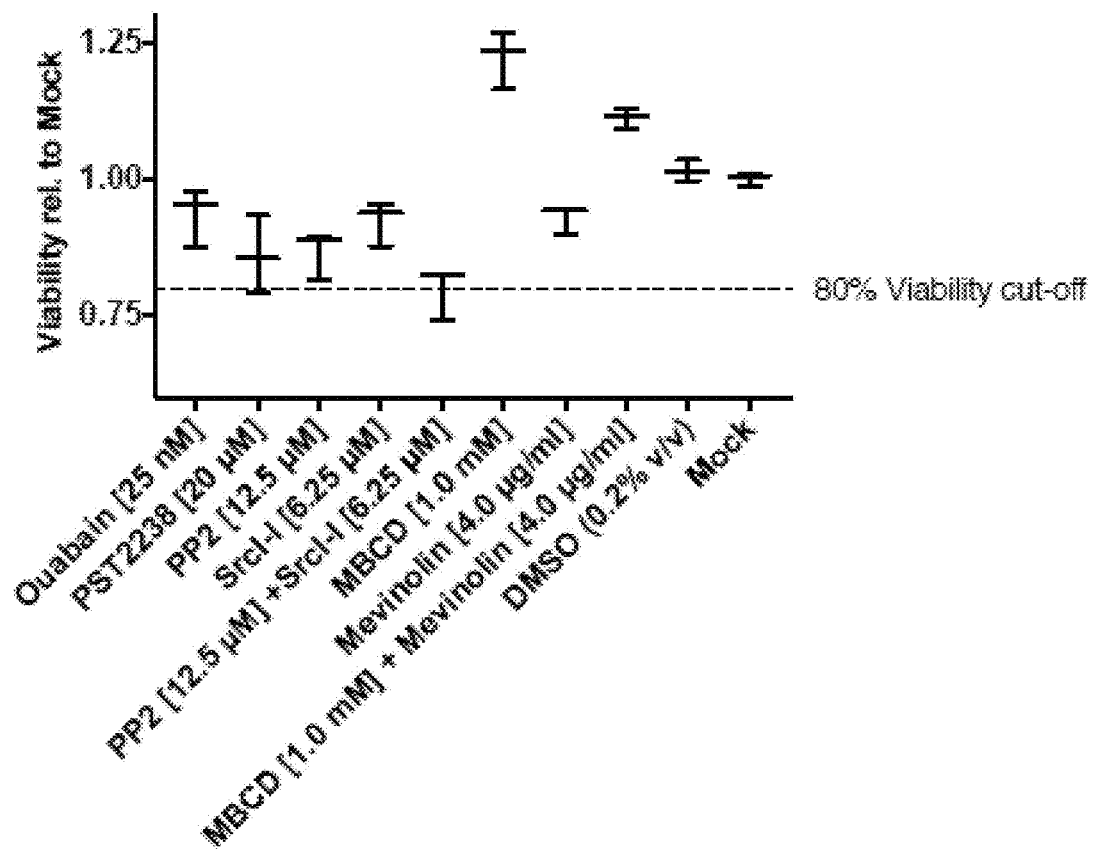
FIG. 16. Cytotoxicity analyses of chemical compounds on A549 cells. A549 cells were treated for 24 h with each compound at the highest concentrations used in this study. Cell viability was determined in triplicates for each compound by the ATP based viability assay CELLTITER-GLO® (PROMEGA®) and changes in viability are reported as fold change relative to mock-treated cells with error bars indicating the standard deviation.

Cholesterol is required for RSV uptake and signaling. As described above, ATP1A1-Src-EGFR signaling characteristically is associated with caveolae. The structural integrity of caveolae depends on the presence of cholesterol, and its depletion with a cholesterol-sequestering drug, such as methyl-beta-cyclodextrin (MBCD), disrupts caveolae from the plasma membrane (Rothberg et al., *Cell.* 1992; 68(4): 673-82; Hailstones et al., *J Lipid Res.* 1998; 39(2):369-79). The impact of depleting cholesterol in A549 cells prior to RSV infection was therefore evaluated, which was done using MBCD and Mevinolin, individually or in combination at non-cytotoxic concentrations (FIG. 16). MBCD removes cholesterol from the plasma membrane whereas Mevinolin inhibits its biosynthesis and prevents replenishing the plasma membrane with cholesterol.

First, cholesterol-depleted A549 cells were infected with RSV-GFP and it was found that GFP expression at 17 h p.i. was reduced to approximately 50% with each of the depletions, compared to control infected cells (FIG. 10A). Next, the level of RSV-induced macropinocytosis in cholesterol-depleted cells was quantified by dextran-AF568 uptake into large vesicles. In RSV-infected cells, dextran uptake was reduced by each of the cholesterol-depletion treatments, with the most significant (p<0.0001) reduction of 59% observed for the combined MBCD-Mevinolin treatment (FIG. 10B). The phosphorylation of EGFR Tyr845 also was determined in RSV-infected cells pretreated with MBCD+Mevinolin. A modest but significant (two tailed t-test, p=0.0163) reduction in pTyr845 was observed (FIG. 10C). These results show that cholesterol depletion results in reduced EGFR transactivation, reduced macropinocytosis, and reduced RSV infection, consistent with caveolae as the site of ATP1A1 signaling.

Figure 11D:
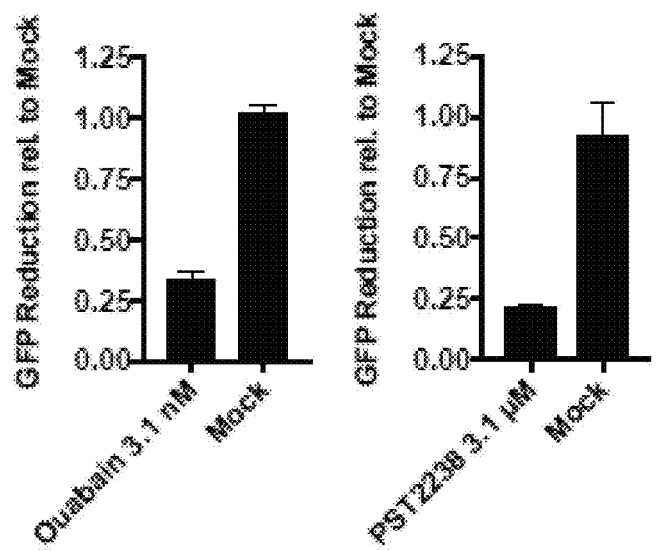
Figure 11E:
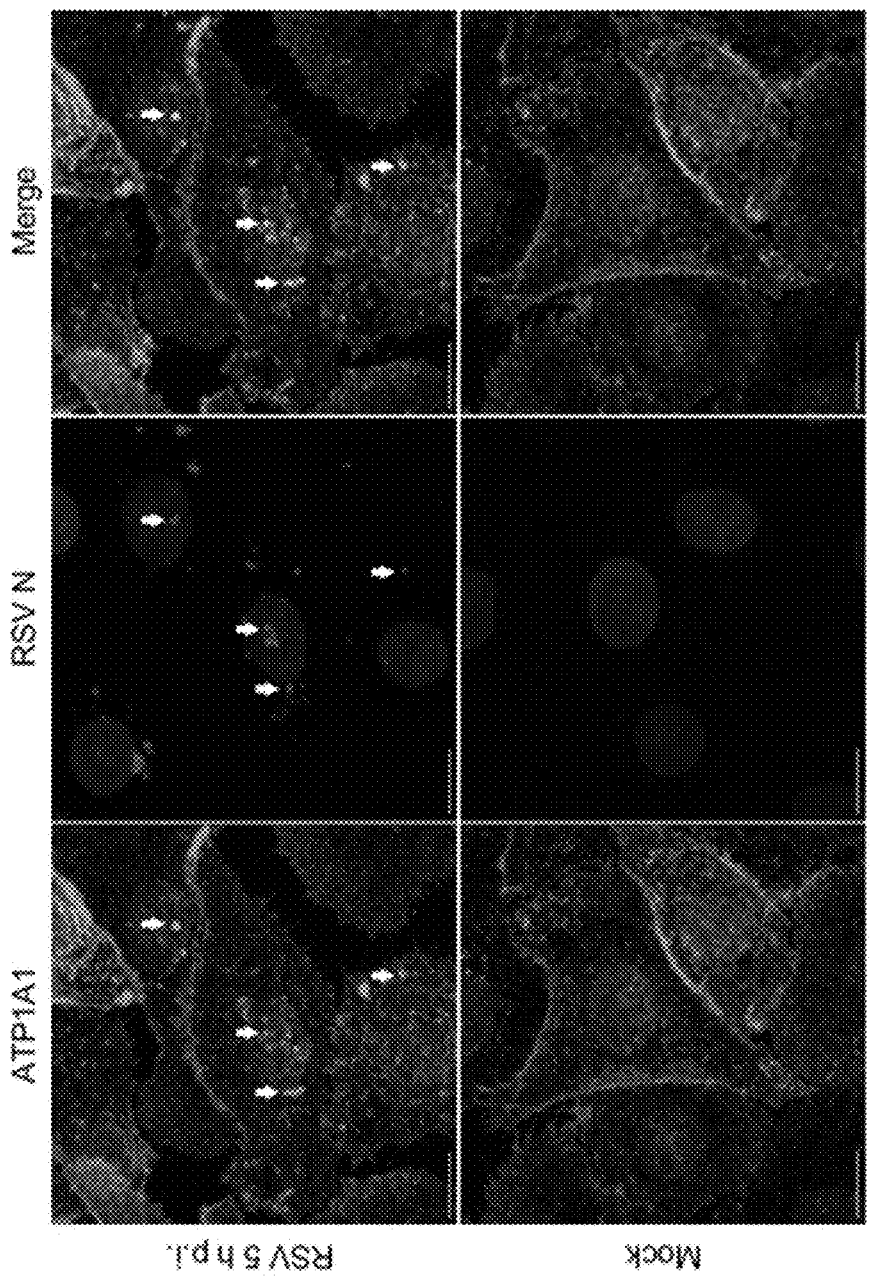

Validation of findings in primary human small airway epithelial cells and differentiated human airway epithelial air-liquid interface (HAE-ALI) cultures. All experiments described above were performed with the human airway epithelial A549 cell line. Some of the major findings were confirmed using primary human small airway epithelial cells (HSAEC) from a 16 yr old healthy male donor. SiRNA transfection knocked down expression of ATP1A1 protein to 25-30% compared to Neg. siRNA 1 (FIG. 11A) which was somewhat more than the reduction of 35-39% observed for A549 cells. Following the same protocols as for A549 cells, it was found that (i) knockdown of ATP1A1 reduced the expression of RSV-GFP to 29-42% of the negative control (FIG. 11B), similar to what was observed with A549 cells (FIG. 2A). (ii) Phosphorylation of EGFR Tyr845 was also significantly (p=0.0038) reduced in ATP1A1 knock down (siRNA2) HSAEC (FIG. 11C), similar to what was seen in A549 cells (FIG. 8). (iii) The inhibitory effects of ouabain and PST2238 on the expression of RSV-GFP were even stronger in HSAEC than in A549 cells (FIG. 11D). $IC_{50}$ titrations of the compounds on HSAEC for RSV-GFP expression showed that the values were lower (i.e., more effective inhibition) in HSAEC than A549 cells by 4.9-fold for ouabain (FIG. 15A) and 8.2-fold for PST2238 (FIG. 15B). (iv) RSV-induced ATP1A1 clustering and colocalization of ATP1A1 and RSV N also was observed in HSAEC (FIG. 11E), similar to A549 cells (FIG. 3). Thus, the experiments performed in primary HSAEC cells confirmed the results obtained in the A549 cell line.

Figure 18A:
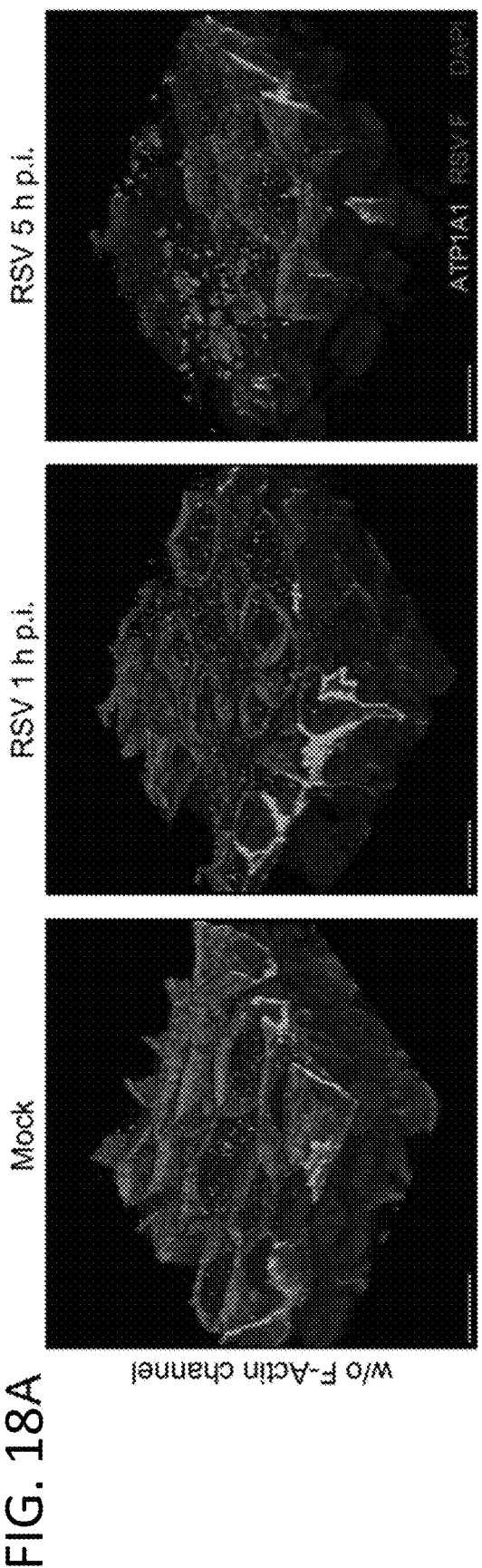
FIGS. 18A and 18B. RSV induces ATP1A1 clustering in primary human airway epithelial-air liquid interface (HAE-ALI) cultures. HAE-ALI cultures were inoculated with wt RSV (106 PFU/tissue), incubated for 1 or 5 h, fixed and subjected to immunofluorescence staining as described for A549 cells in FIG. 3 (ATP1A1, green; RSV F, red; F-Actin, cyan; DAPI; blue) Images are shown without (FIG. 18A) and with (FIG. 18B) F-Actin staining. Scale bars 10 µm.
Figure 18B:
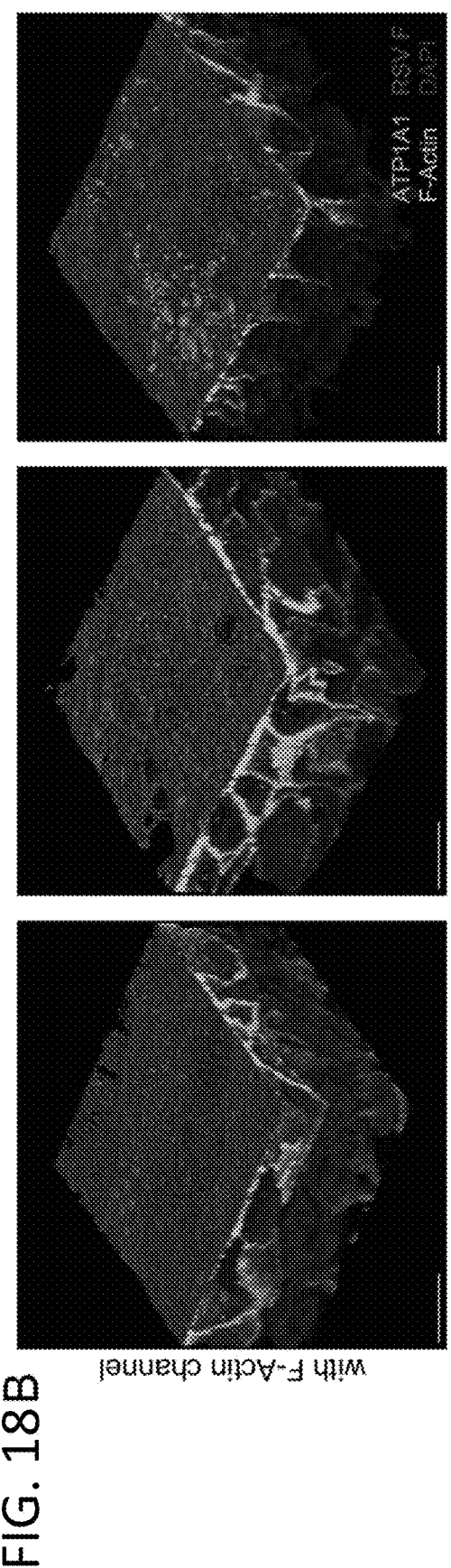

In addition, we used HAE-ALI cultures, a model of primary, differentiated, polarized mucociliary airway epithelium, to investigate the localization of ATP1A1 and to confirm the phenomenon of RSV-induced ATP1A1 clustering. Cells were infected with wt RSV ($10^6$ PFU/transwell), incubated for 1 h or 5 h, fixed with PFA, permeabilized with TRITON™ X-100, and immunostained for RSV F (red) and ATP1A1 (green), as described for A549 cells in FIG. 3. The apical surface was demarcated by staining for F-actin (cyan) since it is abundant beneath the apical membrane and provides a close estimation of the apical surface location. To visualize ATP1A1 location, three-dimensional sections are shown without (FIG. 18A) and with (FIG. 18B) F-actin staining. In mock treated cells, ATP1A1 was predominantly present in the basolateral surfaces of cells with relatively smaller amounts present on the apical surface in a spotted distribution (FIG. 18, left column). Upon infection with RSV, ATP1A1 clusters were visible as early as 1 h p.i. (FIG. 18, middle column), which became more noticeable and larger at 5 h p.i. (FIG. 18, right column) The apical ATP1A1 seemed to increase in amount over time following infection, suggesting its recruitment to the apical surface. The ATP1A1 clusters were mostly visible in close proximity to RSV F. These observations were similar to those in A549 cells (FIG. 3), confirming that RSV-induced ATP1A1 clustering could be reproducibly demonstrated in different primary cell systems.

Discussion

In the present study, the host proteins involved in RSV infection were investigated by performing a genome-wide high-throughput siRNA screen in human airway A549 cells infected with a recombinant RSV that expresses GFP. Knockdown of the cellular gene encoding the protein ATP1A1 provided the greatest reduction in GFP expression, as a surrogate for RSV transcription and replication, with minimal effects on cell viability. ATP1A1 is the major subunit of $Na^+K^+$ ATPase, a transmembrane complex that is an ATPase, an ion channel, and also is involved in signal transduction (Reinhard et al., *Cell Mol Life Sciences*: CMLS. 2013; 70(2):205-22) leading to clathrin-mediated endocytosis that removes $Na^+K^+$ ATPase from the plasma membrane for lysosomal destruction (Cherniaysky-Lev et al., *J Biol Chem*. 2014; 289(2):1049-59). In this study, evidence is provided that ATP1A1 is involved in RSV entry, and that the signal transduction function of ATP1A1 is needed for efficient RSV infection.

Treatment with the cardiotonic steroid ouabain, which acts specifically on ATP1A1, reduced the efficiency of RSV infection. Inhibition of RSV infection with ouabain was achieved at sub-nanomolar concentrations that initiate ATP1A1 signaling cascades (Reinhard et al., *Cell Mol Life Sciences*: CMLS. 2013; 70(2):205-22; Xie et al., *Mol Interv.* 2003; 3(3):157-68) but are not inhibitory for its ATPase and ion channel functions and do not alter the cytosolic $Na^+$ and $K^+$ levels (Liu et al., *J Biol Chem*. 2000; 275(36):27838-44). While incubation with ouabain depletes $Na^+K^+$ ATPase over time from the plasma membrane, it is unlikely that this depletion accounts for the inhibition of RSV infection, because the antiviral effect of ouabain was evident even when added simultaneously with the virus inoculum. Treatment with PST2238 also reduced the efficiency of RSV infection. PST2238 is a competitive inhibitor of ouabain that shares a common binding site on the extracellular domain of ATP1A1. PST2238 blocks ouabain binding as well as ATP1A1 signaling in response to ouabain or RSV, and does not induce signaling or endocytosis. Given these major differences—that ouabain is an ATP1A1 agonist and PST2238 is a competitive ATP1A1 antagonist—it was surprising that both compounds inhibited RSV infection. Time-of-addition experiments indicated that the inhibitory effects of ouabain and PST2238 occurred very early during infection, consistent with some step prior to activation of ATP1A1 and viral entry.

A striking phenomenon was observed in which ATP1A1 formed clusters in the plasma membrane within a few hours following infection with RSV. This clustering was not affected by treatment with PST2238, which is consistent with clustering being triggered very early in infection, preceding rather than following ATP1A1 signaling. Clustering of ATP1A1 also occurred with UV-inactivated RSV and thus was independent of transcription of the complete genome, viral RNA replication, and viral replication. This clustering was reminiscent of the behavior of signaling receptors following ligand binding, and suggested there might be a physical interaction between the virions and the cell surface that triggers ATP1A1 clustering. This might be part of viral attachment or part of a cellular response to RSV virions. However, physical interaction between ATP1A1 and any of the RSV surface glycoproteins (G, F or SH) was not detected by co-immunoprecipitation techniques. It may be that an interaction between ATP1A1 and one or more RSV proteins occurs but is insufficiently stable to be detected by these methods. Using RSV deletion mutants, it was demonstrated that RSV G protein is required to trigger ATP1A1 clustering. This implies that an initial virus attachment event involving G is needed to initiate ATP1A1 clustering. That initial attachment event might involve a direct interaction between RSV G and ATP1A1, although there is as yet no evidence of this. It perhaps is more likely that RSV attachment is an earlier event involving other cellular structures, and that attachment induces ATP1A1 signaling through some as-yet unknown intermediate step. Clustering of signaling receptors in general can increase ligand binding and signal transduction (Chu et al., *Biochem J.* 2004; 379(Pt 2):331-41) by reducing the effective dissociation rate through enhancing rebinding within the receptor cluster (Gopalakrishnan et al., *Biophys J.* 2005; 89(6):3686-700). Therefore, clustering of ATP1A1 may be beneficial for RSV infection by enhancing the ATP1A1-mediated signaling that is required for viral uptake.

It was hypothesized that RSV utilizes ATP1A1 signaling for uptake into the cell by endocytosis. This could involve any of various pathways including clathrin- or caveolin-mediated endocytosis and macropinocytosis. RSV infection indeed induces and requires ATP1A1 signaling. For example, Src-kinase activity was induced by RSV infection, and inhibition of c-Src reduced the efficiency of infection. Also, EGFR is involved in RSV infection, as previously shown (Krzyzaniak et al., *PLoS Pathogens.* 2013; 9(4): e1003309), but is not sufficient alone and requires the upstream activation of ATP1A1 and c-Src for efficient RSV infection. This was indicated by the observation that phosphorylation of EGFR Tyr 845 (i) occurred early during RSV infection, detectable by 5 h p.i., (ii) was dependent on ATP1A1, e.g., was significantly reduced in cells whose ATP1A1 expression was knocked down with siRNAs or in which ATP1A1 activity was reduced by treatment with ouabain or PST2238, and (iii) was dependent on Src kinase, the downstream signaling effector of ATP1A1. Inhibition of the Src kinase activity abolished phosphorylation of EGFR Tyr845 below the detectable levels, suggesting that this phosphorylation is mediated by ATP1A1-activated Src kinase.

Ouabain-induced, ATP1A1-mediated signaling cascades have been reported to take place in the cholesterol-rich microdomains called caveolae (Wang et al., *J Biol Chem.* 2004; 279(17):17250-9; Liu et al., *Am J Physiol Cell Physiol.* 2003; 284(6):C1550-60), which are thought to serve as a region to integrate multiple signaling pathways by concentrating signaling proteins and creating temporal and spatial patterns of cell regulation (Ostrom et al., *J Biol Chem.* 2001; 276(45):42063-9). Many proteins associated with signaling functions are present in the caveolae, including ATP1A1, EGFR and c-Src. It has also been described that cholesterol is needed for the ouabain-induced ATP1A1-Src-EGFR signaling cascade, and that depletion of cholesterol reduced the recruitment of c-Src and therefore reduced ATP1A1 signaling (Wang et al., *J Biol Chem.* 2004; 279 (17):17250-9). Interestingly, it has been reported that the cholesterol rich lipid rafts are required as docking platform for RSV entry (San-Juan-Vergara et al., *J Virol.* 2012; 86(3):1832-43). In the present example, depletion of cholesterol with MBCD and Mevinolin indeed reduced the efficiency of RSV infection, consistent with the signaling by ATP1A1, c-Src, and EGFR taking place in caveolae.

As noted, ATP1A1 signaling in response to ouabain results in clathrin-mediated endocytosis and the uptake and destruction of $Na^+K^+$ ATPase, and clathrin-mediated endocytosis also has been suggested to be involved in the uptake of RSV (Kolokoltsov et al., *J Virol.* 2007; 81(14):7786-800). In preliminary experiments in the present study, inhibitors of clathrin-mediated endocytosis did not affect RSV infection. However, RSV infection was found to induce a high level of macropinocytosis, and that these macropinosomes contained a high content of RSV virions. Previous studies also have suggested a role for macropinocyosis in RSV uptake (Krzyzaniak et al., *PLoS Pathogens.* 2013; 9(4):e1003309; Mehedi et al., *PLOS Pathogens.* 2016; 12(12):e1006062). In addition, it has been described that phosphorylation of EGFR Tyr845 by c-Src, in an EGF-independent manner, can lead to induction of macropinocytosis (Donepudi et al., *Cellular Signalling.* 2008; 20(7):1359-67; Biscardi et al., *J Biol Chem.* 1999; 274(12):8335-43), Src kinase activity plays an important role during macropinosome formation and trafficking (Kasahara et al., *J Cellular Physiol.* 2007; 211(1):220-3), and it can synergistically enhance macropinocytic induction. Based on these observations, it is believed that, upon RSV binding, ATP1A1-signaling is induced, transactivates EGFR via Src and induces the macropinocytic uptake of RSV. Typical macropinosomes are formed as a result of extensive, unspecific fluidic uptake at the plasma membrane that engulfs fluid and solid cargo from outside of the cell into cytoplasmic vesicles. They are heterogeneous in size and are larger than other endocytic vesicles with diameters of 0.5-5 µm. Macropinosome formation was visualized and quantified with fluorochrome-conjugated dextran as a fluidic marker, excluding vesicles that were smaller than 1 $µm^3$ that would be categorized as endosomes. RSV infection clearly induced extensive macropinocytosis very early on infection. Macropinosome formation under these conditions was confirmed to be dependent upon ATP1A1, and was significantly reduced if the membrane ATP1A1 expression was decreased or if the cells were treated with ouabain or PST2238. Depletion of cholesterol resulted in a decrease in the formation of macropinosomes, consistent with the involvement of signaling complexes in the caveolae. In addition, immunostaining revealed the co-localization of ATP1A1, RSV F protein (marker of viral envelope) and RSV N protein (marker of viral nucleocapsid), and dextran in macropinosomes. This supports a model in which RSV virions are taken up by the macropinosome, and membrane fusion and release of the nucleocapsid presumably taking place at a later step after the macropinocytic uptake. It was surprising that both ouabain and PST2238 inhibited RSV infection, since they have opposite effects on ATP1A1 signaling, namely that ouabain induces and PST2238 inhibits. The mechanism by which PST2238 inhibits RSV seems straight-forward: specifically, blockade of RSV-induced ATP1A1 signaling. The mechanism by which ouabain inhibits RSV is less clear, since both ouabain and RSV individually induce ATP1A1 signaling. A non-limiting explanation is that the signaling cascades induced by ouabain versus RSV are not exactly the same. For example, the outcomes of the signaling cascades are different: ouabain-induced signaling results in clathrin-mediated endocytosis, whereas RSV-induced signaling results in macropinocytosis. Also, we could readily detect phosphorylation of EGFR Tyr845 following infection with RSV, but not following treatment with ouabain, suggestive of a quantitative or qualitative difference in EGFR phosphorylation. Thus, while signaling through ATP1A1 by ouabain versus RSV may involve a number of steps in a common signal transduction pathway located in the caveolae, it suggests that the ouabain-induced signaling cascade from ATP1A1 not only is different from that of RSV, but also competes with and thereby inhibits ATP1A1 signaling induced by RSV.

ATP1A1 also has been implicated as a pro-viral factor in the infection cycles of Ebola virus (Garcia-Dorival et al., *J Proteome Res.* 2014; 13(11):5120-35), coronavirus (Burkard et al., *J Virol.* 2015; 89(8):4434-48), hepatitis C virus (Lussignol et al., *PNAS.* 2016; 113(9):2484-9), and mammarenaviruses (Iwasaki et al., *PLoS Pathogens.* 2018; 14(2): e1006892), but the nature and mechanism of its involvement for those viruses remains largely unknown. In the present study, it is demonstrated that VSV infection was not inhibited by ATP1A1 knock-down, indicating that the effect is specific to particular viruses and does not involve a general inhibitory cellular effect. Ouabain has been described to have anti-viral properties for several viruses, namely herpes simplex virus, CHIKV, HIV, adenovirus, and porcine reproductive and respiratory syndrome virus 1 (Dodson et al., *Virology.* 2007; 366(2):340-8; Su et al., *Antiviral Res.* 2008; 79(1):62-70; Ashbrook et al., *mBio.* 2016; 7(3); Wong et al., *PLoS pathogens.* 2013; 9(3):e1003241; Grosso et al., *J Virol.* 2017; 91(3); Karuppannan et al., *Antiviral Res.* 2012; 94(2): 188-94), but the mechanism of inhibition was not conclusively identified. PST2238 has not previously been shown to have anti-viral activity against any virus, including RSV. It is believed that PST2238 also inhibits the replication of other viruses that are ouabain-sensitive or that are using the ATP1A1-Src-EGFR signaling cascade for entry.

Figure 12:
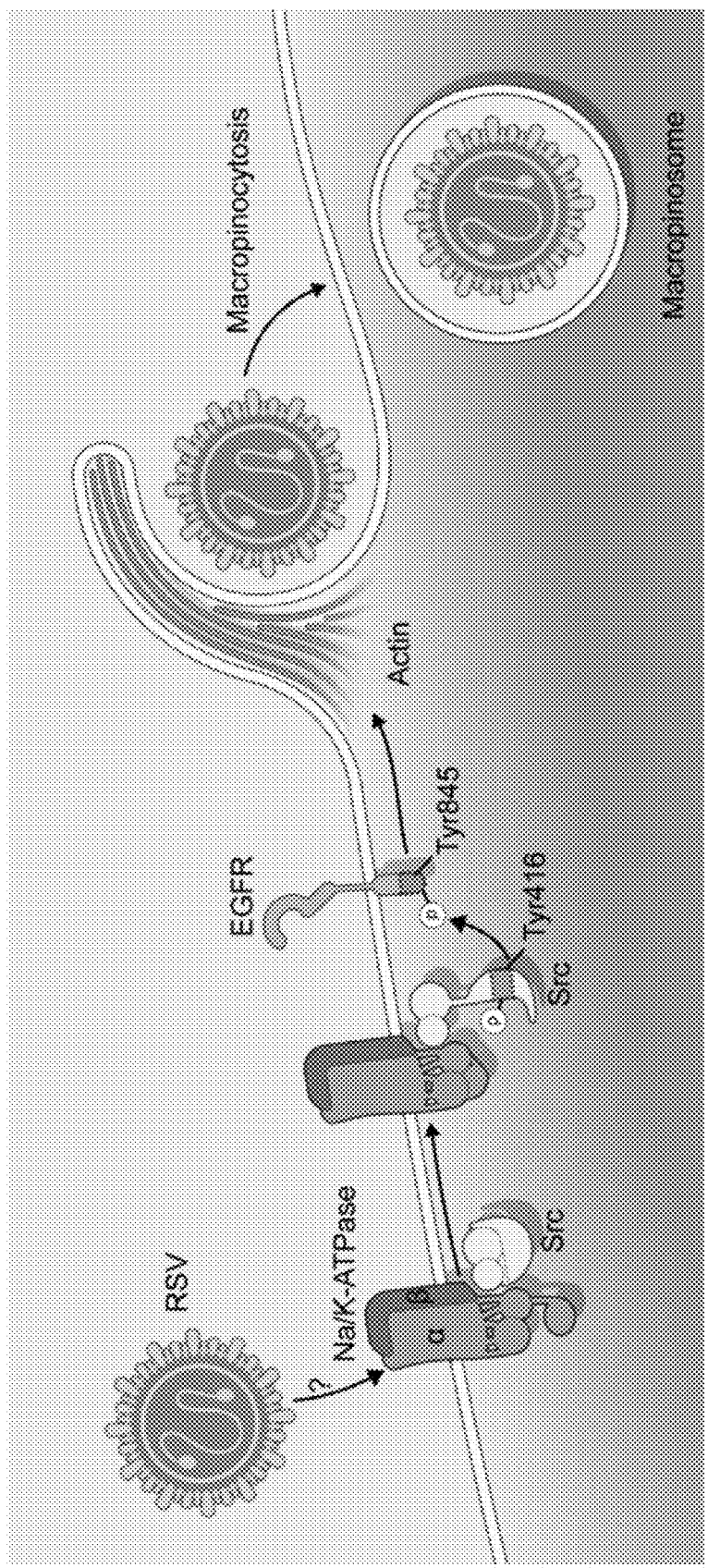
FIG. 12. Model of ATP1A1 dependent macropinocytic entry of RSV. On exposure to respiratory epithelial cells, RSV triggers the activation and clustering of ATP1A1 in the plasma membrane through an unknown mechanism. ATP1A1 then signals via phosphorylated Src kinase and transactivates EGFR by its phosphorylation at Tyr845. Upon activation, EGFR signaling causes cytoskeletal rearrangement resulting in plasma membrane ruffling and formation of membrane extensions that engulf fluid and RSV into membrane bound vesicles, the morphology of which is characteristic of macropinosomes. RSV is taken up into the macropinosome in its enveloped state suggesting that it does not fuse at the cell surface; fusion and release of nucleocapsid likely occurs after the macropinocytic event. RSV triggered ATP1A1 activation is independent of the direct physical interaction of ATP1A1 with the RSV surface G, F, or SH proteins but requires the presence of G protein on the virion surface which likely plays a role in an indirect manner. The entry pathway requires both the presence and signaling function of ATP1A1; EGFR and Src kinase are also essential but not sufficient alone and require the activation of upstream ATP1A1 to mediate RSV entry. The model illustrates a signaling pathway comprised of three main components, ATP1A1, Src kinase, and EGFR, whose activation and cross-talk leads to macropinocytic entry of RSV into the host cell.

A model for RSV entry into the human airway epithelial cells is illustrated in FIG. 12. RSV infection activates ATP1A1 signaling by an unknown mechanism that involves RSV G protein and does not involve viral RNA synthesis or replication. Activation of ATP1A1 leads to autophosphorylation of c-Src and transactivation of EGFR. Signaling events downstream of EGFR cause actin rearrangement and ruffling at the plasma membrane, where membrane extensions engulf fluid and RSV into large vesicles known as macropinosomes. RSV is taken up in its enveloped form into the macropinosome followed by fusion and entry into the host cell. Evidence is provided that the ATP1A1-Src-EGFR signaling occurs predominantly in the cholesterol rich domains of the caveolae which are thus important for efficient infection. This study identified ATP1A1 signaling as a new target for the development of anti-RSV agents and shows that PST2238 is an example of such an agent.

Materials and Methods

Cells and viruses. A549 cells (ATCC CCL-185) were maintained in F12-K media (ATCC, Manassas, Va.) supplemented with 10% fetal bovine serum (FBS, Thermo Scientific, Atlanta, Ga.) and 1× L-Glutamine (Life Technologies, Grand Island, N.Y.), Vero cells (ATCC CCL-81) were maintained in Opti-MEM I medium with GlutaMax-I (Life Technologies) supplemented with 5% FBS. The normal primary human small airway epithelial cells (HSAEC) (ATCC PCS-301-010) were derived from a 16-year-old male Hispanic/Latino donor (Lot: 64079184) and were maintained in airway cell basal medium (ATCC PCS-300-030), supplemented with bronchial epithelial cell growth kit (ATCC PCS-300-040). The primary cells were passaged a maximum of two times to ensure the maintenance of the primary cell characteristics and to avoid any cell culture adaptation. For seeding and maintenance, the cells were detached with Trypsin-EDTA for primary cells (ATCC PCS-999-003) and Trypsin neutralizing solution (ATCC PCS-999-004). HAE-ALI cultures (EpiAirway, AIR-100) were obtained from MatTek Corporation (Ashland, Mass.) and were cultured at the air-liquid interface as described in the manufacturer's protocol with the provided maintenance medium, with daily medium changes. The recombinant viruses RSV-GFP (Munir et al., *J Virol.* 2008; 82(17):8780-96), wt RSV A2 (Genbank accession #KT992094), rgRSV-dSH and rgRSV-dSH dG (Techaarpornkul et al., *J Virol.* 2001; 75(15):6825-34) have been previously described. For all experiments, virus stocks were purified on a discontinuous (60% and 30% w/v) sucrose gradient as described previously (Munir et al., *J Virol.* 2008; 82(17):8780-96).

Inhibitors and chemical compounds. The chemical compounds and inhibitors ouabain (PubChem CID: 439501), PST2238 (rostafuroxin, PubChem CID: 153976), Src-Inhibitor-I (PubChem CID: 1474853), PP2 (PubChem CID: 4878), methyl-beta-cyclodextrin (MBCD, PubChem CID: 51051622) and Mevinolin (Lovastatin, PubChem CID: 53232) were obtained from Sigma-Aldrich, St. Louis, Mo. 50 µM ouabain stock solution was prepared in sterile ultra-pure water. 10 mM stock solutions of PST2238, Src-Inhibitor-I and PP2 were prepared in DMSO. 76.3 mM MBCD stock solution was prepared in F12 media. 1 mg/ml Mevinolin stock solution was prepared in 200 proof ethanol. Working stock solutions, at concentrations as indicated, were prepared in the appropriate cell culture media. Non-toxic concentrations for all chemical compounds were determined by serial dilution on A549 (see FIG. 16) and the cytotoxicity were quantified by the ATP-based viability assay, as described below. The final DMSO concentration was below 0.2% and was considered not to have any effect on the cells as determined by DMSO control treated cells (FIG. 16).

siRNA transfection to knock down the host proteins ATP1A1 and EGFR. To knock down the cellular proteins ATP1A1 and EGFR in A549 cells and HSAEC, cells were siRNA transfected by reverse transfection protocol with siLentFect transfection reagent (Bio-Rad, Hercules, Calif.) in a 12-well plate. For the ATP1A1 and EGFR knock down the following siRNAs (obtained from Qiagen, Germantown, Md.) were used: Hs_ATP1A1_5 (named siRNA1, CCC GGA AAG ACT GAA AGA ATA, SEQ ID NO: 1), Hs_ATP1A1_6 (named siRNA2, CTT GAT GAA CTT CAT CGT AAA, SEQ ID NO: 2), Hs_ATP1A1_7 (named siRNA3, ATC CAT GAA GCT GAT ACG ACA, SEQ ID NO: 3), Hs_EGFR_3 (named EGFR siRNA, CAG AGG AAA TAT GTA CTA CGA, SEQ ID NO: 4). The following controls were included in all siRNA transfection studies: Two negative control siRNAs, Neg. siRNA 1 (AllStars Neg. Conrol siRNA [Qiagen 1027281, sequence proprietary]) and Neg. siRNA 2 (Negative Control siRNA (Qiagen 1027310, AAT TCT CCG AAC GTG TCA CGT, SEQ ID NO: 5) were used to control for any unspecific siRNA transfection effects. The cell death positive control siRNA (AllStars Hs Cell Death siRNA control [Qiagen 1027299]) was used to control for an efficient transfection. Transfected A549 cells were incubated for 48 h, to ensure an efficient reduction of the target protein, before they were used for any further studies, e.g. RSV infection.

Cell viability assay. The ATP based cell viability assay CELLTITER-GLO® (PROMEGA®, Madison, Wis.) was used for the evaluation of the cell viability and performed as described by the manufacturer's protocol. Cells, that were seeded in white 96-well plates, were lysed after the specified treatment at indicated time points and the ATP concentration was determined by luciferase activation. The luciferase light emission was analyzed using a Synergy 2 ELISA reader (BioTek, Winooski, Vt.). The viability was reported relative to mock-treated cells, based on the reduction of luciferase light emission and hence reduction of ATP, which was used as a parameter for cell viability.

Western blot analysis for the quantification of ATP1A1 in knock down A549 cells. A549 or HSAEC cells were seeded in 12-well plates and transfected with the indicated siRNAs, as described above. Cells were lysed with 75 µl 1×LDS sample buffer (Life Technologies) at indicated time points. 22.5 µL lysate was reduced, denatured, and electrophoresed on a 4-12% Bis-Tris SDS gel (Life Technologies). Proteins were transferred onto a PVDF membrane via the iBlot2 transfer system (Life Technologies) and analyzed by Western blotting. ATP1A1 was detected with a rabbit monoclonal anti-ATP1A1 (Abcam, Cambridge, Mass.; ab76020) antibody and the corresponding infrared dye-conjugated goat anti-rabbit immunoglobulin 680RD (Li-Cor, Lincoln, Nebr.). Tubulin was used as a loading control and was detected with a mouse anti-tubulin antibody and an infrared dye-conjugated goat anti-mouse immunoglobulin 800CW (Li-Cor). Western blot images were acquired on the Odyssey infrared scanner (Li-Cor) and analyzed with Image Studio Software (Version 5.2.5, Li-Cor). ATP1A1 band intensity values were normalized to tubulin and reported relative to Neg. siRNA1 transfected cells.

Quantitative RT-PCR. Cells were harvested and total RNA was isolated with RNeasy Mini Kit (Qiagen) as described by the manufacture's protocol, including on-column DNase digestion to avoid any DNA contamination. 1 µg total RNA was used for reverse transcription of mRNA to cDNA with oligo(dT) 12-18 primers and the SuperScript™ First-Strand Synthesis System for RT-PCR (Life Technologies). The synthesized cDNA was pre-diluted 1:10 and used for the TaqMan gene expression analysis of ATP1A1 (Hs00167556_m1) and 18S rRNA (Hs99999901_s1) as a normalization control. The TaqMan assay reactions were analyzed on the 2900HT Fast Real-Time PCR system (Applied Biosystems, Foster City, Calif.). The threshold cycle (Ct) for each reaction was determined by the SDS RQ manager program (Applied Biosystems). The relative changes in ATP1A1 transcript level were calculated by the $2^{-\Delta\Delta Ct}$ method (Livak et al., *Methods*. 2001; 25(4):402-8) and reported as fold change relative to cells transfected with Neg. siRNA 1.

Quantification of RSV infection by viral expressed GFP. For the evaluation of RSV infection, RSV-GFP, a recombinantly derived virus that expresses enhanced green fluorescent protein (eGFP) from an additional gene inserted between the P and M genes, was used. SiRNA transfected or pre-treated A549 cells, seeded in a 12-well plate, were inoculated with an MOI of 1.0 PFU/cell. Inoculum was adsorbed for 2 h by incubating on a rocking platform at 37° C., after which the inoculum was washed off and replaced with fresh media. The infected cells were incubated for 17 h at 37° C. and 5% $CO_2$ and the infectivity was evaluated by quantifying GFP either by ELISA reader or flow cytometry. For the ELISA reader quantification, the GFP intensity of the infected monolayer was quantified by an area scan (average GFP intensity of 29 individual measurements per well) on a Synergy 2 ELISA reader (BioTek). The intensity values were background subtracted and reported as fold-change relative to Neg. siRNA 1 transfected or mock-treated cells that had been infected with RSV-GFP. For the flow cytometry based GFP quantification, the cells were detached with 1 mM EDTA, stained with LIVE/DEAD fixable dead cell staining kit (Life Technologies), and fixed with 4% paraformaldehyde (PFA, Electron Microscopy Science, PA). The GFP intensities of single, live cells were analyzed on a Canto II flow cytometer (BD Biosciences, Franklin Lakes, N.J.). The median fluorescence intensity (MFI) of GFP-positive cells was determined and reported as change relative to Neg. siRNA 1 transfected or mock-treated cells that had been infected with RSV-GFP.

Virus titration. A plaque assay was performed to determine the total (supernatant plus cell-associated) RSV plaque forming unit (PFU) titer. Infected cell monolayers were scraped into the media supernatant and collected at indicated time points post inoculation. The samples were intensively vortexed and clarified by centrifugation, snap frozen on dry-ice and stored at −80° C. until further processed. Samples were 10-fold serially diluted and Vero cells were inoculated with each dilution in duplicates and incubated for 2 h on a rocking platform at 37° C. To limit the diffusion of free virus, cells were overlaid with OptiMEM I (Life Technologies) containing 0.8% methylcelluluose (Sigma-Aldrich), 1× L-Glutamine, 2% FBS and 50 µg/ml Gentamicin. Cells were incubated for 6 days at 37° C., 5% $CO_2$. For RSV that expressed GFP, the plaques were visualized directly by GFP expression, which was imaged on a Typhoon imaging system (GE Healthcare, Chicago, Ill.). The wt RSV plaques were detected by immunostaining after fixation with ice-cold 80% methanol. A mix of three primary mouse monoclonal antibodies directed against RSV-F followed by a 680RD infrared dye-conjugated goat anti-mouse secondary immunoglobulin (Li-Cor) were used. The plaques were imaged on the Odyssey infrared scanner (Li-Cor) and were counted using macros within the software ImageJ (Version 1.46r; NIH, Bethesda, Md.).

Immunofluorescence microscopy. A549 cells were seeded on glass cover slips in 24-well plates and were treated, as indicated, when sub-confluent. For the immunofluorescence microscopy-based assays, cells were fixed with 4% paraformaldehyde overnight at 4° C., permeabilized with 0.1% TRITON™ X-100 (Sigma Aldrich) for 15 min and blocked with PBS containing 5% BSA (Sigma Aldrich) for 1 h at room temperature. All antibody dilutions were prepared in PBS, containing 5% BSA and 0.1% TRITON™ X-100. The primary antibody incubation was performed in a humidified chamber for 2 h with the following antibodies, depending on the target of interest for the specific assay: rabbit anti-ATP1A1 (ABCAM®; ab76020, 1:100), rat anti-EGFR (Abcam; ab231, 1:100), mouse anti-RSV-N (AB-CAM®; ab94806, 1:1,500) and mouse monoclonal anti-RSV-F (1129). After washing with PBS, the secondary antibody staining was performed with the respective Alexa Fluor (AF) conjugated secondary antibodies: donkey anti-rabbit AF488, goat anti-rabbit AF700, donkey anti-mouse AF647, goat anti-rat AF647. Primary conjugated antibodies were used for staining infected cells for RSV-F and RSV-N simultaneously. Mouse monoclonal anti-RSV-F (1129) was conjugated with AF488 [Antibody Labeling Kit (Thermo Fisher Scientific, Waltham, Mass.)] and for RSV-N the allophycocyanin (APC) conjugated mouse monoclonal anti-RSV N antibody (Novus Biologicals, Littleton, Colo.) was used. The nuclei were counterstained with DAPI (Life Technologies) at a concentration of 300 nM in PBS for 5 min and mounted on glass-slides with ProLong Diamond Antifade mountant (Life Technologies) Immunostainings of HAE-ALI cells were performed as described above for A549 cells, except the incubation times of the primary and secondary antibodies were extended to 16 h at 4° C. In addition, the cultures were stained for F-Actin with the SiR-actin kit (CY-SC001; Cytoskeleton; Inc, Denver, Colo.). Images were acquired on a Leica TCS-SP8 confocal microscope (Leica Microsystems, Mannheim, Germany) using a 63× oil immersion objective (NA 1.4) and a zoom between 1.0 to 3.5×. Fluorochromes were excited using an argon laser at 488 nm for AF488, 561 nm for AF568 and 633 nm for AF647. DAPI was excited using a 450 nm diode laser. Detector slits were configured to minimize any crosstalk between the channels and, if necessary, the channels were collected sequentially and merged afterwards. Images were processed using Leica Application Suite X (LAS-X) software, Imaris (Version 9.0.0, Bitplane AG, Zurich, Switzerland) and ImageJ.

Quantification of EGFR phosphorylation. To analyze the ATP1A1 signaling induced EGFR phosphorylation, an EGFR phosphorylation array (RAYBIOTECH®, Norcross, Ga.) was used that probed for the phosphorylation of 17 different sites of the EGFR receptor family Cells were treated as indicated, either transfected with siRNA 48 h prior or pre-treated with the indicated chemical compound overnight. All cells were starved overnight in FBS-free media and incubated with wt RSV (MOI=5 PFU/cell) for 5 h at 37° C., 5% $CO_2$. Cells treated with Ouabain or PST2238 for 16 h were incubated in F12 medium containing EGF (Sigma-Aldrich, 100 ng/ml) for 45 min as controls for PST2238 and Ouabain specificity. Cells were washed twice with cold PBS and lysed in the provided lysis buffer, containing protease and phosphatase inhibitor cocktails. The protein concentration of the lysate was quantified by bicinchoninic acid (BCA) assay (Thermo Fisher Scientific) and lysate containing 150 μg total protein was used for each array. The array was processed as described by the manufacture's protocol, in brief: The array was incubated with the diluted lysate overnight at 4° C. on a rocking platform, washed and incubated with a biotinylated anti-panEGFR antibody, followed by horse radish peroxidase conjugated streptavidin. The light emission of the array spots was detected by exposure to X-ray films. The films were scanned and the intensity values of each spot were quantified by ImageQuant TL (Array Version 8.1, GE Healthcare). The phospho EGFR signals of three independent experiments with two technical replicates were normalized to the signal of the array internal positive controls and pan EGFR. Signals are reported as fold-change relative to the average signal of mock-treated, RSV infected samples.

Dextran assay. For the determination of the macropinocytic uptake activity of cells, AF568 conjugated Dextran (10.000 MW; Life Technologies) was used as a fluidic uptake marker. The uptake was quantified by confocal microscopy as described (Wang et al., *MethodsX*. 2014; 1:36-41). In brief, A549 cells seeded on cover slips, that had been transfected with siRNA 48 h prior or pre-treated with indicated chemical compounds overnight, were serum starved. Cells were infected with wt RSV (MOI=5 PFU/cell) in media containing AF568 conjugated Dextran (Dextran-AF568), incubated for 5 h at 37° C., washed and fixed overnight with 4% PFA at 4° C. The cells were counterstained with DAPI (300 nM in PBS for 5 min) and mounted on glass-slides with PROLONG™ Diamond Antifade mountant. For each treatment at least ten random images, using the mark and find function of the Leica LAS-X image acquisition software, were acquired as Z-stacks on a Leica TCS-SP8 confocal microscope (LEICA®) with a 63× Objective (NA 1.4) and a zoom of 1.0×. The images were analyzed by batch process with the software Imaris (Version 9.0.0, Bitplane AG). The DAPI stained nuclei were detected as spots to count the number of cells per field. The uptake of dextran was quantified by creating surfaces that recognize distinct dextran positive vesicles and disregards any background staining. The total intensity of Dextran-AF568 within the created surfaces, which had a volume larger than 1.0 $\mu m^3$, of one field was normalized to the number of nuclei per field. The values were reported as fold change relative to Neg. siRNA 1 transfected cells that had been infected with RSV. For each experiment at total of at least 600 cells per condition were analyzed.

It will be apparent that the precise details of the methods or compositions described may be varied or modified without departing from the spirit of the described embodiments. We claim all such modifications and variations that fall within the scope and spirit of the claims below:

It is claimed:

1. A method of inhibiting replication of a Respiratory Syncytial Virus (RSV) in a subject, comprising administering a therapeutically effective amount of an agent to the subject to inhibit replication of the RSV, wherein the agent is PST2238, thereby inhibiting replication of the RSV in the subject.

2. The method of claim 1, wherein the agent is administered to the subject by oral, intranasal, inhalation, intramuscular, intravenous, peritoneal, or subcutaneous administration.

3. The method of claim 2, wherein the agent is administered intranasally to the subject.

4. The method of claim 2, wherein the agent is administered to the subject with a nebulizer.

5. The method of claim 1, wherein the subject is human.

6. The method of claim 5, wherein the human is over 65 years old.

7. The method of claim 5, wherein the human is a child.

8. A method of treating a Respiratory Syncytial Virus (RSV) infection in a subject, comprising administering to the subject a therapeutically effective amount of PST2238, thereby treating the RSV infection in the subject.

9. The method of claim 8, comprising administering PST2238 to the subject by oral, intranasal, inhalation, intramuscular, intravenous, peritoneal, or subcutaneous administration.

10. The method of claim 8, comprising administering PST2238 to the subject intranasally.

11. The method of claim 8, comprising administering PST2238 using a nebulizer.

12. The method of claim 8, wherein the subject is human.

13. The method of claim 12, wherein the human is over 65 years old.

14. The method of claim 12, wherein the human is a child.

15. The method of claim 8, wherein the method reduces symptoms of the RSV infection in the subject.

\* \* \* \* \*